(12) United States Patent
Unno

(10) Patent No.: US 7,024,281 B1
(45) Date of Patent: Apr. 4, 2006

(54) SOFTWARE FOR THE CONTROLLED SAMPLING OF ARRAYED MATERIALS

(75) Inventor: Garrett Unno, San Jose, CA (US)

(73) Assignee: Callper Life Sciences, Inc., Mountain View, CA (US)

( * ) Notice: Subject to any disclaimer, the term of this patent is extended or adjusted under 35 U.S.C. 154(b) by 362 days.

(21) Appl. No.: 10/021,894

(22) Filed: Dec. 10, 2001

Related U.S. Application Data

(60) Provisional application No. 60/255,230, filed on Dec. 11, 2000.

(51) Int. Cl.
- *G05B 21/00* (2006.01)
- *G05B 13/00* (2006.01)
- *G05B 15/00* (2006.01)
- *G01M 1/38* (2006.01)

(52) U.S. Cl. .......................... 700/275; 700/1; 700/11; 700/18; 700/19; 700/20; 700/90; 700/266; 422/50; 422/62; 422/63; 422/67; 422/68.1; 422/100; 422/101; 422/102; 422/103; 422/104; 436/43; 436/63

(58) Field of Classification Search .................... 700/1, 700/11, 18, 19, 20, 90, 266, 275; 422/50, 422/62, 63, 67, 68.1; 436/43, 63
See application file for complete search history.

(56) References Cited

U.S. PATENT DOCUMENTS

| 5,942,443 | A | 8/1999 | Parce et al. | |
| 6,132,685 | A | 10/2000 | Kercso et al. | |
| 6,207,031 | B1 * | 3/2001 | Adourian et al. | 204/451 |
| 6,235,471 | B1 | 5/2001 | Knapp et al. | |
| 6,495,369 | B1 * | 12/2002 | Kercso et al. | 436/47 |

* cited by examiner

*Primary Examiner*—Brian J. Sines
(74) *Attorney, Agent, or Firm*—Donald R. McKenna; Ann C. Petersen

(57) ABSTRACT

Computer implemented methods for contacting or sampling materials in arrays having x materials sites with microfluidic devices having n capillary elements are provided. Devices, integrated systems, and computer program products for performing these methods are also provided.

45 Claims, 50 Drawing Sheets

A

|   | 0 | 1 | 2 | 3 | 4 | 5 |
|---|---|---|---|---|---|---|
| 0 | 0 | 0 | 0 | 0 | 1 | 1 |
| 1 | 1 | 0 | 0 | 0 | 0 | 1 |
| 2 | 1 | 0 | 0 | 0 | 0 | 1 |
| 3 | 1 | 1 | 0 | 0 | 0 | 0 |

B

|   | 0 | 1 | 2 | 3 | 4 | 5 |
|---|---|---|---|---|---|---|
| 0 | 1 | 1 | 1 | 1 | 1 | 1 |
| 1 | 1 | 0 | 0 | 0 | 0 | 1 |
| 2 | 1 | 0 | 0 | 0 | 0 | 1 |
| 3 | 1 | 1 | 0 | 0 | 1 | 0 |

C

|   | 0 | 1 | 2 | 3 | 4 | 5 |
|---|---|---|---|---|---|---|
| 0 | 1 | 1 | 1 | 1 | 1 | 0 |
| 1 | 1 | 1 | 1 | 1 | 0 | 0 |
| 2 | 1 | 1 | 1 | 0 | 0 | 0 |
| 3 | 1 | 1 | 0 | 1 | 0 | 0 |

D

|   | 0 | 1 | 2 | 3 | 4 | 5 |
|---|---|---|---|---|---|---|
| 0 | 1 | 1 | 1 | 1 | 1 | 0 |
| 1 | 1 | 1 | 1 | 1 | 1 | 0 |
| 2 | 1 | 1 | 1 | 1 | 0 | 0 |
| 3 | 1 | 1 | 1 | 0 | 0 | 0 |

E

|   | 0 | 1 | 2 | 3 | 4 | 5 |
|---|---|---|---|---|---|---|
| 0 | 1 | 1 | 1 | 1 | 1 | 1 |
| 1 | 1 | 1 | 1 | 1 | 1 | 1 |
| 2 | 1 | 1 | 1 | 1 | 1 | 1 |
| 3 | 1 | 1 | 1 | 1 | 1 | 1 |

Fig. 3

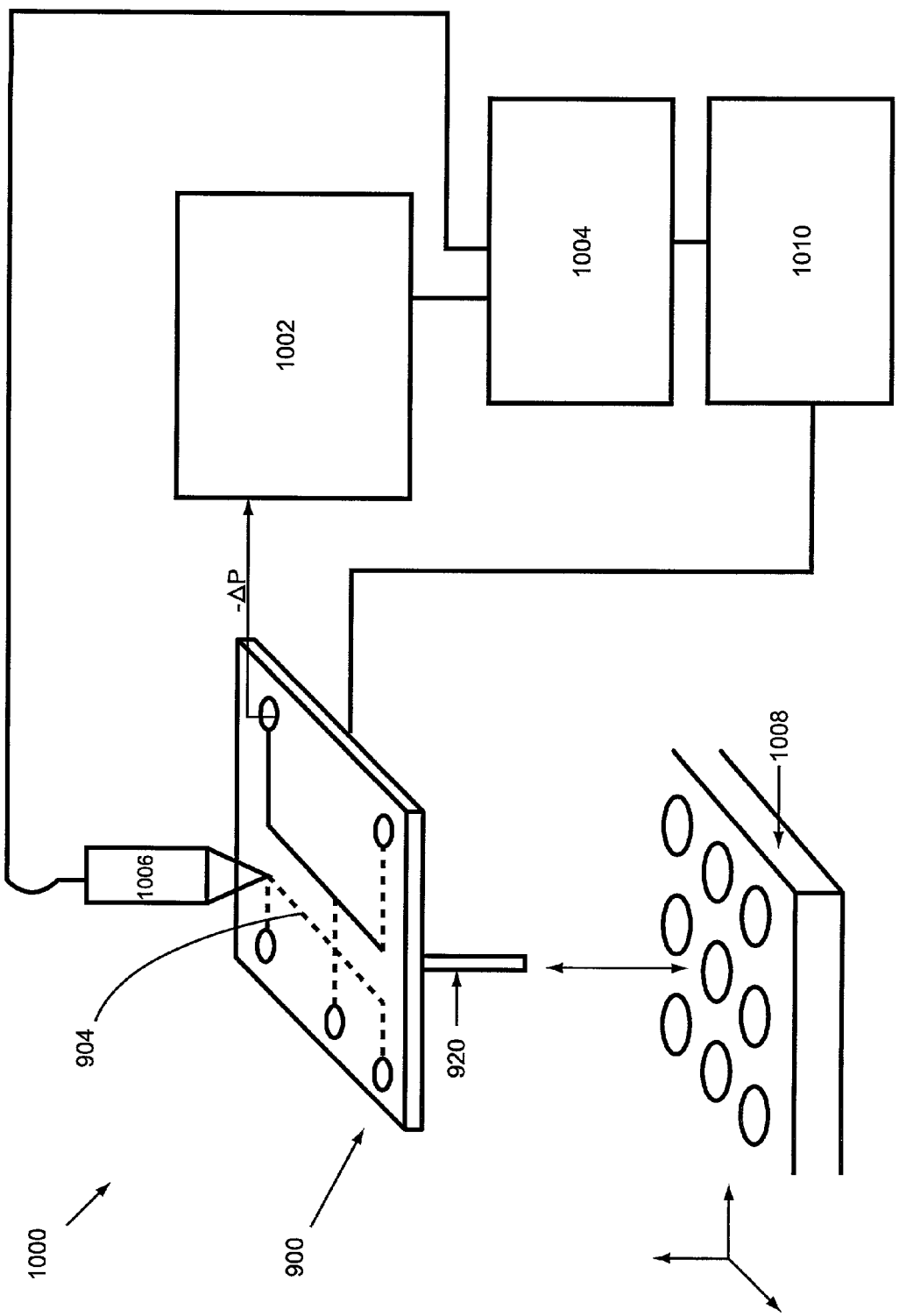

Dwell Pattern

Name: FewNoTrough.DP4_96

Row A: 5,6

Fig. 11B

Dwell Pattern

Name: FewTrough.DP4_96

Row A: 1,2

Fig. 11D

Dwell Pattern

Name: SeveralNoTrough.DP4_96

Row A: 5,6,9,10

Fig. 11F

┌─ Dwell Pattern ─────────────────────────┐
│                                          │
│  Name: │ SeveralTrough.DP4_96         │  │
│        ┌──────────────────────────────┐  │
│        │ Row A: 1,2,5,6,9,10          │  │
│        │                              │  │
│        │                              │  │
│        └──────────────────────────────┘  │
└──────────────────────────────────────────┘

Fig. 11H

Dwell Pattern

Name: HalfNoTrough.DP4_96

Row A: 5,6,9,10
Row B: 5,6,9,10

Fig. 11J

Dwell Pattern

Name: HalfTrough.DP4_96

Row A: 1,2,5,6,9,10
Row B: 1,2,5,6,9,10

Fig. 11L

Dwell Pattern

Name: FullNoTrough.DP4_96

Row A:  5,6,9,10
Row B:  5,6,9,10
Row E:  5,6,9,10
Row F:  5,6,9,10

Fig. 11N

Dwell Pattern

Name: FullTrough.DP4_96

Row A: 1,2,5,6,9,10
Row B: 1,2,5,6,9,10
Row E: 1,2,5,6,9,10
Row F: 1,2,5,6,9,10

Fig. 11P

SOFTWARE FOR THE CONTROLLED SAMPLING OF ARRAYED MATERIALS

CROSS-REFERENCES TO RELATED APPLICATIONS

Pursuant to 35 U.S.C. §§ 119 and/or 120, and any other applicable statute or rule, this application claims the benefit of and priority to U.S. Ser. No. 60/255,230, filed on Dec. 11, 2000, the disclosure of which is incorporated by reference.

COPYRIGHT NOTIFICATION

Pursuant to 37 C.F.R. § 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

Modern pharmaceutical discovery increasingly relies on combinatorial approaches to simultaneously generate millions of compounds with potential biological activity and on high-throughput screening to rapidly assay each of these compounds for selected biological activities. A basic rationale supporting these combinatorial synthetic methodologies is that producing larger, more diverse compound libraries increases the probability of finding novel compounds with significant therapeutic and commercial value. The field of combinatorial chemistry represents a convergence of chemical and biological disciplines, facilitated by fundamental innovations in miniaturization, robotics, and receptor development.

Combinatorial chemistry includes systematic and repetitive organic synthetic techniques that utilize sets of chemical precursors or building blocks to form a diverse set or library of molecular species. Active compounds are typically identified within populations, either spatially, through chemical encoding, or by systematic, successive synthesis and biological evaluation or deconvolution. For example, in one common combinatorial organic synthetic approach two-dimensionally arrayed chemical precursors are reacted systematically in individual reaction wells or material sites to form distinct and addressable compounds. Thereafter, active compounds are identified according to their location in or on the array. Another approach, known as encoded mixture synthesis, utilizes various types of chemical tags to identify active compounds. Other combinatorial organic synthetic approaches include the synthesis of a series of compound mixtures, in which specific structural features are attached or modified at each stage. Mixtures are then assayed, with the most active combinations being pursued. Subsequent rounds systematically attach or modify other structural features until manageable numbers of discrete structures can be synthesized and screened.

In general, methods to enhance the throughput of microfluidic applications, including microfluidic screening techniques, would be desirable. The present invention provides new computer implemented methods and associated devices for rapidly contacting or sampling materials in or on arrays having essentially any number of materials sites, with microfluidic devices having essentially any number of capillary elements. The methods have many significant advantages over current approaches, including current combinatorial compound library screens. These and a variety of additional features will become apparent upon complete review of the following.

SUMMARY OF THE INVENTION

The present invention generally provides innovative techniques for contacting or sampling arrayed materials. In particular, the invention relates to computer implemented methods or algorithms for controlling contacting or sampling patterns between microfluidic devices having essentially any number of capillary elements extending therefrom and arrays of materials having essentially any number of material sites. The methods provide for the rapid and optimized processing of arrayed materials. The invention additionally includes integrated systems which implement the methods under the direction of computers instructed by the algorithms and computer program products (e.g., software, etc.).

In one aspect, the present invention relates to a computer implemented method for selectively contacting microfluidic devices and arrayed materials. The method includes (a) providing a microfluidic device handling system operably connected to a computer in which the microfluidic device handling system is capable of implementing relative movement of a microfluidic device having n capillary elements extending therefrom, of an array of materials having x material sites or at least one container (e.g., recirculation/ replenishing bath or trough, etc.), or of both, under instruction of the computer. A capillary element typically includes a capillary channel disposed therethrough. The method further includes (b) inputting initial parameters for the microfluidic device and the array into the computer. The computer includes a simple logic control program for selectively contacting a capillary element and material at a selected material site disposed in or on a surface of the array. In addition, the method includes (c) implementing the simple logic control program to effect: (i) moving the microfluidic device relative to the array, the array relative to the microfluidic device, or both, according to the initial parameters, and (ii) contacting the capillary element and the material at the selected material site. Optionally, (ii) further includes drawing a selected quantity or volume of the material into the microfluidic device through the capillary element. The simple logic control program generally optimizes a course for selectively contacting (e.g., sampling or drawing material from the material site) the capillary element and the material at the selected material site.

The method also typically includes (iii) updating the initial parameters and optionally, (iv) repeating (i), (ii), and (iii) until each selected capillary element of the microfluidic device and materials at each selected material site are contacted (e.g., sampled). The simple logic control program generally automatically directs each (i), (ii), and (iii). For example, the simple logic control program typically automatically updates the initial parameters by deselecting material at each material site contacted by the capillary element following each repeated cycle of (i) and (ii). According to this computer implemented method, any pattern or course for contacting selected capillary elements of a given capillary element configuration and selected materials from essentially any arrangement and number of arrayed materials is optionally designed. To illustrate, in certain embodiments, individual capillary elements of a particular capillary element configuration optionally contact all or less than all material sites of the particular array being processed according to the user's selections and/or deselections. To further illustrate the flexibility of the methods, systems and software provided herein, all material sites of an array are optionally visited (e.g., materials disposed therein or thereon contacted or sampled), but by different capillary elements of the capillary element configuration of the particular microfluidic device used to process the array.

In certain embodiments, the material is a first fluidic material. In these embodiments, (ii) typically includes dipping the capillary element into the first fluidic material at the selected material site. Optionally, (b) further includes inputting one or more initial parameters for the container into the computer, which also includes a simple logic control program for selectively contacting the capillary element and a second fluidic material disposed in the container. Additionally, (c) optionally further includes (iii) moving the microfluidic device relative to the container, the container relative to the microfluidic device, or both, according to the initial parameters or updated parameters, and (iv) dipping the capillary element into the second fluidic material, and moving the second fluidic material relative to the capillary element or moving the capillary element relative to the second fluidic material. The second fluidic material is typically disposed in at least one other selected material site of the array, or in a fluidic container distinct from the array. For example, the second fluidic material is optionally in a fluid stream or in a fluid recirculation/replenishing bath or trough. In one embodiment, (iv) further includes moving both the capillary element and the second fluid material simultaneously relative to one another. The second fluid material typically includes a solution, such as a wash solution, a rinse solution, a buffer solution, a reagent solution, a sample solution, a spacer solution, or the like. A further option includes, (v) moving the microfluidic device relative to the array, the array relative to the microfluidic device, or both, according to the initial parameters or the updated parameters, and (vi) dipping the capillary element into a third fluidic material at at least one other selected material site in which (iv) dissipates a drop of the first fluidic material adhering to a portion of the capillary element into the second fluidic material, thus reducing fluid carryover from (ii) to (vi). In one embodiment, (ii) further includes drawing a portion of the first fluidic material into the capillary element. In another embodiment, (iv) further includes drawing a portion of the second fluidic material into the capillary element. In these embodiments, (iv) typically dissipates carried-over first fluidic material in the second fluidic material thus reducing an amount of the carried-over first fluidic material drawn into the capillary element.

The methods of the invention are capable of accommodating essentially any number or combination of microfluidic device capillary elements and arrayed materials sites. For example, n typically corresponds to at least about 1, 2, 4, 6, 8, 12, or more capillary elements, whereas x typically corresponds to at least about 1, 10, 50, 96, 250, 384, 500, 1000, 1536, 5000, 10000, 100000, or more material sites. In addition, the array generally includes a microwell plate, substrate, or membrane. To illustrate, the x material sites optionally correspond to x wells in the microwell plate (e.g., a 96, 384, or 1536 well plate), or to x sample sites on the substrate or membrane. For example, all or less than all material sites of a given array are optionally visited by at least one capillary element of the particular capillary element configuration being utilized according to user specifications. In one embodiment, the method also includes interchanging the microfluidic device with a different microfluidic device, the array with a different array, or both, in which the simple logic control program effects selective contacting of interchanged components.

The present invention also provides an integrated system that includes a computer and a microfluidic device handling system operably connected to the computer. The microfluidic device handling system is capable of implementing relative movement of a microfluidic device having n capillary elements extending therefrom, of an array of materials having x material sites or a container (e.g., recirculation/replenishing bath or trough, etc.), or of both, under instruction of the computer. A capillary element typically includes a capillary channel disposed therethrough. The integrated system also includes a computer readable medium operably connected to the computer that stores a simple logic control program for selectively contacting a capillary element and a material at a selected material site disposed in or on a surface of the array or a fluid in the container. The computer readable medium typically includes, e.g., a CD-ROM, a floppy disk, a tape, a flash memory device or component, a system memory device or component, a hard drive or other magnetic media, a data signal embodied in a carrier wave, or the like.

The simple logic control program includes an instruction set for causing the computer to receive inputted initial parameters; an instruction set for causing the computer to effect movement of the microfluidic device to the selected material site or to the container according to inputted initial parameters or updated parameters, to effect movement of the array or the container relative to the microfluidic device according to inputted initial parameters or updated parameters, or both; an instruction set for causing the computer to effect contact of the capillary element and the material or the fluid according to inputted initial parameters or updated parameters, and an instruction set for causing the computer to effect deselection of the selected material site following contact between the capillary element and the material. The simple logic control program also typically includes an instruction set for causing the computer to vary or select a rate or a mode of moving or contacting the capillary element and the material or the fluid, to vary or select a rate or a mode of moving the array or the at least one container, or both; an instruction set for causing the computer to effect drawing of selected quantities or volumes of the material from the selected material site into the microfluidic device through the capillary element according to inputted initial parameters or updated parameters while the capillary element and the material are in contact, to effect drawing of one or more selected quantities or volumes of the fluid from the container into the microfluidic device through the capillary element according to one or more inputted initial parameters or one or more updated parameters while the capillary element and the fluid are in contact, or both; or both additional instruction sets. In certain embodiments, the simple logic control program further includes an instruction set for causing the computer to automatically update inputted initial parameters or other parameters.

The microfluidic device handling system of the integrated system typically includes a holder configured to receive the microfluidic device, a container sampling region proximal to the holder configured to receive the array, and a controller. During operation of the handling system, the controller implements movement or interchange of the microfluidic device, the array, or both, contact between the capillary element and the material, and drawing or sampling of the material.

The present invention also provides a computer program product that includes a computer readable medium having a simple logic control program stored thereon for causing a computer to selectively contact a capillary element of a microfluidic device having n capillary elements extending therefrom and material at a selected material site of an array of materials having x material sites or fluid in a container. The computer readable medium optionally includes, e.g., a CD-ROM, a floppy disk, a tape, a flash memory device or component, a system memory device or component, a hard drive, a data signal embodied in a carrier wave, or the like.

BRIEF DESCRIPTION OF THE DRAWINGS

FIGS. 3A–3E schematically show binary representations of array masks for the wells of a microwell plate during various processing stages.

FIG. 10 schematically illustrates an integrated system that includes the microfluidic device of FIGS. 9A–9C.

DETAILED DISCUSSION OF THE INVENTION

I. Introduction

Figure 1:
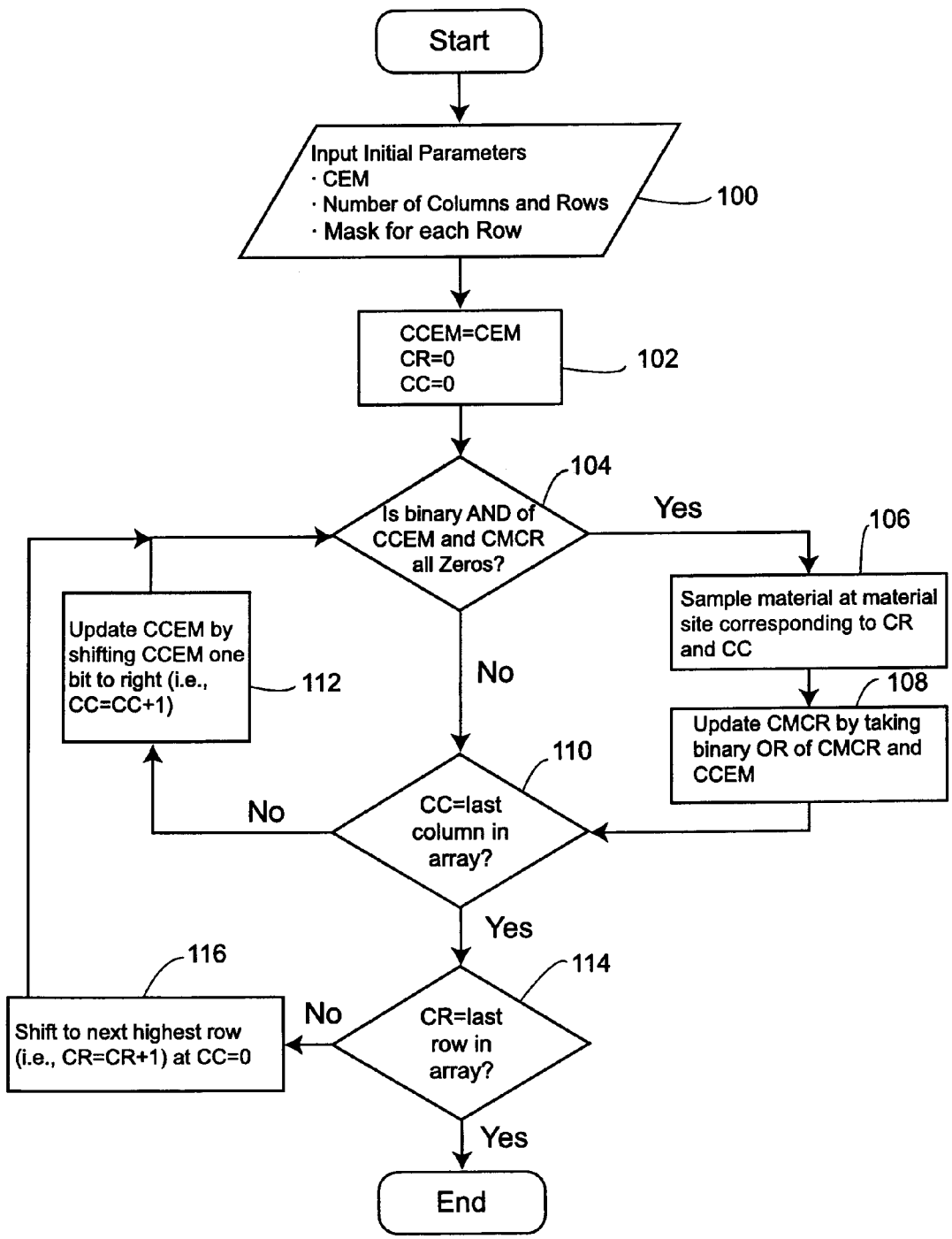
FIG. 1 shows a flowchart of an algorithm for sampling materials from an array of materials.

The present invention relates to the sampling of arrayed materials. More specifically, the invention provides computer implemented methods for regulating patterns of contacting or sampling materials in or on arrays having essentially any number of material sites with microfluidic devices having essentially any number of capillary elements. For example, the microfluidic devices of the invention include at least one capillary or pipettor element, but typically include multiple capillary elements. As used herein, a "capillary element" or a "pipettor element" includes a body structure having a channel (e.g., a microchannel, a capillary channel, or the like) disposed therethrough. The channel disposed through a capillary element typically has at least one internal cross-sectional dimension, e.g., depth, width, length, diameter, etc., that is less than 500 μm, and typically between about 0.1 μm and about 500 μm. A capillary element is alternatively a separate component that is temporarily coupled to multiple microfluidic device body structures or an integral extension of the body structure of a single microfluidic device.

One advantage of the invention is that instead of utilizing complex logic to direct microfluidic device handling systems, the methods described herein implement simple logic to locate selected material sites, then more simple logic to delete visited materials sites from inputted search lists before continuing on to other selected sites. In particular, the methods and devices of the invention utilize simple logic control programs or algorithms to direct and optimize the processing of arrayed materials. A "simple logic control program," as used herein, refers to a procedure, or a sequence of coded or computational instructions, for achieving a solution to a problem or for accomplishing some end based upon a Boolean system of symbolic logic, in which the opening and closing of electronic switches represent the truth values 1 (true) and 0 (false) and functions (i.e., Boolean operators), such as, AND, OR, NOT, or the like. For example, the binary AND of, e.g., two bits x and y is true only if both x and y are true, i.e., 1. Otherwise the result is false. By comparison, the binary OR of, e.g., two bits x and y is false, unless either x or y, or both is/are true, i.e., 1.

The simple logic control programs of the present invention eliminate problems associated with controlling sampling patterns of microfluidic devices using robotic handling systems when both array formats and capillary element configurations are variable (e.g., in multiple dimensions). In overview, the algorithms represent each material site (e.g., a well on a microwell plate, etc.) as a flag. To process an array, such as a microwell plate, the program searches for the first flag not set (i.e., those flags corresponding to user selected materials sites) and directs the robotic handling system to visit that material site. The program then sets or updates all of the flags corresponding to the material sites visited by the capillary elements of the particular microfluidic device. The program then resumes searching for the next flag not set. Optionally, the invention includes instruction sets that direct microfluidic device handling systems to reduce fluid carryover from one material site to another, e.g., by including intervening visits to recirculation/replenishing baths or troughs or the like. This process of searching and updating is repeated until all flags not set for a given array are visited.

In this approach, one algorithm easily accommodates essentially any number, combination, and/or density of microfluidic device capillary elements (e.g., a microfluidic device having n capillary elements) and arrayed materials sites (e.g., an array of materials having x material sites). For example, n typically corresponds to at least about 1, 2, 4, 6, 8, 12, or more capillary elements, whereas x typically corresponds to at least about 1, 10, 50, 96, 250, 384, 500, 1000, 1536, 5000, 10000, 100000, or more material sites. As a further example, capillary elements spaced, e.g., about 2 mm apart are optionally controlled to sample materials disposed at material sites spaced, e.g., about 1 mm apart. As indicated, however, essentially any density of capillary elements and/or material sites is optionally accommodated according to the methods described herein. In addition, the array generally includes a microwell plate, substrate, or membrane. To illustrate, the x material sites optionally correspond to x wells in the microwell plate, or to x sample sites on the substrate or membrane. In one embodiment, the method also includes interchanging the microfluidic device with a different microfluidic device, the array with a different array, or both, in which the simple logic control program effects selective contacting of interchanged components.

II. Methods of Sampling Arrayed Materials

The present invention provides a computer implemented method for selectively contacting microfluidic devices and arrayed materials. The method includes (a) providing a microfluidic device handling system operably connected to a computer in which the microfluidic device handling system is capable of implementing relative movement of a microfluidic device having n capillary elements extending therefrom, of an array of materials having x material sites, or of both, under instruction of the computer. Microfluidic device handling systems are described in greater detail below. A capillary element typically includes a capillary channel disposed therethrough. The method further includes (b) inputting initial parameters for the microfluidic device and the array into the computer. The computer includes a simple logic control program for selectively contacting a capillary element and material at a selected material site disposed in or on a surface of the array. In addition, the method includes (c) implementing the simple logic control program to effect: (i) moving the microfluidic device relative to the array, the array relative to the microfluidic device, or both, according to the initial parameters, and (ii) contacting the capillary element and the material at the selected material site. Optionally, (ii) further includes drawing a selected quantity or volume of the material into the microfluidic device through the capillary element.

The method also typically includes (iii) updating the initial parameters and optionally, (iv) repeating (i), (ii), and (iii) until each selected capillary element of the microfluidic device and materials at each selected material site are contacted (e.g., sampled). The simple logic control program generally automatically directs each (i), (ii), and (iii). For example, the simple logic control program typically automatically updates the initial parameters by deselecting material at each material site contacted by the capillary element following each repeated cycle of (i) and (ii). In certain embodiments, the material is a fluidic material. In these embodiments, (ii) typically includes dipping the capillary element into the first fluidic material at the selected material site. In one embodiment, (ii) further includes drawing a portion of the fluidic material into the capillary element.

The initial parameters generally include, e.g., an n-value (i.e., the number of capillary elements of the particular microfluidic device), an x-value (i.e., the number of material sites of the particular array), a capillary element mask, an array mask, a number of columns of material sites, a number of rows of material sites, a mask for each row of material sites, a selection of materials at material sites to be contacted, a quantity or volume of the material to be drawn from the at least one selected material site, a deselection of materials at material sites not to be contacted, or the like.

A "material site" refers to a location in or on an array that is capable of retaining a material, such as a fluidic material, a solid phase material, a sample, a reagent, a buffer, a dye, or the like. In certain embodiments, a material site is a well in a microwell plate. In other embodiments, a material site is a spot on a substrate or membrane that includes the material disposed thereon. For example, materials are optionally lyophilized or otherwise dried at material sites on substrates or membranes. An "array" refers to a structure that includes one or more material sites disposed therein or thereon in one or more dimensions. For example, in certain embodiments, an array is a microwell plate in which the wells correspond to the material sites, while in other embodiments, an array is a substrate or membrane having one or more selected locations on a surface that correspond to the material sites. The phrase "arrayed materials" refers to materials disposed, positioned, contained or otherwise situated in, on, or at one or more material sites of an array. Materials are typically arrayed in rows and columns, but also optionally include other configurations, such as concentric circles or the like.

Various materials are optionally arrayed and sampled according to the methods described herein. These optionally include, e.g., fluidic materials, lyophilized materials, biological molecules, artificial molecules, an ion, antibodies, antigens, inorganic molecules, organic molecules, drugs, receptors, ligands, neurotransmitters, cytokines, chemokines, hormones, particles, beads, functionalized beads, liposomes, cells, nucleic acids, DNAs, RNAs, oligonucleotides, ribozymes, proteins, phosphoproteins, glycoproteins, lipoproteins, peptides, phosphopeptides, glycopeptides, lipopeptides, enzymes, enzyme substrates, carbohydrates, lipids, labels, dyes, fluorophores, or the like.

A "mask" refers to a single- or multi-dimensional pattern, arrangement, or configuration of selected and/or deselected capillary elements of a microfluidic device and/or material sites in or on an array. A binary system is generally used to represent selected and deselected capillary elements or material sites in a given mask. According to this system, 1s and 0s or combinations thereof, or sets of 1s and 0s or combinations thereof (or alternate alphanumeric representations), represent, e.g., microfluidic device capillary element configurations, selected and/or deselected capillary elements in capillary element configurations, selected and/or deselected materials sites in or on an array or in a row or column of an array, or the like. More specifically, a "capillary element mask" refers to an overall capillary element pattern or configuration, or a portion thereof. A capillary element mask typically represents a selection and/or deselection of individual capillary elements in a microfluidic device, or a portion thereof, for contacting and optionally, drawing materials from one or more selected material sites of an array. An "array mask" represents a selection and/or deselection of material sites in a given array at which materials are to be contacted or not, or sampled or not. For example, a microwell plate optionally includes 96, 384, 1536, or essentially any other number of wells (i.e., material sites) disposed in a surface which are optionally selected and/or deselected. Similarly, an array in the form of a substrate or membrane may also include essentially any number of material sites disposed thereon which are also optionally selected and/or deselected.

The simple logic control program of the invention generally optimizes a course for selectively contacting (e.g., sampling or drawing material from the material site) the capillary element and the material at the selected material site. For example, the simple logic control program includes an instruction set for causing the computer to effect movement of the microfluidic device to the selected material site, to effect movement of the array relative to the microfluidic device, or both; an instruction set for causing the computer to effect contact of the capillary element and the material at the selected material site; and an instruction set for causing the computer to effect deselection of the selected material site following (ii). The simple logic control control program also typically includes an instruction set for causing the computer to effect drawing of selected quantities or volumes of the material from the selected material site during (ii).

FIG. 1 shows a flowchart representing one embodiment of a process for sampling materials from an array, such as a microwell plate. As shown, at step 100 the computer system receives a series of inputted parameters including, e.g., a capillary element mask (CEM) (e.g., a number and/or configuration of capillary elements extending from the microfluidic device), a number of rows and columns of material sites, and a mask for each row (i.e., a selection and/or deselection of material sites to be visited by the capillary elements). At the outset, as shown in step 102, the current capillary element mask (CCEM) is the same as the inputted CEM. As an array of materials is processed, the CCEM is updated by, e.g., deselecting or alternatively flagging visited materials sites. As also shown in step 102, the current row (CR) and current column (CC) are both initially zero in this illustration, e.g., corresponding to the well in the upper left corner of a microwell plate. Optionally, other initial values are inputted for the current row and current column, such that processing begins at a different material site or well in or on the array.

At step 104, for the CR and CC, the program determines whether the binary AND of the CCEM (e.g., the initial or last updated CCEM) and the current mask for the current row (CMCR) is all zeros. Initially, the CMCR is the same as the inputted mask for the particular row being processed. If the binary AND is all zeros, the aligned capillary element(s) is/are contacted with and/or draw(s) material from the material site corresponding to the CC and CR as shown at step 106. Thereafter, in step 108, the CMCR is updated by taking the binary OR of the CMCR and the CCEM. At step 110, the program next determines whether the CC corresponds to the last column in the particular row (i.e., whether the end of the current row has been reached). Note, that if the binary AND of the CCEM (e.g., the initial or last updated CCEM) and the CMCR is not all zeros in step 104, the program proceeds directly to step 110.

If the end of the row has not been reached, the process proceeds to step 112 in which the CCEM is updated by shifting the CCEM one bit to the right (i.e., CC=CC+1) and the process leads back to step 104 to determine whether the binary AND of the last updated CCEM and the last updated CMCR is all zeros. As indicated above, if it is all zeros, the process proceeds to step 106; otherwise, the process proceeds directly to step 110. At the end of a row, the process leads to step 114, which determines whether the CR corresponds to the last row of the array (i.e., whether the last row has been reached). If the last material site in the last row is reached for the given array of materials, then the process is complete. Otherwise, the capillary elements are shifted to the next highest row (i.e., CR=CR+1) at CC=0 in step 116 and the process leads back to step 104 (i.e., whether the binary AND of the last updated CCEM and the last updated CMCR is all zeros).

Figure 2:
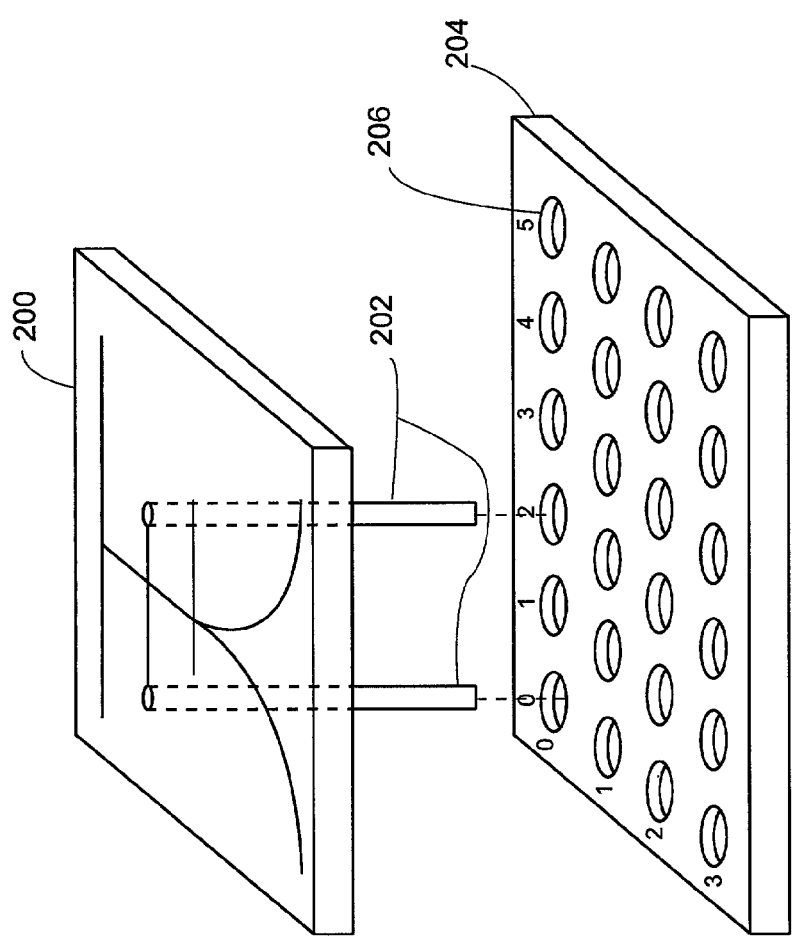
FIG. 2 schematically depicts a microfluidic device having two capillary elements and a microwell plate.

The computer implemented methods of sampling arrayed materials according to the present invention is further illustrated by considering the processing of a hypothetical microwell plate. FIG. 2 schematically depicts microfluidic device 200, which includes a two capillary element configuration with a single well spacing between pair of capillary elements 202. As also shown, microwell plate 204 includes 24 wells 206 arranged in 4 rows of 6 columns. As described above, inputted initial parameters might include, a binary CEM for pair of capillary elements 202, such 101000, where each digit corresponds to a well in a row (here, row 0). Additionally, 1 indicates the presence of a capillary element at that position, whereas 0 indicates the absence of a capillary element at that position in the CEM. Other inputted initial parameters typically include, e.g., a number of rows (here 4 (0–3)), a number of columns (here 6 (0–5)), and a mask for each row. For example, initial row masks for rows 0–3 of microwell plate 204 might be 000011, 100001, 100001, and 110000, respectively, where each bit corresponds to a well (i.e., a material site) in the particular row, and where 1 indicates that the particular material site is not to be visited, while 0 indicates that the site is to be visited. Thus, for example, the initial mask for row 0 of 000011 indicates that the first four wells in the row are selected for visitation and the last two wells in the row are deselected (i.e., not to be visited). The binary representation of the initial mask for all wells of the microwell plate (i.e., the initial array mask) is schematically depicted in FIG. 3A.

In this illustration, the processing of row 0 by pair of capillary elements 202 of microfluidic device 200, according to methods described herein (see, e.g., FIG. 1, which is discussed above), is depicted in Table 1.

TABLE 1

| CR | CC | CMCR | CCEM | AND of CMCR and CCEM | Visit? | OR of CMCR and CCEM |
|---|---|---|---|---|---|---|
| 0 | 0 | 000011 | 101000 | 000000 | Yes | 101011 |
| 0 | 1 | 101011 | 010100 | 000000 | Yes | 111111 |
| 0 | 2 | 111111 | 001010 | 001010 | No | 111111 |
| 0 | 3 | 111111 | 000101 | 000101 | No | 111111 |
| 0 | 4 | 111111 | 000010 | 000010 | No | 111111 |
| 0 | 5 | 111111 | 000001 | 000001 | No | 111111 |

As shown, each well in row 0 is systematically processed by taking the binary AND of the CMCR and CCEM to determine whether to visit the well at the CR and CC and then updating parameters, such as the CMCR, if the well at the CR and CC is visited and/or the CCEM. As shown, the updated CMCR (i.e., the binary OR of CMCR and CCEM) from the preceding CR/CC (i.e., well) corresponds to the CMCR for the next CR/CC in the particular row. The binary representation of the mask for all wells of the microwell plate (i.e., the array mask) after the processing of row 0 is schematically depicted in FIG. 3B.

The processing of row 1 is depicted in Table 2.

TABLE 2

| CR | CC | CMCR | CCEM | AND of CMCR and CCEM | Visit? | OR of CMCR and CCEM |
|---|---|---|---|---|---|---|
| 1 | 0 | 100001 | 101000 | 100000 | No | 100001 |
| 1 | 1 | 100001 | 010100 | 000000 | Yes | 110101 |
| 1 | 2 | 110101 | 001010 | 000000 | Yes | 111111 |
| 1 | 3 | 111111 | 000101 | 000101 | No | 111111 |
| 1 | 4 | 111111 | 000010 | 000010 | No | 111111 |
| 1 | 5 | 111111 | 000001 | 000001 | No | 111111 |

The binary representation of the mask for all wells of the microwell plate (i.e., the array mask) after the processing of row 1 is schematically depicted in FIG. 3C.

The processing of row 2 is depicted in Table 3.

TABLE 3

| CR | CC | CMCR | CCEM | AND of CMCR and CCEM | Visit? | OR of CMCR and CCEM |
|---|---|---|---|---|---|---|
| 2 | 0 | 100001 | 101000 | 100000 | No | 100001 |
| 2 | 1 | 100001 | 010100 | 000000 | Yes | 110101 |
| 2 | 2 | 110101 | 001010 | 000000 | Yes | 111111 |
| 2 | 3 | 111111 | 000101 | 000101 | No | 111111 |
| 2 | 4 | 111111 | 000010 | 000010 | No | 111111 |
| 2 | 5 | 111111 | 000001 | 000001 | No | 111111 |

The binary representation of the mask for all wells of the microwell plate (i.e., the array mask) after the processing of row 2 is schematically depicted in FIG. 3D.

The processing of row 3 is depicted in Table 4.

TABLE 4

| CR | CC | CMCR | CCEM | AND of CMCR and CCEM | Visit? | OR of CMCR and CCEM |
|---|---|---|---|---|---|---|
| 3 | 0 | 110000 | 101000 | 100000 | No | 110000 |
| 3 | 1 | 110000 | 010100 | 010000 | No | 110000 |
| 3 | 2 | 110000 | 001010 | 000000 | Yes | 111010 |
| 3 | 3 | 111010 | 000101 | 000000 | Yes | 111111 |
| 3 | 4 | 111111 | 000010 | 000010 | No | 111111 |
| 3 | 5 | 111111 | 000001 | 000001 | No | 111111 |

The binary representation of the mask for all wells of the microwell plate (i.e., the array mask) after the processing of row 3 is schematically depicted in FIG. 3E.

A. COMPUTER IMPLEMENTED METHODS FOR REDUCING FLUID CARRYOVER

Figure 4:
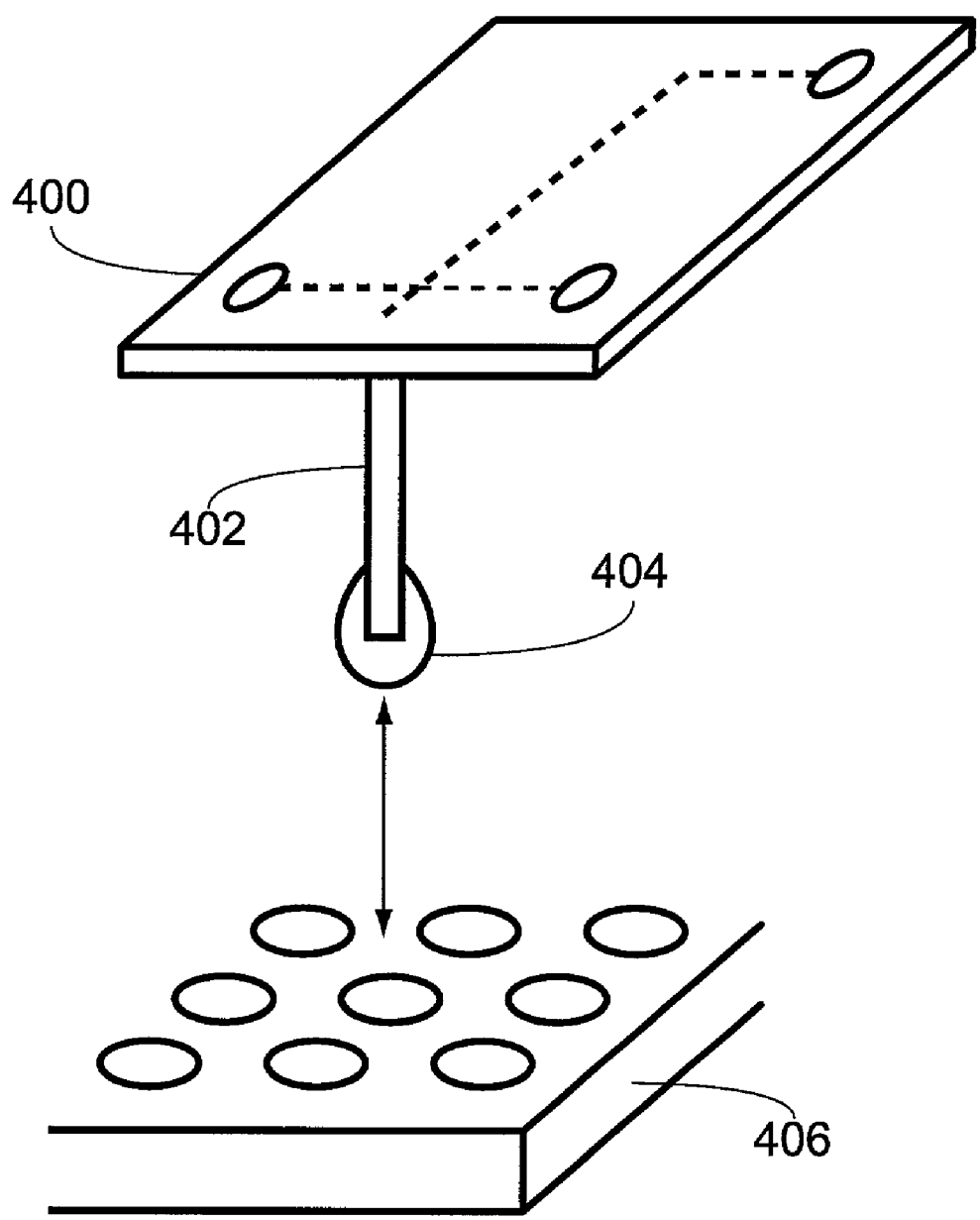
FIG. 4 schematically depicts a microfluidic device with a drop of fluid adhering to the tip region of a capillary element and a microwell plate.

One problem associated with sampling multiple materials occurs when a drop of fluid clings to the tip region of a capillary element between dipping or sampling steps which leads to fluid being carried over, e.g., from one material site to another, thus resulting in cross-contamination among material sites. As depicted in FIG. 4, capillary element 402 fluidly communicates with a microchannel network disposed within body structure 400. Although not shown, microfluidic devices optionally include more than one capillary element (e.g., 2, 3, 4, 5, 6, 7, 8, 10, 11, 12 or more elements). See, e.g., FIG. 2. During operation, capillary element 402 is typically sequentially dipped into multiple materials including, e.g., buffers, reagents, samples, and other solutions contained, e.g., in the wells of microwell plate 406 or another type of array. This type of contamination is typically caused by drop 404 that adheres both to the bottom tip of capillary element 402 and to a portion of the exterior surface of capillary element 402 when capillary element 402 is withdrawn from, e.g., the particular solution and dipped into a different solution. Drop 404 typically forms when attractive forces among component material molecules (i.e., cohesion) are less than attractive forces between component material molecules and component capillary element molecules (i.e., adhesion). The consequences of fluid carryover include biased results upon assay detection, such as reagent tailing, which limits microfluidic device throughput.

In certain embodiments, the process of sampling multiple reagents or other solutions optionally includes dipping capillary elements into buffer solutions between reagent sampling steps. During these intervening steps, a quantity of buffer solution is frequently drawn into the device, e.g., to function as a "spacer" between different reagent or sample portions. In this process, a drop of, e.g., the sample or reagent solution is typically carried over from the preceding dipping step into the intervening buffer solution. A significant problem related to this carried-over drop is that, in the absence of buffer and/or capillary element movement, carried-over drops are not completely dispersed in the buffer solution upon reinsertion of the capillary element back into the buffer solution following a subsequent sampling step. This frequently results in a non-trivial fraction of the incompletely dispersed carried-over drop(s) of previously sampled fluid(s) being drawn into spacer portions of buffer which causes biasing of results obtained in the system (e.g., the appearance of peak "shoulders" and other signal artifacts from carried-over materials). To reduce this and other fluid carryover-related problems, the present invention optionally includes reducing fluid carryover, e.g., by rinsing or washing capillary elements to dissipate fluid carryover between sampling steps (e.g., either the fluids are moved, or the capillary element is moved in the fluids, or both). Alternatively, capillary elements are coated to make them resistant to fluid carryover. Optionally, both of these approaches are utilized in conjunction. Methods and devices, including coated capillary elements, for reducing fluid carryover are described in, e.g., Published International Application No. WO 01/73396 "Methods of Reducing Fluid Carryover in Microfluidic Devices," filed Mar. 26, 2001 by Wolk et al., which is incorporated by reference in its entirety for all purposes.

In particular, the computer implemented methods of the present invention which provide for reduced fluid carryover include (a) providing a microfluidic device handling system operably connected to a computer in which the microfluidic device handling system is capable of implementing relative movement of a microfluidic device having n capillary elements extending therefrom, of an array of materials having x material sites or at least one container (e.g., recirculation/replenishing bath or trough, etc.), or of both, under instruction of the computer. The method further includes (b) inputting initial parameters for the microfluidic device and the array into the computer. The computer includes a simple logic control program for selectively contacting a capillary element and material at a selected material site disposed in or on a surface of the array. In addition, the method includes (c) implementing the simple logic control program to effect: (i) moving the microfluidic device relative to the array, the array relative to the microfluidic device, or both, according to the initial parameters, and (ii) contacting the capillary element and the material at the selected material site. Optionally, (ii) further includes drawing a selected quantity or volume of the material into the microfluidic device through the capillary element.

The method also typically includes (iii) updating the initial parameters and optionally, (iv) repeating (i), (ii), and (iii) until each selected capillary element of the microfluidic device and materials at each selected material site are contacted (e.g., sampled). The simple logic control program generally automatically directs each (i), (ii), and (iii). For example, the simple logic control program typically automatically updates the initial parameters by deselecting material at each material site contacted by the capillary element following each repeated cycle of (i) and (ii).

In certain embodiments, the material is a first fluidic material. In these embodiments, (ii) typically includes dipping the capillary element into the first fluidic material at the selected material site. Optionally, (b) further includes inputting one or more initial parameters for the container into the computer, which also includes a simple logic control program for selectively contacting the capillary element and a second fluidic material disposed in the container (e.g., recirculation/replenishing bath or trough, etc.). Additionally, (c) optionally further includes (iii) moving the microfluidic device relative to the container, the container relative to the microfluidic device, or both, according to the initial parameters or updated parameters, and (iv) dipping the capillary element into the second fluidic material, and moving the second fluidic material relative to the capillary element or moving the capillary element relative to the second fluidic material. The second fluidic material is typically disposed in at least one other selected material site of the array, or in a fluidic container distinct from the array. For example, the second fluidic material is optionally in a fluid stream or in a fluid recirculation/replenishing bath or trough. In one embodiment, (iv) further includes moving both the capillary element and the second fluid material simultaneously relative to one another. The second fluid material typically includes a solution, such as a wash solution, a rinse solution, a buffer solution, a reagent solution, a sample solution, a spacer solution, or the like. A further option includes, (v) moving the microfluidic device relative to the array, the array relative to the microfluidic device, or both, according to the initial parameters or the updated parameters, and (vi) dipping the capillary element into a third fluidic material at at least one other selected material site in which (iv) dissipates a drop of the first fluidic material adhering to a portion of the capillary element into the second fluidic material, thus reducing fluid carryover from (ii) to (vi). In other embodiments, (ii) further includes drawing a portion of the first fluidic material into the capillary element. In another embodiment, (iv) further includes drawing a portion of the second fluidic material into the capillary element. In these embodiments, (iv) typically dissipates carried-over first fluidic material in the second fluidic material thus reducing an amount of the carried-over first fluidic material drawn into the capillary element.

The simple logic control program generally optimizes a course for selectively contacting (e.g., sampling or drawing material from the material site) the capillary element and the material at the selected material site. For example, the simple logic control program includes an instruction set for causing the computer to effect movement of the microfluidic device to the selected material site or to the container (e.g., recirculation/replenishing bath or trough, etc.), to effect movement of the array or the container (e.g., recirculation/replenishing bath or trough, etc.) relative to the microfluidic device, or both; an instruction set for causing the computer to effect contact of the capillary element and the material at the selected material site or fluidic material in the at least one container (e.g., recirculation/replenishing bath or trough, etc.); and an instruction set for causing the computer to effect deselection of the selected material site following (ii). The simple logic control program also typically includes an instruction set for causing the computer to effect drawing of selected quantities or volumes of the material from the selected material site during (ii), to effect drawing of one or more selected volumes of fluidic material from the at least one container (e.g., recirculation/replenishing bath or trough, etc.), or both and/or an instruction set for causing the computer to vary or select a rate or a mode of moving or contacting the capillary element and the material or fluidic material in the at least one container (e.g., recirculation/replenishing bath or trough, etc.).

Figure 5:
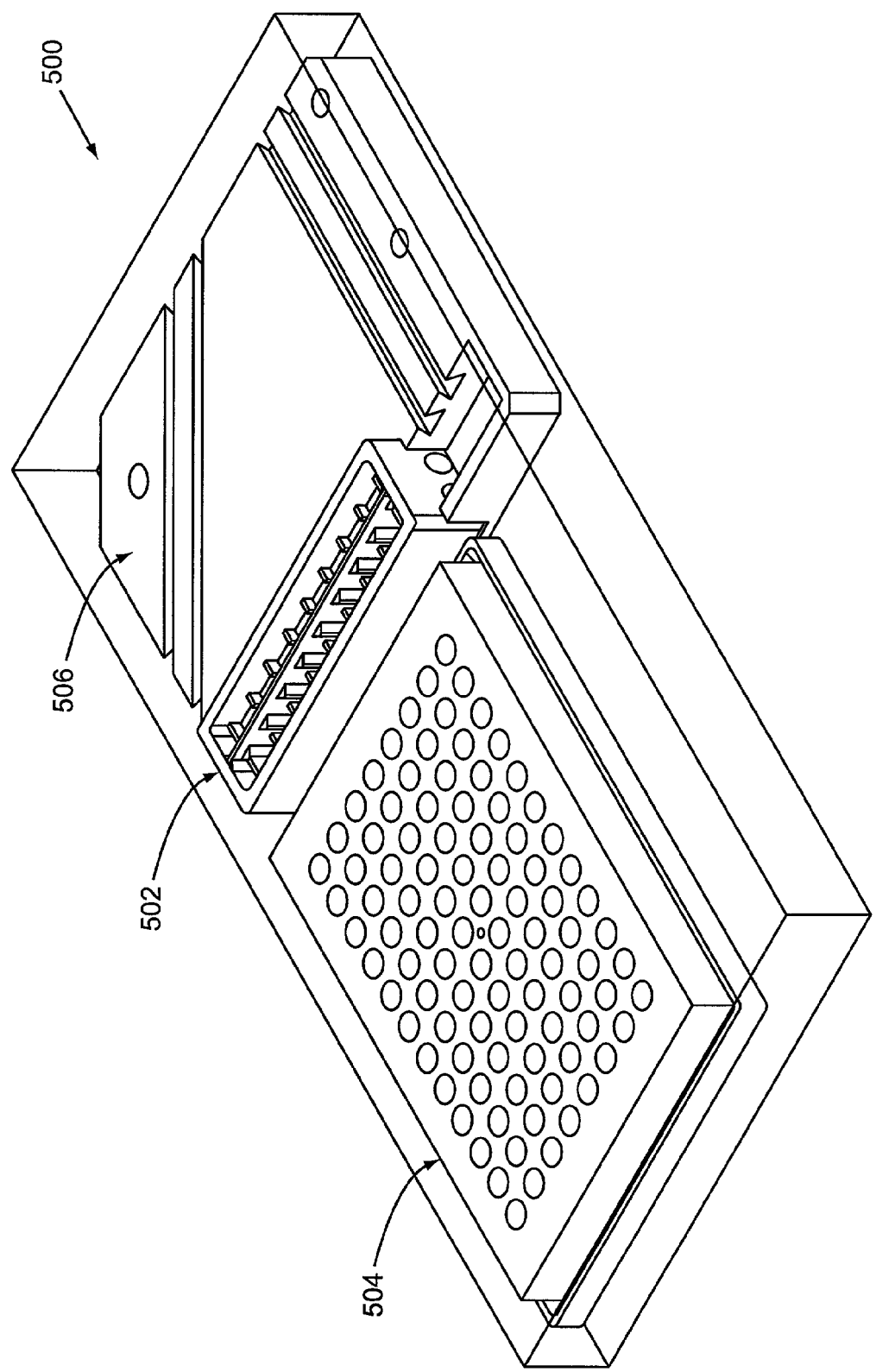
FIG. 5 schematically illustrates the assembly of certain component parts for one embodiment of a container sampling region of a microfluidic device handling system which includes a recirculation/replenishing bath or trough.

FIG. 5 schematically illustrates the assembly of certain component parts for one embodiment of a container sampling region which is optionally used, e.g., in high-throughput screening as one part of a microfluidic device handling system. These systems are described in greater detail below. As shown, sampling region 500 includes fluid trough 502, microwell plate 504, and pump/trough interface region or "shoe" 506. Fluidic materials (e.g., buffers, dyes, or the like) are optionally contained and recirculated or replenished in fluid trough 502. This generally enhances throughput, because these types of fluidic materials are not carried on microwell plate 504, thus leaving additional wells open for more samples. As mentioned, flow rates and turbulence of fluidic materials in fluid trough 502 are also optionally varied to reduce fluid carryover, e.g., between sampling steps. Optionally, fluid trough 502, itself, is moved relative to a particular microfluidic device while dipped into the trough to minimize carryover. Fluid trough 502 is designed to resist splashing during the motion of microwell plate 504, e.g., when it is replaced with another sample plate. As shown in this embodiment, fluid trough 502 includes two banks, each of which is fluidly connected to a separate pump (not shown).

III. Microfluidic Device Handlers and Other Integrated System Components

The present invention also relates to an integrated system that includes a computer and a microfluidic device handling system operably connected to the computer. The microfluidic device handling system is capable of implementing relative movement of a microfluidic device having n capillary elements extending therefrom, of an array of materials having x material sites or a container (e.g., recirculation/replenishing bath or trough, etc.), or of both, under instruction of the computer. The integrated system also includes a computer readable medium operably connected to the computer that stores a simple logic control program for selectively contacting a capillary element and a material at a selected material site disposed in or on a surface of the array or a fluid in the container. The computer readable medium typically includes, e.g., a CD-ROM, a floppy disk, a tape, a flash memory device or component, a system memory device or component, a magnetic storage medium, such as a hard drive, a data signal embodied in a carrier wave, or the like.

The initial parameters or the updated parameters generally include, e.g., an n-value, an x-value, a capillary element mask, an array mask, a number of columns of material sites, a number of rows of material sites, a mask for each row of material sites, a selection of materials at material sites to be contacted, a quantity or volume of the material to be drawn from the at least one selected material site, a deselection of materials at material sites not to be contacted, or the like.

The integrated systems of the invention are capable of accommodating essentially any number or combination of microfluidic device capillary elements and arrayed materials sites. For example, n typically corresponds to at least about 1, 2, 4, 6, 8, 12, or more capillary elements, whereas x typically corresponds to at least about 1, 10, 50, 96, 250, 384, 500, 1000, 1536, 5000, 10000, 100000, or more material sites. In addition, the array generally includes a microwell plate, substrate, or membrane. To illustrate, the x material sites optionally correspond to x wells in the microwell plate, or to x sample sites on the substrate or membrane.

The invention, in addition to other integrated system components, also provides a microfluidic device handling system for performing the methods disclosed herein. Specifically, the microfluidic device handling system typically includes a holder configured to receive the microfluidic device, a container sampling region proximal to the holder configured to receive the array, and a controller operably connected to one or more handler components. During operation of the handling system, the controller implements movement or interchange of the microfluidic device, the array, or both, contact between the capillary element and the material, drawing or sampling of the material, and dipping of microfluidic device capillary element(s) into a portion of a container (e.g., a fluid recirculation/replenishing bath or trough or the like) in the container sampling region. The container portion typically includes a fluid material (e.g., a sample, a reagent, a buffer, or other solution), in which the controller directs movement of the fluid material relative to the capillary element(s) of the microfluidic device, and/or lateral movement of the capillary element(s) in the fluid material while the capillary element(s) is/are dipped into the fluid material.

When the microfluidic device handling system includes a fluid recirculation/replenishing bath or trough, the system also generally includes a recirculation/replenishing pump operably connected to the bath or trough. See, FIG. 5 for a schematic representation of one embodiment of a fluid recirculation/replenishing bath or trough. The recirculation/replenishing pump is typically operably connected to the fluid recirculation/replenishing bath or trough by an inlet tube and an outlet tube. Optionally, an inner diameter of the outlet tube is greater than an inner diameter of the inlet tube. This prevents fluid overflow at any rate of flow from the pump. Additionally, the recirculation/replenishing bath or trough optionally includes a plurality of compartments. Each of the plurality of compartments optionally fluidly communicates with at least one other compartment and a bottom portion of at least one of the plurality of compartments optionally includes a fluid inlet.

The microfluidic device handling system also optionally includes a computer or a computer readable medium operably connected to the controller. The computer or the computer readable medium typically includes an instruction set for varying or selecting a rate or a mode of dipping capillary element(s) into fluid materials. For example, the mode of dipping the capillary element(s) optionally includes one or more movements relative to the fluid materials, such as a lateral motion, a side-to-side motion, a circular motion, a semi-circular motion, a helical motion, an arched motion, an up-and-down motion, and/or the like. The computer or the computer readable medium also optionally includes an instruction set for varying or selecting a rate or a mode with which the fluid material moves relative to the microfluidic device in, e.g., a recirculation/replenishing bath or trough. The mode with which the fluid material moves optionally includes, e.g., a fluid stream, a lateral motion, a side-to-side motion, a circular motion, a semi-circular motion, a helical motion, an arched motion, or the like.

Figure 6:
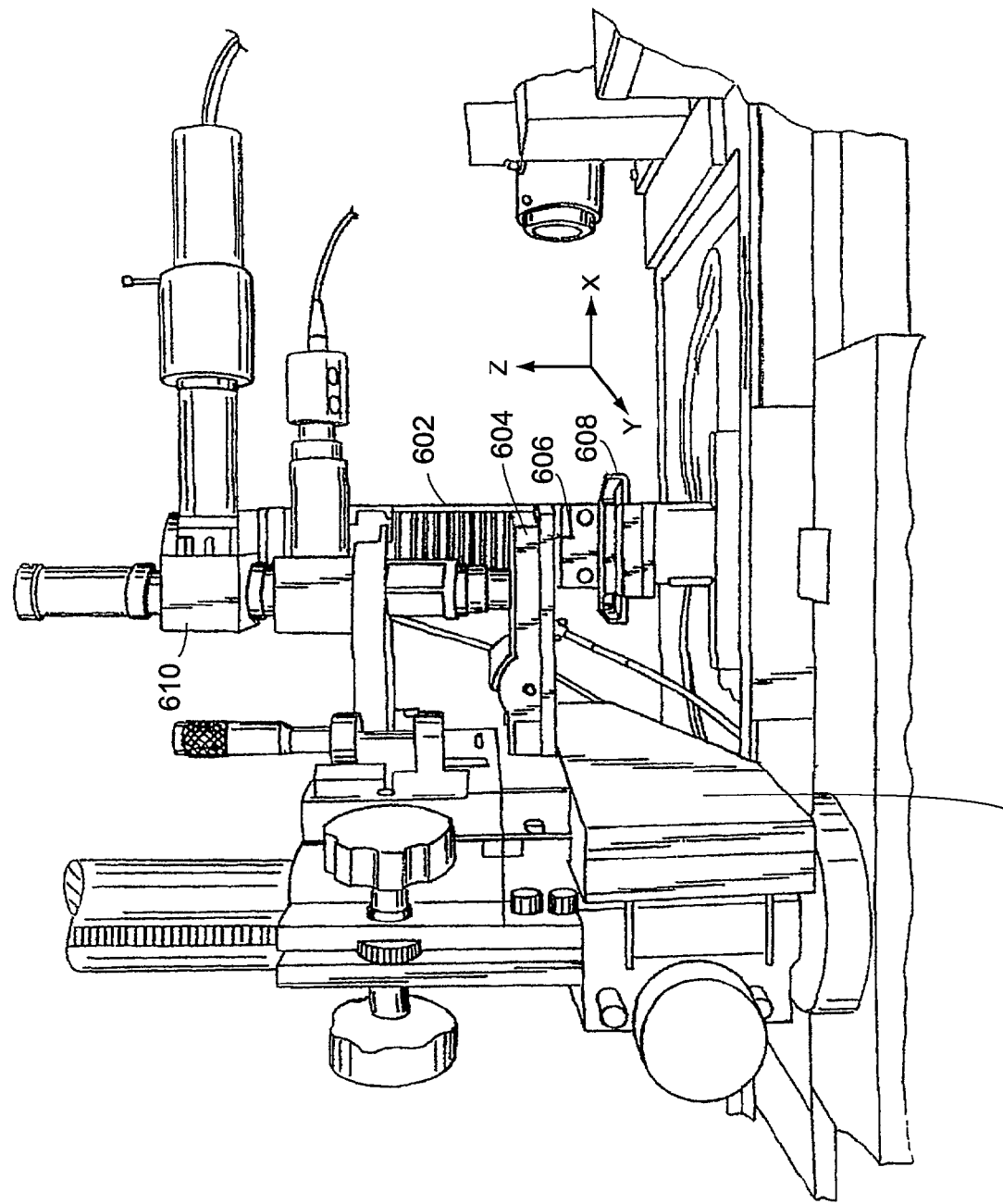
FIG. 6 schematically depicts one embodiment of certain components of a microfluidic device handling system.

FIG. 6 schematically illustrates the structure and arrangement of certain components of one embodiment of a microfluidic device handling system. As shown, the system includes microfluidic device X-Y-Z robotic arm 600 and array X-Y-Z robotic arm 602 for moving microfluidic devices and arrays of materials relative to one another. Microfluidic device X-Y-Z robotic arm 600 includes microfluidic device holder 604 which contains a microfluidic device. As shown, capillary element 606 extends downward from the microfluidic device and microfluidic device holder 604. Array X-Y-Z robotic arm 602 includes container sampling region 608 in which an array such as a n-microwell plate is typically disposed (not shown) for translational movement relative to the microfluidic device. Also shown is optical detection system 610 which, e.g., optically monitors assays within the microchannel network of the microfluidic device. Additional details relating to microfluidic device handling systems are included in, e.g., U.S. Pat. No. 6,132,685 "High Throughput Microfluidic Systems and Methods" issued Oct. 17, 2000 to Kersco et al., which is incorporated by reference in its entirety for all purposes.

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations in addition to the operations specifically described herein. Aside from sampling arrayed materials, other upstream or downstream operations include, e.g., particle separation, extraction, purification, amplification, cellular activation, labeling reactions, dilution, aliquotting, separation of sample components, labeling of components, assays and detection operations, electrokinetic or pressure-based injection of components into contact with particle sets, or materials released from particle sets, or the like.

Assay and detection operations include, without limitation, cell fluorescence assays, cell activity assays, probe interrogation assays, e.g., nucleic acid hybridization assays utilizing individual probes, free or tethered within the channels or chambers of the device and/or probe arrays having large numbers of different, discretely positioned probes, receptor/ligand assays, immunoassays, and the like. Any of these elements are optionally fixed to array members, or fixed, e.g., to channel walls, or the like.

In the present invention, the materials are optionally monitored and/or detected so that, e.g., an activity can be determined. The systems described herein generally include microfluidic device handling systems, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions (e.g., the computer implemented methods of the present invention), receiving data from the detection instrumentation, and for analyzing, storing and interpreting the data, and providing the data and interpretations in a readily accessible reporting format.

A. Controllers

The controllers of the integrated systems of the present invention direct dipping of capillary elements into, e.g., microwell plates or other arrays to sample reagents, such as enzymes and substrates, fluid recirculation/replenishing baths or troughs, or the like. A variety of controlling instrumentation is also optionally utilized in conjunction with the microfluidic devices and handling systems described herein, for controlling the transport, concentration, direction, and motion of fluids and/or separation of materials within the devices of the present invention, e.g., by pressure-based control.

As described above, in many cases, fluid transport, concentration, and direction are controlled in whole or in part, using pressure based flow systems that incorporate external or internal pressure sources to drive fluid flow. Internal sources include microfabricated pumps, e.g., diaphragm pumps, thermal pumps, and the like that have been described in the art. See, e.g., U.S. Pat. Nos. 5,271,724, 5,277,556, and 5,375,979 and Published International Application Nos. WO 94/05414 and WO 97/02357. Preferably, external pressure sources are used, and applied to ports at channel termini. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or preferably, by applying a single vacuum at a common waste port and configuring the various channels with appropriate resistance to yield desired flow rates. Example systems are also described in U.S. Ser. No. 09/238,467, filed Jan. 28, 1999.

Typically, the controller systems are appropriately configured to receive or interface with a microfluidic device or system element as described herein. For example, the controller and/or detector, optionally includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

The controlling instrumentation discussed above is also used to provide for electrokinetic injection or withdrawal of material downstream of the region of interest to control an upstream flow rate. The same instrumentation and techniques described above are also utilized to inject a fluid into a downstream port to function as a flow control element.

B. Detectors

The devices described herein optionally include signal detectors, e.g., which detect concentration, fluorescence, phosphorescence, radioactivity, pH, charge, absorbance, refractive index, luminescence, temperature, magnetism, mass (e.g., mass spectrometry), or the like. The detector(s) optionally monitors one or a plurality of signals from upstream and/or downstream (e.g., in or proximal to the separation region) of an assay mixing point in which, e.g., a ligand and an enzyme or the like are mixed. For example, the detector optionally monitors a plurality of optical signals which correspond in position to "real time" assay/separation results.

Example detectors or sensors include photomultiplier tubes, CCD arrays, optical sensors, temperature sensors, pressure sensors, pH sensors, conductivity sensors, mass sensors, scanning detectors, or the like. Materials which emit a detectable signal are optionally flowed past the detector, or, alternatively, the detector can move relative to the array to determine the position of an assay component (or, the detector can simultaneously monitor a number of spatial positions corresponding to channel regions, e.g., as in a CCD array). Each of these types of sensors is optionally readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. The detector optionally includes or is operably linked to a computer, e.g., which has software for converting detector signal information into assay result information (e.g., kinetic data of modulator activity), or the like. A microfluidic system optionally employs multiple different detection systems for monitoring the output of the system. Detection systems of the present invention are used to detect and monitor the materials in a particular channel region (or other reaction detection region).

The detector optionally exists as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector, and the computer.

C. Computer Systems

As noted above, the microfluidic devices and integrated systems of the present invention include a computer operably connected to, e.g., the microfluidic device handling system/controller. The computer typically includes an instruction set, e.g., for varying or selecting a rate or a mode of contacting capillary elements and arrayed materials, for sampling arrayed materials, or the like. Additionally, either or both of the controller system and/or the detection system is/are optionally coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

As will be understood by practitioners in the art from the teachings provided herein, the invention is optionally implemented in hardware and/or software. In some embodiments, different aspects of the invention are implemented in either client-side logic or server-side logic. As will also be understood in the art, the invention or components thereof may be embodied in a media program component (e.g., a fixed media component) containing logic instructions (e.g., instruction sets, etc.) and/or data that, when loaded into an appropriately configured computing device, cause that device to perform according to the invention. As will additionally be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

Figure 7:
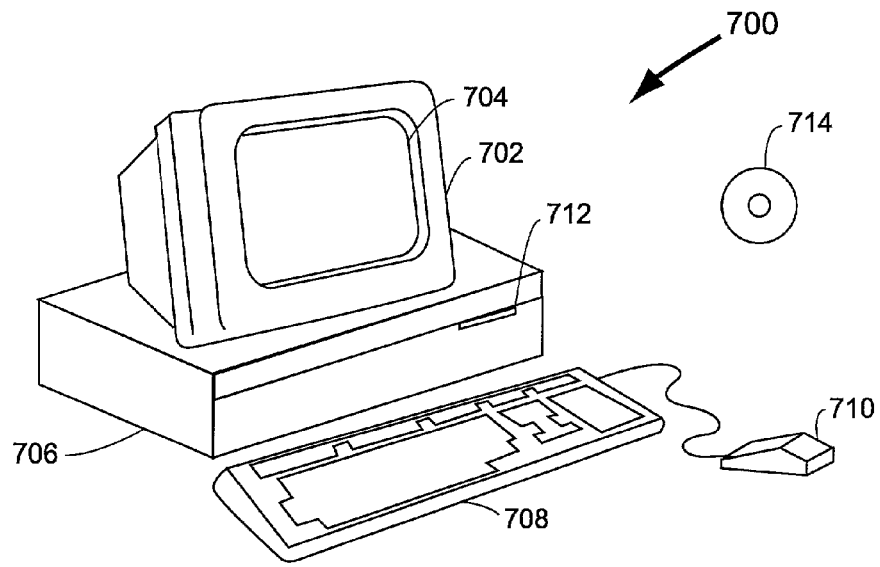
FIG. 7 schematically illustrates an example of a computer system that is optionally used to execute the software of embodiments of the invention.

FIG. 7 schematically illustrates an example of a computer system that is optionally used to execute the software of embodiments of the present invention. As shown, FIG. 7 includes system 700 which includes output display 702, display screen 704, cabinet 706, keyboard 708, and mouse 710. Mouse 710 typically includes one or more buttons for interacting with a graphical user interface (GUI). Cabinet 706 houses CD-ROM drive 712, system memory and a hard drive (see FIG. 8) which may be utilized to store and retrieve software programs incorporating computer instruction sets that implement the methods of the present invention, inputted and/or updated parameters, data for use with the invention, or the like. Although CD-ROM 714 is shown as an exemplary computer readable storage medium, other computer readable storage media including floppy disks, tapes, flash memory, system memory, and hard drives are optionally utilized. Additionally, a data signal embodied in a carrier wave (e.g., in a network including the Internet) is optionally utilized as the computer readable storage medium.

Figure 8:
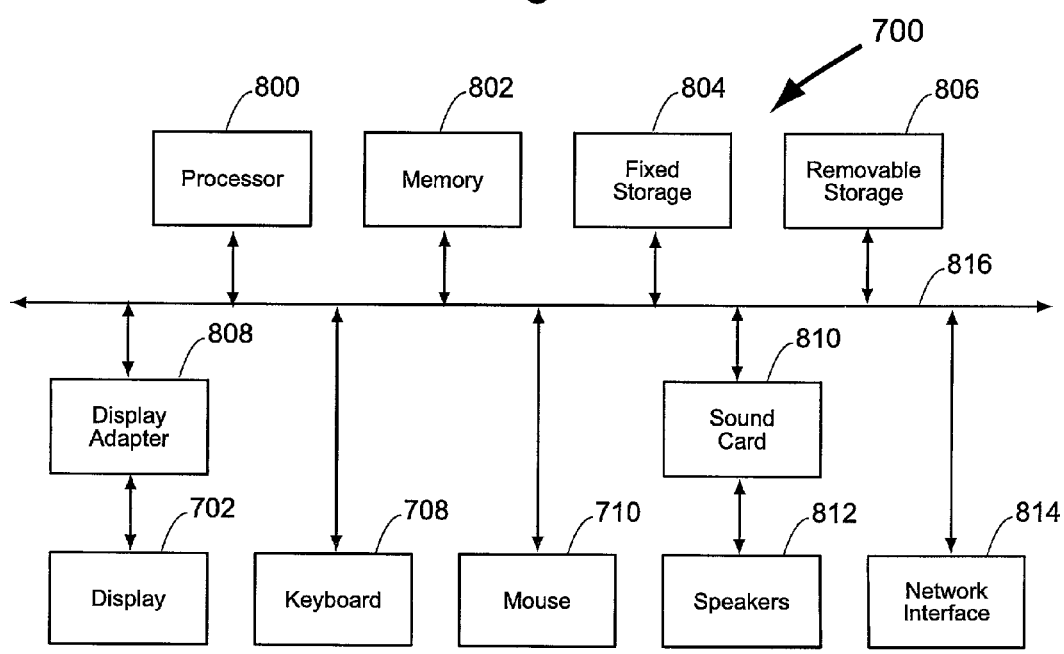
FIG. 8 depicts a system block diagram of an example computer system used to execute the software of embodiments of the invention.

FIG. 8 depicts a system block diagram of system 700 used to execute the software of embodiments of the present invention. As in FIG. 7, system 700 includes output display 702, keyboard 708, and mouse 710. System 700 also includes subsystems such as central processor 800, system memory 802, fixed storage 804 (e.g., a hard drive), removable storage 806 (e.g., a CD-ROM drive), display adapter 808, sound card 810, speakers 812, and network interface 814. Other computer systems suitable for use with the invention optionally include additional or fewer subsystems. For example, another computer system may include more than one processor 800 (i.e., a multi-processor system) and/or cashe memory.

The system bus architecture of system 700 is represented by arrows 816. However, these arrows are illustrative of any interconnection scheme serving to link the subsystems. For example, a local bus could be utilized to connect central processor 800 to system memory 802 and display adapter 808. System 700 shown in FIG. 8 is only one example of a computer system suitable for use with the invention. Other computer architectures having different configurations of subsystems may also be utilized.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of, e.g., the fluid direction and transport controller to carry out the desired operation, e.g., varying or selecting the rate or mode of fluid and/or microfluidic device movement, controlling flow rates within microscale channels, directing X-Y-Z translation of the microfluidic device or of one or more microwell plates or other arrays, or the like. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like. Additionally, the software is optionally used to control, e.g., pressure or electrokinetic modulated injection or withdrawal of material.

D. Example Integrated System

Figure 9:
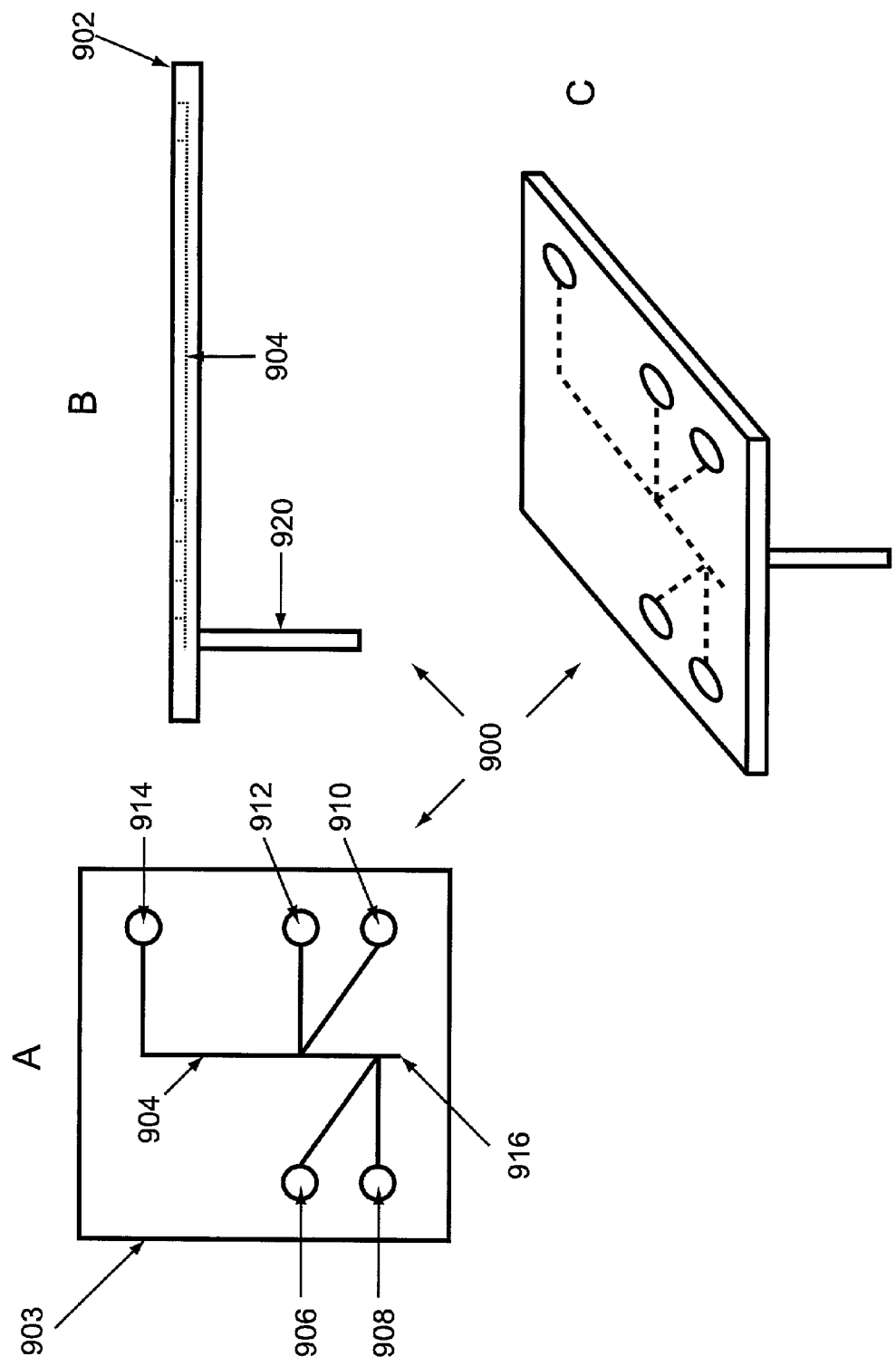
FIGS. 9A–9C schematically show a microfluidic device that includes a capillary element from various viewpoints.

FIG. 9, Panels A, B, and C and FIG. 10 provide additional details regarding example integrated systems that are optionally used to practice the methods herein. As shown, body structure 902 of microfluidic device 900 has main microchannel 904 disposed therein. A sample or other material is optionally flowed from pipettor or capillary element 920 towards reservoir 914, e.g., by applying a vacuum at reservoir 914 (or another point in the system) and/or by applying appropriate voltage gradients. Alternatively, a vacuum is applied at reservoirs 908, 912 or through pipettor or capillary element 920. Additional materials, such as buffer solutions, substrate solutions, enzyme solutions, and the like, as described above are optionally flowed from wells 908 or 912 and into main microchannel 904. Flow from these wells is optionally performed by modulating fluid pressure, or by electrokinetic approaches as described (or both). As fluid is added to main microchannel 904, e.g., from reservoir 908, the flow rate increases. The flow rate is optionally reduced by flowing a portion of the fluid from main microchannel 904 into flow reduction microchannel 906 or 910. The arrangement of channels depicted in FIG. 9 is only one possible arrangement out of many which are appropriate and available for use in the present invention. Additional alternatives can be devised, e.g., by combining the microfluidic elements described herein, e.g., mixing regions, separation regions, or the like, with other microfluidic device components described in the patents and applications referenced herein.

Samples or other materials are optionally flowed from the enumerated wells or from a source external to the body structure. As depicted, the integrated system optionally includes pipettor or capillary element 920, e.g., protruding from body 902, for accessing a source of materials external to the microfluidic system. Typically, the external source is a microtiter dish, a substrate, a membrane, or other convenient storage medium. For example, as depicted in FIG. 10, pipettor or capillary element 920 can access microwell plate 1008, which includes sample materials, buffers, substrate solutions, enzyme solutions, or the like, in the wells of the plate.

Detector 1006 is in sensory communication with main microchannel 904, detecting signals resulting, e.g., from labeled materials flowing through the detection region. Detector 1006 is optionally coupled to any of the channels or regions of the device where detection is desired. Detector 1006 is operably linked to computer 1004, which digitizes, stores, and manipulates signal information detected by detector 1006, e.g., using any instruction set, e.g., for determining concentration, molecular weight or identity, or the like.

Fluid direction system 1002 controls pressure, voltage, or both, e.g., at the wells of the system or through the channels of the system, or at vacuum couplings fluidly coupled to main microchannel 904 or other channels described above. Optionally, as depicted, computer 1004 controls fluid direction system 1002. In one set of embodiments, computer 1004 uses signal information to select further parameters for the microfluidic system. For example, upon detecting the presence of a component of interest (e.g., following separation) in a sample from microwell plate 1008, the computer optionally directs addition of a potential modulator of the component of interest into the system. In certain embodiments, controller 1010 dispenses aliquots of selected material into, e.g., main microchannel 904. In these embodiments, controller 1010 is also typically operably connected to computer 1004, which directs controller 1010 function.

Although not shown, a microfluidic device handling system is also included in the integrated systems of the present invention. Microfluidic device handling systems generally control, e.g., the X-Y-Z translation of microfluidic device 900 relative to microwell plate 908, of microwell plate 908 relative to microfluidic device 900, or of other system components, under the direction of computer 1004, e.g., according to the simple logic control programs herein, to which device handling systems are typically operably connected.

IV. Microfluidic Devices

Many different microscale systems are optionally adapted for use in the material contacting or sampling methods of the present invention. These systems are described in numerous publications by the inventors and their coworkers, including certain issued U.S. patents, such as U.S. Pat. No. 5,699,157 (J. Wallace Parce) issued Dec. 16, 1997, U.S. Pat. No. 5,779,868 (J. Wallace Parce et al.) issued Jul. 14, 1998, U.S. Pat. No. 5,800,690 (Calvin Y. H. Chow et al.) issued Sep. 1, 1998, U.S. Pat. No. 5,842,787 (Anne R. Kopf-Sill et al.)

issued Dec. 1, 1998, U.S. Pat. No. 5,852,495 (J. Wallace Parce) issued Dec. 22, 1998, U.S. Pat. No. 5,869,004 (J. Wallace Parce et al.) issued Feb. 9, 1999, U.S. Pat. No. 5,876,675 (Colin B. Kennedy) issued Mar. 2, 1999, U.S. Pat. No. 5,880,071 (J. Wallace Parce et al.) issued Mar. 9, 1999, U.S. Pat. No. 5,882,465 (Richard J. McReynolds) issued Mar. 16, 1999, U.S. Pat. No. 5,885,470 (J. Wallace Parce et al.) issued Mar. 23, 1999, U.S. Pat. No. 5,942,443 (J. Wallace Parce et al.) issued Aug. 24, 1999, U.S. Pat. No. 5,948,227 (Robert S. Dubrow) issued Sep. 7, 1999, U.S. Pat. No. 5,955,028 (Calvin Y. H. Chow) issued Sep. 21, 1999, U.S. Pat. No. 5,957,579 (Anne R. Kopf-Sill et al.) issued Sep. 28, 1999, U.S. Pat. No. 5,958,203 (J. Wallace Parce et al.) issued Sep. 28, 1999, U.S. Pat. No. 5,958,694 (Theo T. Nikiforov) issued Sep. 28, 1999, U.S. Pat. No. 5,959,291 (Morten J. Jensen) issued Sep. 28, 1999, U.S. Pat. No. U.S. Pat. No. 5,964,995 (Theo T. Nikiforov et al.) issued Oct. 12, 1999, U.S. Pat. No. 5,965,001 (Calvin Y. H. Chow et al.) issued Oct. 12, 1999, U.S. Pat. No. 5,965,410 (Calvin Y. H. Chow et al.) issued Oct. 12, 1999, U.S. Pat. No. 5,972,187 (J. Wallace Parce et al.) issued Oct. 26, 1999, U.S. Pat. No. 5,976,336 (Robert S. Dubrow et al.) issued Nov. 2, 1999, U.S. Pat. No. 5,989,402 (Calvin Y. H. Chow et al.) issued Nov. 23, 1999, U.S. Pat. No. 6,001,231 (Anne R. Kopf-Sill) issued Dec. 14, 1999, U.S. Pat. No. 6,011,252 (Morten J. Jensen) issued Jan. 4, 2000, U.S. Pat. No. 6,012,902 (J. Wallace Parce) issued Jan. 11, 2000, U.S. Pat. No. 6,042,709 (J. Wallace Parce et al.) issued Mar. 28, 2000, U.S. Pat. No. 6,042,710 (Robert S. Dubrow) issued Mar. 28, 2000, U.S. Pat. No. 6,046,056 (J. Wallace Parce et al.) issued Apr. 4, 2000, U.S. Pat. No. 6,048,498 (Colin B. Kennedy) issued Apr. 11, 2000, U.S. Pat. No. 6,068,752 (Robert S. Dubrow et al.) issued May 30, 2000, U.S. Pat. No. 6,071,478 (Calvin Y. H. Chow) issued Jun. 6, 2000, U.S. Pat. No. 6,074,725 (Colin B. Kennedy) issued Jun. 13, 2000, U.S. Pat. No. 6,080,295 (J. Wallace Parce et al.) issued Jun. 27, 2000, U.S. Pat. No. 6,086,740 (Colin B. Kennedy) issued Jul. 11, 2000, U.S. Pat. No. 6,086,825 (Steven A. Sundberg et al.) issued Jul. 11, 2000, U.S. Pat. No. 6,090,251 (Steven A. Sundberg et al.) issued Jul. 18, 2000, U.S. Pat. No. 6,100,541 (Robert Nagle et al.) issued Aug. 8, 2000, U.S. Pat. No. 6,107,044 (Theo T. Nikiforov) issued Aug. 22, 2000, U.S. Pat. No. 6,123,798 (Khushroo Gandhi et al.) issued Sep. 26, 2000, U.S. Pat. No. 6,129,826 (Theo T. Nikiforov et al.) issued Oct. 10, 2000, U.S. Pat. No. 6,132,685 (Joseph E. Kersco et al.) issued Oct. 17, 2000, U.S. Pat. No. 6,148,508 (Jeffrey A. Wolk) issued Nov. 21, 2000, U.S. Pat. No. 6,149,787 (Andrea W. Chow et al.) issued Nov. 21, 2000, U.S. Pat. No. 6,149,870 (J. Wallace Parce et al.) issued Nov. 21, 2000, U.S. Pat. No. 6,150,119 (Anne R. Kopf-Sill et al.) issued Nov. 21, 2000, U.S. Pat. No. 6,150,180 (J. Wallace Parce et al.) issued Nov. 21, 2000, U.S. Pat. No. 6,153,073 (Robert S. Dubrow et al.) issued Nov. 28, 2000, U.S. Pat. No. 6,156,181 (J. Wallace Parce et al.) issued Dec. 5, 2000, U.S. Pat. No. 6,167,910 (Calvin Y. H. Chow) issued Jan. 2, 2001, U.S. Pat. No. 6,171,067 (J. Wallace Parce) issued Jan. 9, 2001, U.S. Pat. No. 6,171,850 (Robert Nagle et al.) issued Jan. 9, 2001, U.S. Pat. No. 6,172,353 (Morten J. Jensen) issued Jan. 9, 2001, U.S. Pat. No. 6,174,675 (Calvin Y. H. Chow et al.) issued Jan. 16, 2001, U.S. Pat. No. 6,182,733 (Richard J. McReynolds) issued Feb. 6, 2001, U.S. Pat. No. 6,186,660 (Anne R. Kopf-Sill et al.) issued Feb. 13, 2001, U.S. Pat. No. 6,221,226 (Anne R. Kopf-Sill) issued Apr. 24, 2001, U.S. Pat. No. 6,233,048 (J. Wallace Parce) issued May 15, 2001, U.S. Pat. No. 6,235,175 (Robert S. Dubrow et al.) issued May 22, 2001, U.S. Pat. No. 6,235,471 (Michael Knapp et al.) issued May 22, 2001, U.S. Pat. No. 6,238,538 (J. Wallace Parce et al.) issued May 29, 2001, U.S. Pat. No. 6,251,343 (Robert S. Dubrow et al.) issued Jun. 26, 2001, U.S. Pat. No. 6,267,858 (J. Wallace Parce et al.) issued Jul. 31, 2001, U.S. Pat. No. 6,274,089 (Andrea W. Chow et al.) issued Aug. 14, 2001, U.S. Pat. No. 6,274,337 (J. Wallace Parce et al.) issued Aug. 14, 2001, U.S. Pat. No. 6,287,520 (J. Wallace Parce et al.) issued Sep. 11, 2001, U.S. Pat. No. 6,287,774 (Theo T. Nikiforov) issued Sep. 11, 2001, 6,303,343 (Anne R. Kopf-Sill) issued Oct. 16, 2001, U.S. Pat. No. 6,306,590 (Tammy Burd Mehta et al.) issued Oct. 23, 2001, U.S. Pat. No. 6,306,659 (J. Wallace Parce et al.) issued Oct. 23, 2001, U.S. Pat. No. 6,316,201 (Theo T. Nikiforov) issued Nov. 13, 2001, U.S. Pat. No. 6,316,781 (Robert Nagle et al.) issued Nov. 13, 2001, U.S. Pat. No. 6,321,791 (Calvin Y. H. Chow) issued Nov. 27, 2001, and U.S. Pat. No. 6,322,683 (Jeffrey A. Wolk et al.) issued Nov. 27, 2001, which are incorporated by reference in their entirety for all purposes. Systems adapted for use with the devices of the present invention are also described in, e.g., various published international applications, including WO 98/00231, WO 98/00705, WO 98/00707, WO 98/02728, WO 98/05424, WO 98/22811, WO 98/45481, WO 98/45929, WO 98/46438, and WO 98/49548, WO 98/55852, WO 98/56505, WO 98/56956, WO 99/00649, WO 99/10735, WO 99/12016, WO 99/16162, WO 99/19056, WO 99/19516, WO 99/29497, WO 99/31495, WO 99/34205, WO 99/43432, WO 99/44217, WO 99/56954, WO 99/64836, WO 99/64840, WO 99/64848, WO 99/67639, WO 00/07026, WO 00/09753, WO 00/10015, WO 00/21666, WO 00/22424, WO 00/26657, WO 00/42212, WO 00/43766, WO 00/45172, WO 00/46594, WO 00/50172, WO 00/50642, WO 00/58719, WO 00/60108, WO 00/70080, WO 00/70353, WO 00/72016, WO 00/73799, WO 00/78454, WO 01/02850, WO 01/14865, WO 01/17797, WO 01/27253, WO 01/63270, WO 01/84242, WO 01/79522, WO 01/77683, WO 01/77641, WO 01/73417, WO 01/73396, WO 01/04619, WO 01/04617, WO 01/57509, WO 01/55711, WO 01/49414, WO 01/49874, WO 01/31322, and WO 01/14064, which are incorporated by reference in their entirety for all purposes.

The methods of the invention are generally performed within fluidic channels along which reagents, enzymes, samples, eluents, separation buffers, and other fluids are disposed and/or flowed. In some cases, as mentioned above, the channels are simply present in a capillary or pipettor element, e.g., a glass, fused silica, quartz or plastic capillary. The capillary element is fluidly coupled to a source of, e.g., the reagent, sample, modulator, or other solution (e.g., by dipping the capillary element into a well on a microtiter plate, etc.), which is then flowed along the channel (e.g., a microchannel) of the element. In preferred embodiments, the capillary element is integrated into the body structure of a microfluidic device. The term "microfluidic," as used herein, generally refers to one or more fluid passages, chambers or conduits which have at least one internal cross-sectional dimension, e.g., depth, width, length, diameter, etc., that is less than 500 µm, and typically between about 0.1 µm and about 500 µm.

In the devices of the present invention, the microscale channels or cavities typically have at least one cross-sectional dimension between about 0.1 µm and 200 µm, preferably between about 0.1 µm and 100 µm, and often between about 0.1 µm and 50 µm. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "Y" and/or "T" intersections, or any number of other structures whereby two channels are in fluid communication.

The body structures of the microfluidic devices described herein are typically manufactured from two or more separate portions or substrates which when appropriately mated or joined together, form the microfluidic device of the invention, e.g., containing the channels and/or chambers described herein. During body structure fabrication, the microfluidic devices described herein will typically include a top portion, a bottom portion, and an interior portion, wherein the interior portion substantially defines the channels and chambers of the device.

In one aspect, a bottom portion of the unfinished device includes a solid substrate that is substantially planar in structure, and which has at least one substantially flat upper surface. Channels are typically fabricated on one surface of the device and sealed by overlaying the channels with an upper substrate layer. A variety of substrate materials are optionally employed as the upper or bottom portion of the device. Typically, because the devices are microfabricated, substrate materials will be selected based upon their compatibility with known microfabrication techniques, e.g., photolithography, wet chemical etching, laser ablation, air abrasion techniques, LIGA, reactive ion etching, injection molding, embossing, and other techniques. The substrate materials are also generally selected for their compatibility with the full range of conditions to which the microfluidic devices may be exposed, including extremes of pH, temperature, electrolyte concentration, and/or for their chromatographic properties. Accordingly, in some preferred aspects, the substrate material may include materials normally associated with the semiconductor industry in which such microfabrication techniques are regularly employed, including, e.g., silica-based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLONm), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), and the like. In preferred embodiments, at least the separation region(s) is/are fabricated from polyacrylamide, dimethylacrylamide, modified versions thereof, nonionic detergents, ionic detergents, or the like. Such polymeric substrates are readily manufactured using available microfabrication techniques, as described above, or from microfabricated masters, using known molding techniques, such as injection molding, embossing or stamping, or by polymerizing the polymeric precursor material within the mold (see, e.g., U.S. Pat. No. 5,512,131). Such polymeric substrate materials are preferred for their ease of manufacture, low cost and disposability, as well as their general inertness to most extreme reaction conditions. Again, these polymeric materials optionally include treated surfaces, e.g., derivatized or coated surfaces, to enhance their utility in the microfluidic system, e.g., to provide enhanced fluid direction, e.g., as described in U.S. Pat. No. 5,885,470 (J. Wallace Parce et al.) issued Mar. 23, 1999, and which is incorporated herein by reference in its entirety for all purposes.

The channels and/or cavities of the microfluidic devices are typically fabricated into the upper surface of the bottom substrate or portion of the device, as microscale grooves or indentations, using the above described microfabrication techniques. The top portion or substrate also comprises a first planar surface, and a second surface opposite the first planar surface. In the microfluidic devices prepared in accordance with certain aspects of the methods described herein, the top portion can include at least one aperture, hole or port disposed therethrough, e.g., from the first planar surface to the second surface opposite the first planar surface. In other embodiments, the port(s) are optionally omitted, e.g., where fluids are introduced solely through external capillary elements.

The first planar surface of the top portion or substrate is then mated, e.g., placed into contact with, and bonded to the planar surface of the bottom substrate, covering and sealing the grooves and/or indentations in the surface of the bottom substrate, to form the channels and/or chambers (i.e., the interior portion) of the device at the interface of these two components. Bonding of substrates is typically carried out by any of a number of different methods, e.g., thermal bonding, solvent bonding, ultrasonic welding, and the like. The finished body structure of a device is a unitary structure that houses, e.g., the channels and/or chambers of the device.

The hole(s) in the top of the finished device is/are oriented to fluidly communicate with at least one of the channels and/or cavities. In the completed device, the hole(s) optionally function as reservoirs for facilitating fluid or material introduction into the channels or chambers of the device, as well as providing ports at which, e.g., pressure elements (e.g., vacuum sources, etc.) are optionally placed into contact with fluids within the device, allowing application of pressure gradients along the channels of the device to control and direct fluid transport within the device. In optional embodiments, extensions are provided over these reservoirs to allow for increased fluid volumes, permitting longer running assays, and better controlling fluid flow parameters, e.g., hydrostatic pressures. Examples of methods and apparatuses for providing such extensions are described in, e.g., U.S. Pat. No. 6,251,343 "Microfluidic devices and systems incorporating cover layers," issued Jun. 26, 2001 to Dubrow et al., which is incorporated by reference in its entirety for all purposes. These devices are optionally coupled to a sample introduction port, e.g., a pipettor or capillary element, which serially introduces multiple samples, e.g., from the wells of a microtiter plate. Thus, in some embodiments, both reservoirs in the upper surface and external capillary elements are present in a single device.

The sources of reagents, enzymes, substrates, samples, eluents, separation buffers, and other materials are optionally fluidly coupled to the microchannels in any of a variety of ways. In particular, those systems comprising sources of materials set forth in Knapp et al. "Closed Loop Biochemical Analyzers" (WO 98/45481; PCT/US98/06723) and U.S. Pat. No. 5,942,443 issued Aug. 24, 1999, entitled "High Throughput Screening Assay Systems in Microscale Fluidic Devices" to J. Wallace Parce et al. and, e.g., in U.S. Application No. 60/128,643 filed Apr. 4, 1999, entitled "Manipulation of Microparticles In Microfluidic Systems," by Mehta et al. are applicable.

In these systems and as noted above, a capillary or pipettor element (i.e., an element in which components are optionally moved from a source to a microscale element such as a second channel or reservoir) is temporarily or permanently coupled to a source of material. The source is optionally internal or external to a microfluidic device that includes the pipettor or capillary element. Example sources include microwell plates, membranes or other solid substrates comprising lyophilized components, wells or reservoirs in the body of the microscale device itself and others.

V. Flow of Materials in Microfluidic Systems

The flowing of materials along the microchannels of the devices described herein is optionally carried out by a number of mechanisms, including pressure-based flow, electrokinetic flow, hydrodynamic flow, gravity-based flow, centripetal or centrifugal flow, or mechanisms that utilize hybrids of these techniques. In a preferred aspect, a pressure differential is used to flow the materials along, e.g., a capillary element or other channel.

The application of a pressure differential along the channel is carried out by any of a number of approaches. For example, it may be desirable to provide relatively precise control of the flow rate of samples and/or other reagents, e.g., to precisely control incubation or separation times, or the like depending on the particular assay being performed. As such, in many preferred aspects, flow systems that are more active than hydrostatic pressure driven systems are employed. In certain cases, materials may be flowed by applying a pressure differential across the length of the analysis channel. For example, a pressure source (positive or negative) is applied at the material reservoir at one end of the analysis channel, and the applied pressure forces the materials through the channel. The pressure source is optionally pneumatic, e.g., a pressurized gas, or a positive displacement mechanism, i.e., a plunger fitted into a material reservoir, for forcing the materials through the analysis channel. Alternatively, a vacuum source is applied to a reservoir at the opposite end of the channel to draw the materials through the channel. Pressure or vacuum sources may be supplied external to the device or system, e.g., external vacuum or pressure pumps sealably fitted to the inlet or outlet of the analysis channel, or they may be internal to the device, e.g., microfabricated pumps integrated into the device and operably linked to the analysis channel. Examples of microfabricated pumps have been widely described in the art. See, e.g., Published International Application No. WO 97/02357.

In an alternative simple passive aspect, the materials are deposited in a reservoir or well at one end of an analysis channel and at a sufficient volume or depth, that the material sample creates a hydrostatic pressure differential along the length of the analysis channel, e.g., by virtue of it having greater depth than a reservoir at an opposite terminus of the channel. The hydrostatic pressure then causes the materials to flow along the length of the channel. Typically, the reservoir volume is quite large in comparison to the volume or flow through rate of the channel, e.g., 10 µl reservoirs, vs. 1000 µm$^2$ channel cross-section. As such, over the time course of the assay, the flow rate of the materials will remain substantially constant, as the volume of the reservoir, and thus, the hydrostatic pressure changes very slowly. Applied pressure is then readily varied to yield different material flow rates through the channel. In screening applications, varying the flow rate of the materials is optionally used to vary the incubation time of the materials. In particular, by slowing the flow rate along the channel, one can effectively lengthen the amount of time between introduction of materials and detection of a particular effect. Alternatively, analysis channel lengths, detection points, or material introduction points are varied in fabrication of the devices, to vary incubation times. See also, "Multiport Pressure Control System," by Chien and Parce, U.S. Ser. No. 60/184,390, filed Feb. 23, 2000, which describes multiport pressure controllers that couple pumps to multiple device reservoirs.

In further alternate aspects, other flow systems are employed in transporting materials through the analysis channel. One example of such alternate methods employs electrokinetic forces to transport the materials. Electrokinetic transport systems typically utilize electric fields applied along the length of channels that have a surface potential or charge associated therewith. When fluid is introduced into the channel, the charged groups on the inner surface of the channel ionize, creating locally concentrated levels of ions near the fluid surface interface. Under an electric field, this charged sheath migrates toward the cathode or anode (depending upon whether the sheath comprises positive or negative ions) and pulls the encompassed fluid along with it, resulting in bulk fluid flow. This flow of fluid is generally termed electroosmotic flow. Where the fluid includes materials, the materials are also pulled along. A more detailed description of controlled electrokinetic material transport systems in microfluidic systems is described in Published International Patent Application No. WO 96/04547, which is incorporated herein by reference.

Hydrostatic, wicking and capillary forces are also optionally used to provide for fluid flow. See, e.g., "Method and Apparatus for Continuous Liquid Flow in Microscale Channels Using Pressure Injection, Wicking and Electrokinetic Injection," by Alajoki et al., U.S. Ser. No. 09/245,627, filed Feb. 5, 1999. In these methods, an adsorbent material or branched capillary structure is placed in fluidic contact with a region where pressure is applied, thereby causing fluid to move towards the adsorbent material or branched capillary structure.

In alternative aspects, flow of materials is driven by inertial forces. In particular, the analysis channel is optionally disposed in a substrate that has the conformation of a rotor, with the analysis channel extending radially outward from the center of the rotor. The materials are deposited in a reservoir that is located at the interior portion of the rotor and is fluidly connected to the channel. During rotation of the rotor, the centripetal force on the materials forces the reagents through the analysis channel, outward toward the edge of the rotor. Multiple analysis channels are optionally provided in the rotor to perform multiple different analyses. Detection of a detectable signal produced by the materials is then carried out by placing a detector under the spinning rotor and detecting the signal as the analysis channel passes over the detector. Examples of rotor systems have been previously described for performing a number of different assay types. See, e.g., Published International Application No. WO 95/02189. Test compound reservoirs are optionally provided in the rotor, in fluid communication with the analysis channel, such that the rotation of the rotor also forces the test compounds into the analysis channel.

For purposes of illustration the discussion has focused on a single channel and accessing capillary, however, it will be readily appreciated that these aspects may be provided as multiple parallel analysis channels and accessing capillaries, in order to substantially increase the throughput of the system. Specifically, single body structures may be provided with multiple parallel analysis channels coupled to multiple sample accessing capillaries that are positioned to sample multiple samples at a time from sample libraries, e.g., multiwell plates or other array formats. As such, these capillaries are generally spaced at regular distances that correspond with the spacing of wells in multiwell plates, e.g., 9 mm centers for 96 well plates, 4.5 mm for 384 well plates, and 2.25 mm for 1536 well plates.

VI. Computer Program Products

The present invention also provides a computer program product that includes a computer readable medium having a simple logic control program stored thereon for causing a computer to selectively contact capillary elements of a microfluidic device having n capillary elements extending therefrom and material at a selected material site of an array of materials having x material sites (e.g., a microwell plate, a substrate, a membrane, or the like) or fluid in a container. The computer readable medium optionally includes, e.g., a CD-ROM, a floppy disk, a tape, a flash memory device or component, a system memory device or component, a hard drive, a data signal embodied in a carrier wave, or the like.

The simple logic control program includes an instruction set for causing the computer to receive inputted initial parameters; an instruction set for causing the computer to effect movement of the microfluidic device to the selected material site or to the container according to inputted initial parameters or updated parameters, to effect movement of the array or the container relative to the microfluidic device according to inputted initial parameters or updated parameters, or both; an instruction set for causing the computer to effect contact of the capillary element and the material or the fluid according to inputted initial parameters or updated parameters; and an instruction set for causing the computer to effect deselection of the selected material site following contact between the capillary element and the material. The simple logic control program also typically includes an instruction set for causing the computer to vary or select a rate or a mode of moving or contacting the capillary element and the material or the fluid, to vary or select a rate or a mode of moving the array or the container, or both; an instruction set for causing the computer to effect drawing of selected quantities or volumes of the material from the selected material site into the microfluidic device through the capillary element according to inputted initial parameters or updated parameters while the capillary element and the material are in contact, to effect drawing of one or more selected quantities or volumes of the fluid from the container into the microfluidic device through the capillary element according to one or more inputted initial parameters or one or more updated parameters while the capillary element and the fluid are in contact, or both; or both additional instruction sets. In certain embodiments, the simple logic control program also optionally includes an instruction set for causing the computer to automatically update inputted initial parameters or other parameters.

VII. Kits

Generally, the microfluidic devices described herein are optionally packaged to include materials (e.g., samples, reagents, or the like) for performing the device's preferred function and/or a computer readable medium, such as a CD-ROM or a floppy disk having a simple logic control program of the invention. Optionally, computer readable media with the simple logic control program are packaged along with usage instructions and provided exclusive of other microfluidic components. The kits also optionally include any of the microfluidic devices described herein along with assay components, reagents, sample materials, particle sets, salts, separation matrices, control/calibrating materials, or the like. Component materials are optionally provided at predefined positions on arrays, such as on substrates or membranes included in the kits of the present invention. Such kits also typically include appropriate instructions for using the devices and reagents, and in cases where reagents are not predisposed in the devices themselves, with appropriate instructions for introducing the materials into the channels and/or chambers of the device. In this latter case, these kits optionally include special ancillary devices for introducing materials into the microfluidic systems, e.g., appropriately configured syringes/pumps, or the like (in one preferred embodiment, the device itself comprises a pipettor element, such as an electropipettor for introducing material into channels and chambers within the device). In the former case, such kits typically include a microfluidic device with necessary materials predisposed in the channels/chambers of the device. Generally, such reagents are provided in a stabilized form, so as to prevent degradation or other loss during prolonged storage, e.g., from leakage. A number of stabilizing processes are widely used for materials that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like. Kits also optionally include packaging materials or containers for holding a microfluidic device, system or reagent elements.

VIII. EXAMPLES

A. Example 1

Determining Contacting or Sampling Patterns

As described herein, the invention provides computer implemented methods for regulating patterns of contacting or sampling materials in or on arrays having essentially any number of material sites with microfluidic devices having essentially any number of capillary elements. The present non-limiting example illustrates certain embodiments of optional sampling patterns for 96-well and 384-well microwell plates with microfluidic devices having four capillary elements. As used herein, selected wells in a given microwell plate from which capillary elements sample materials during operation are also referred to as "dwell" patterns. Additionally, the illustrated patterns are designated for use with or without a recirculation/replenishing bath or trough. Eight dwell patterns are described below and depicted in accompanying figures for both the 96- and the 384-well microwell plates. These patterns are provided only for illustrative purposes. Many other patterns are also optionally designed and utilized according to the invention described herein. Furthermore, microfluidic devices having different numbers of capillary elements and/or capillary elements in different configuration are optionally utilized. For example, in certain embodiments, the software of the present invention provides the user with the option of selecting from preset dwell patterns and preset capillary element numbers and/or configurations, or designing customized sampling patterns with any capillary element format.

1. Illustrations of Optional 96-Well Dwell Patterns

Figure 11A:
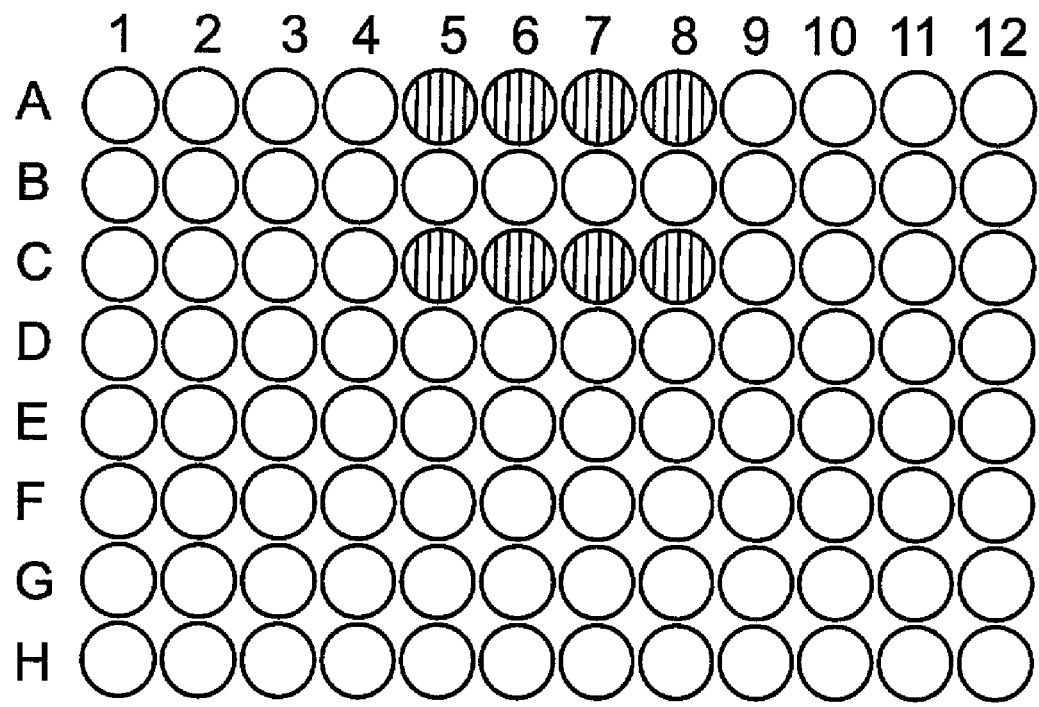
FIGS. 11A–P show display screens or portions thereof depicting various dwell patterns for a 96-well microwell plate and dialog boxes with files associated with the dwell patterns.
Figure 11C:
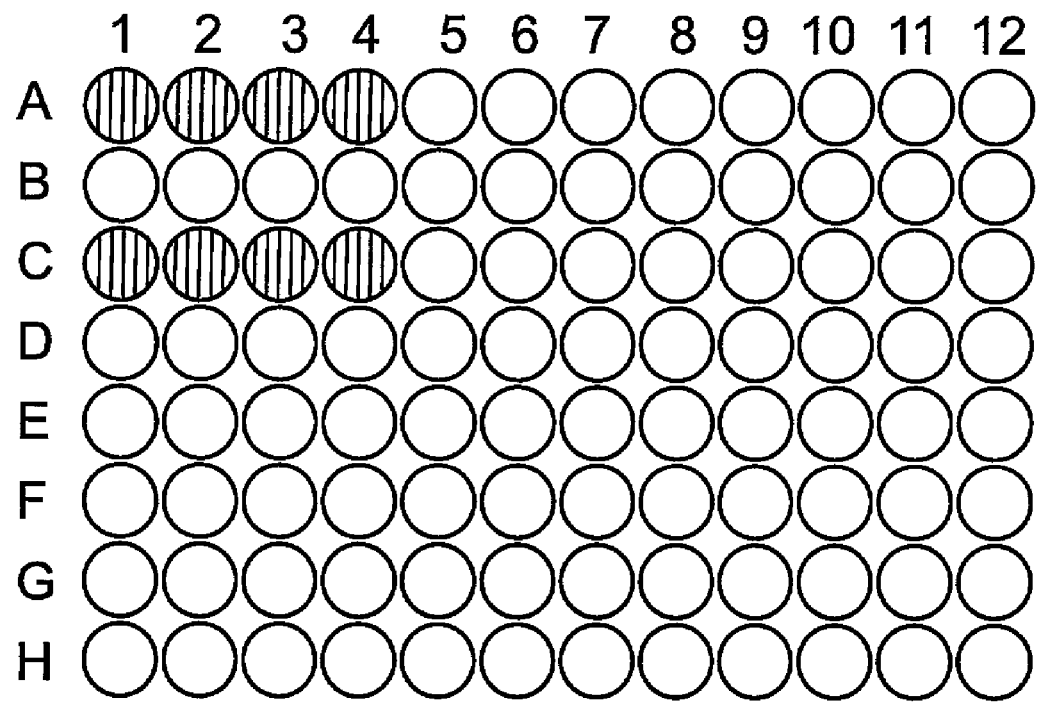
Figure 11E:
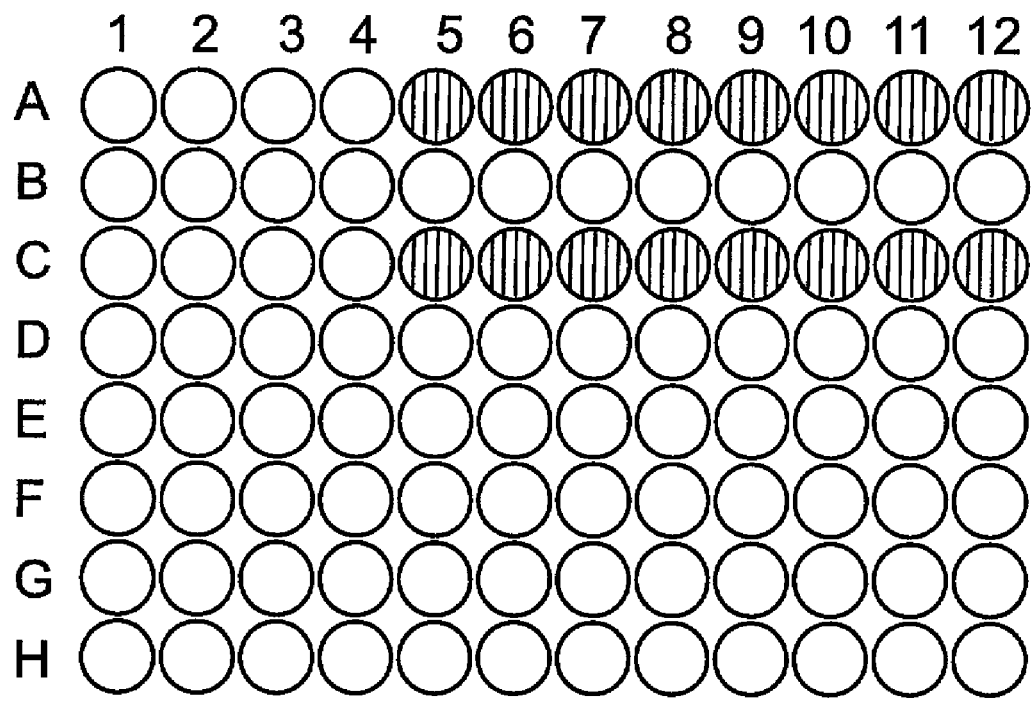
Figure 11G:
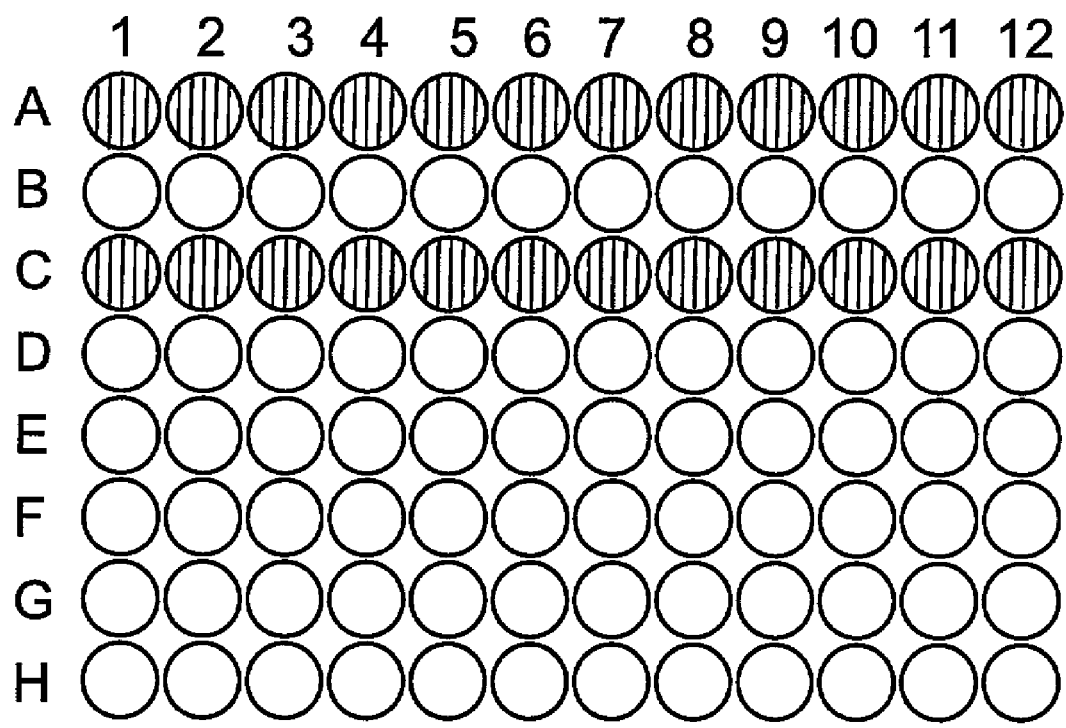

The capillary element configurations of the microfluidic devices intended for use with the dwell patterns in these illustrations have four capillary elements fixed such that for a 96-well microwell plate, the capillary elements sample every other well and row. Additionally, the wells sampled by the capillary elements for each dwell pattern are indicated as filled-in wells in the accompanying figures. FIGS. 11A–P illustrate display screens or portions thereof depicting various dwell patterns for a 96-well microwell plate and dialog boxes with files associated with the dwell patterns. In particular, FIGS. 11A and B show a dwell pattern and dialog box in which two capillary elements will sample materials in wells 5–8 in row A, and the other two capillary elements will sample materials in wells 5–8 in row C without intervening use of a recirculation/replenishing bath or trough. FIGS. 11C and D illustrate a dwell pattern and dialog box in which two capillary elements will sample materials in wells 1–4 in row A, and the other two capillary elements will sample materials in wells 1–4 in row C with intervening use of a recirculation/replenishing bath or trough. FIGS. 11E and F show a dwell pattern and dialog box in which two capillary elements will sample materials in wells 5–12 in row A, and the other two capillary elements will sample materials in wells 5–12 in row C without intervening use of a recirculation/replenishing bath or trough. FIGS. 11G and H illustrate a dwell pattern and dialog box in which two capillary elements will sample materials in wells 1–12 in row A, and the other two capillary elements will sample materials in wells 1–12 in row C with intervening use of a recirculation/ replenishing bath or trough.

Figure 11I:
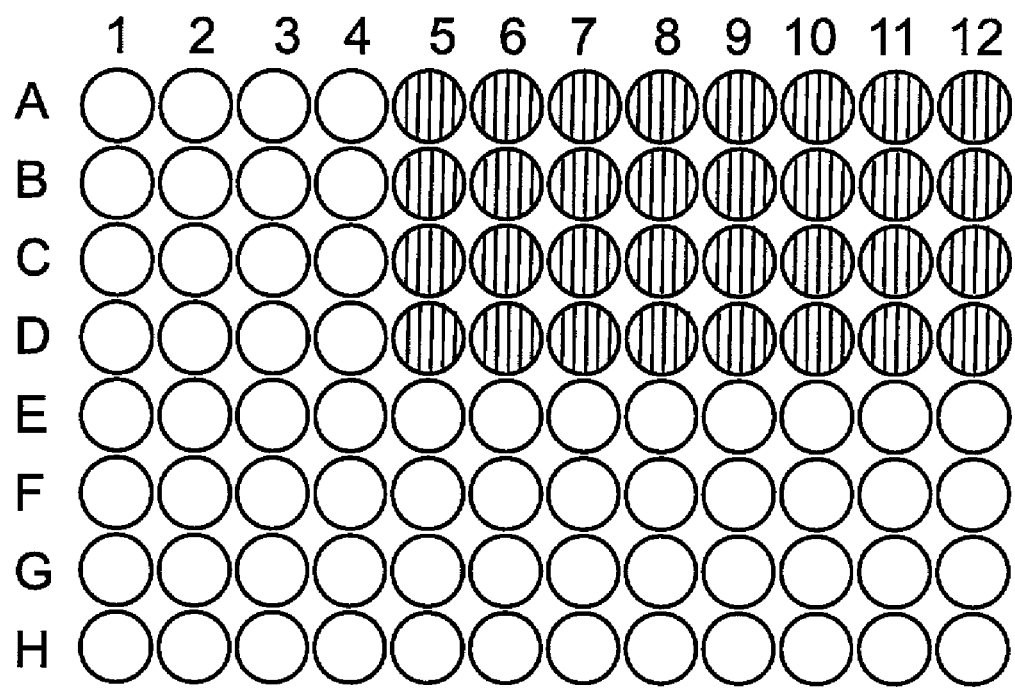
Figure 11K:
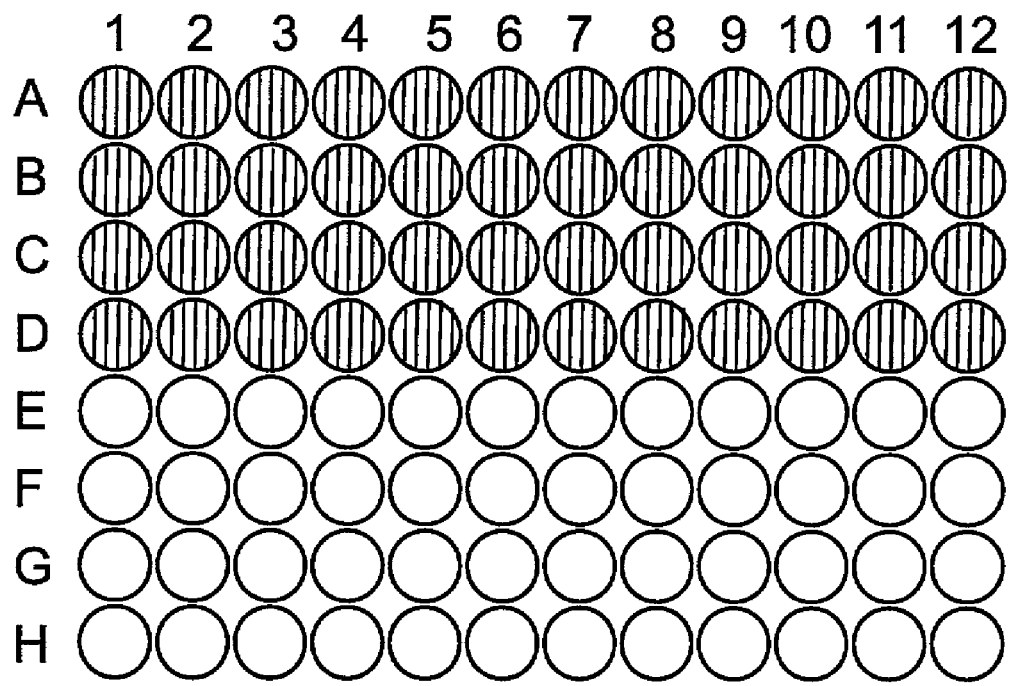
Figure 11M:
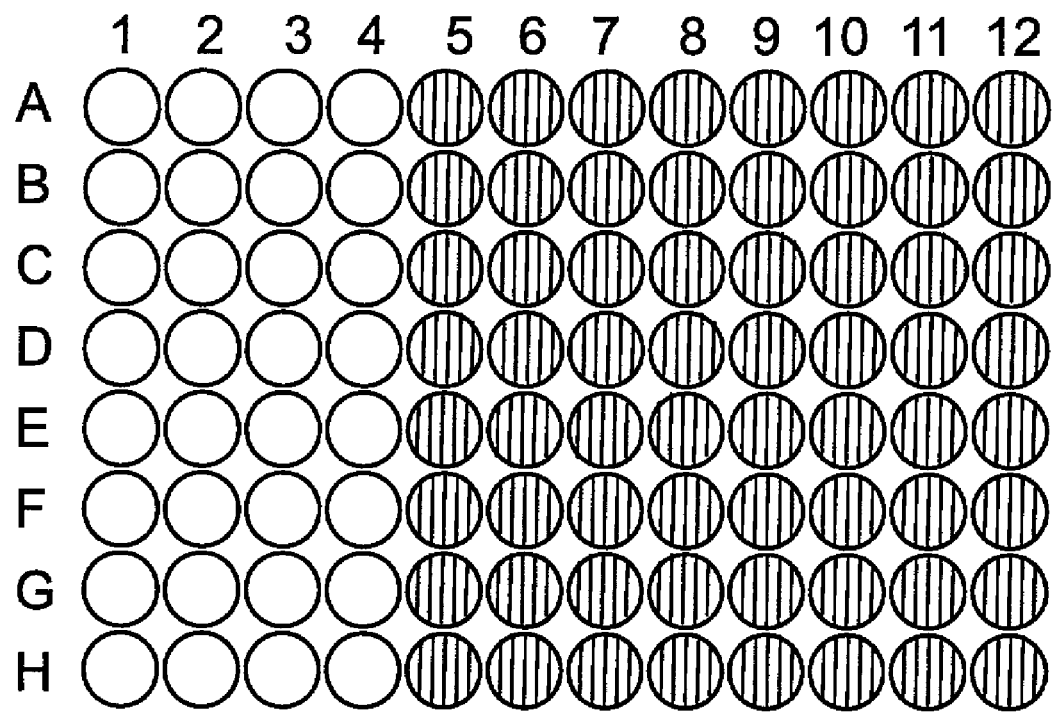
Figure 11O:
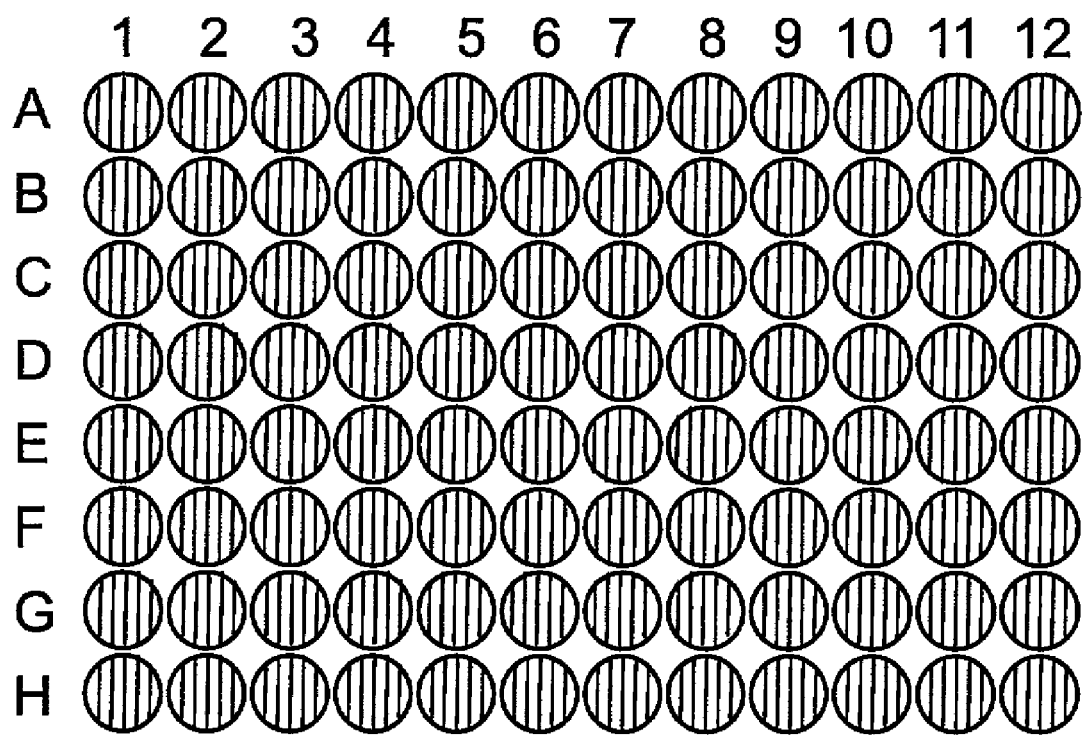

FIGS. 11I and J show a dwell pattern and dialog box in which two capillary elements will sample materials in wells 5–12 in rows A and B, and the other two capillary elements will sample materials in wells 5–12 in rows C and D without intervening use of a recirculation/replenishing bath or trough. FIGS. 11K and L illustrate a dwell pattern and dialog box in which two capillary elements will sample materials in wells 1–12 in rows A and B, and the other two capillary elements will sample materials in wells 1–12 in rows C and D with intervening use of a recirculation/replenishing bath or trough. FIGS. 11M and N show a dwell pattern and dialog box in which two capillary elements will sample materials in wells 5–12 in rows A, B, E, F, and the other two capillary elements will sample materials in wells 5–12 in rows C, D, G, H without intervening use of a recirculation/replenishing bath or trough. FIGS. 11O and P show a dwell pattern and dialog box in which two capillary elements will sample materials in wells 1–12 in rows A, B, E, F, and the other two capillary elements will sample materials in wells 1–12 in rows C, D, G, H with intervening use of a recirculation/ replenishing bath or trough.

2. Illustrations of Optional 384-Well Dwell Patterns

Figure 12A:
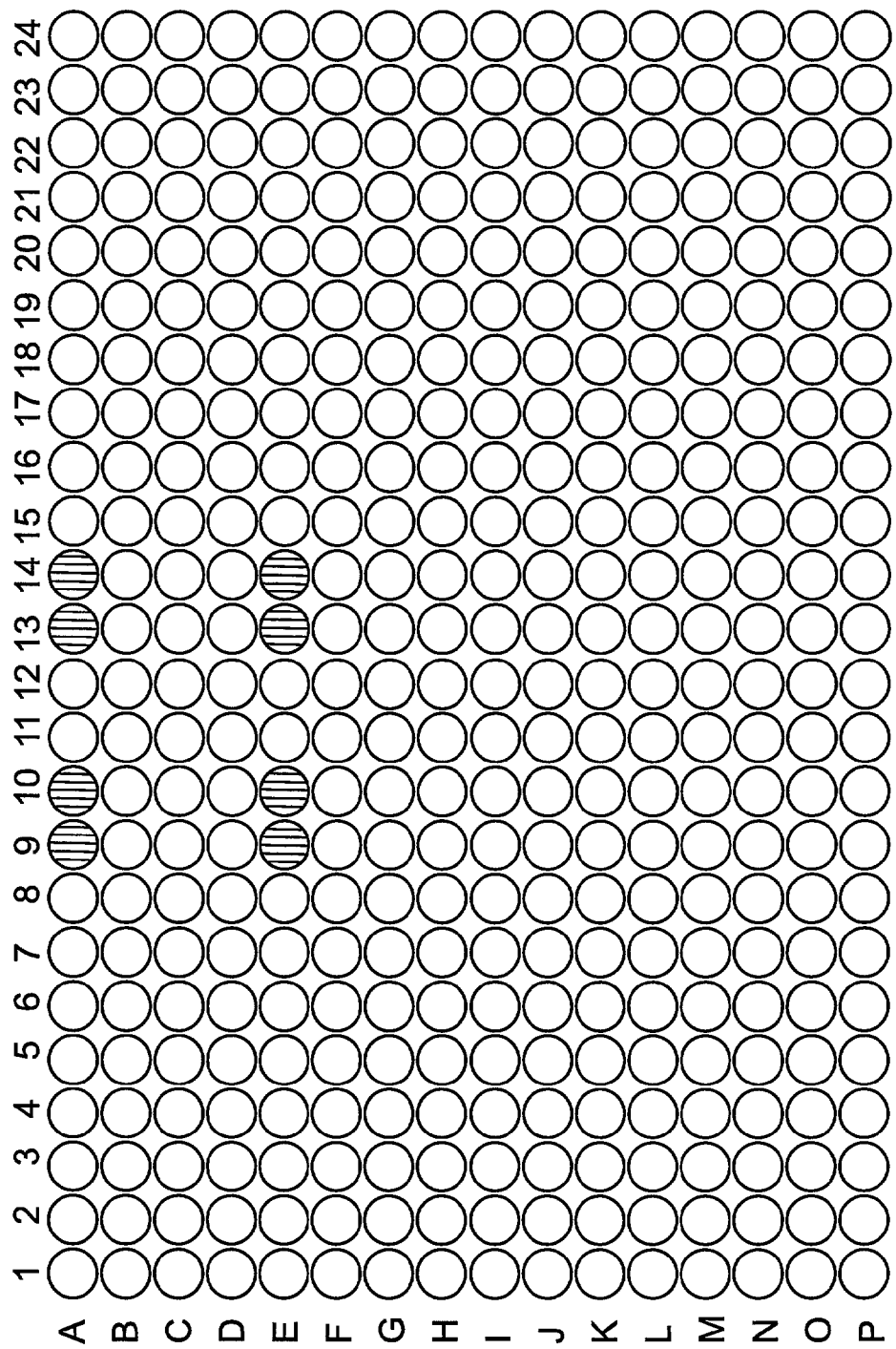
FIGS. 12A–P illustrate display screens or portions thereof depicting various dwell patterns for a 384-well microwell plate and dialog boxes with files associated with the dwell patterns.
Figure 12B:
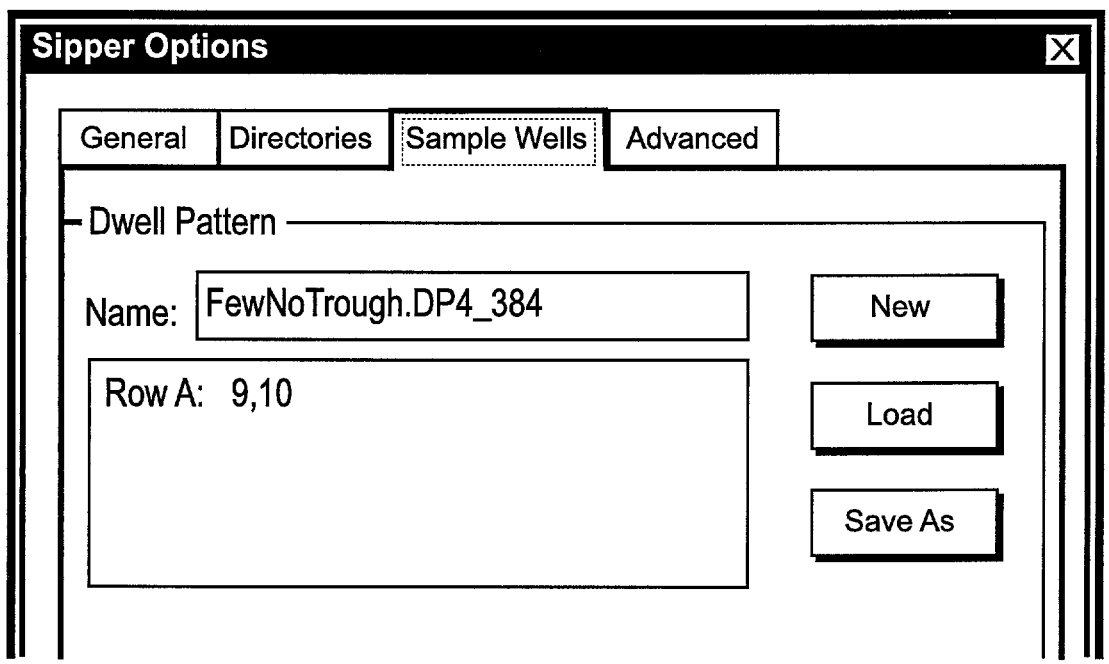
Figure 12C:
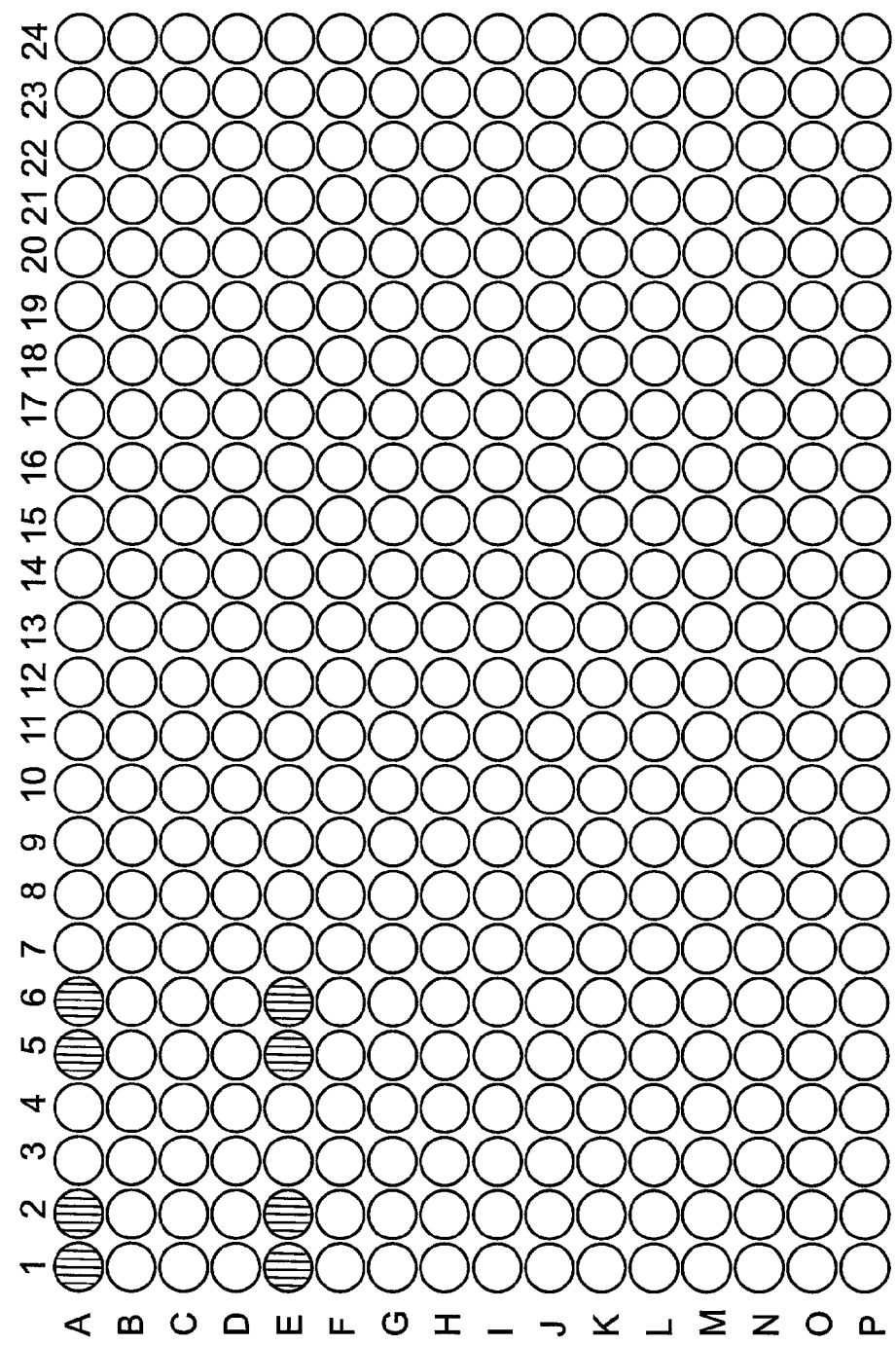
Figure 12D:
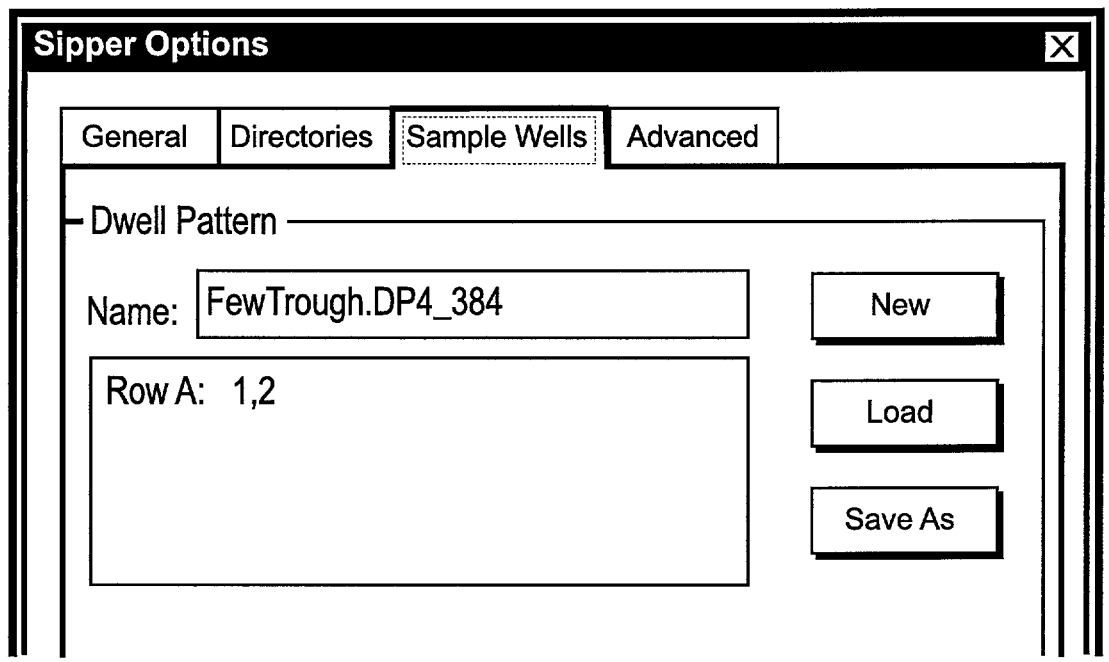
Figure 12E:
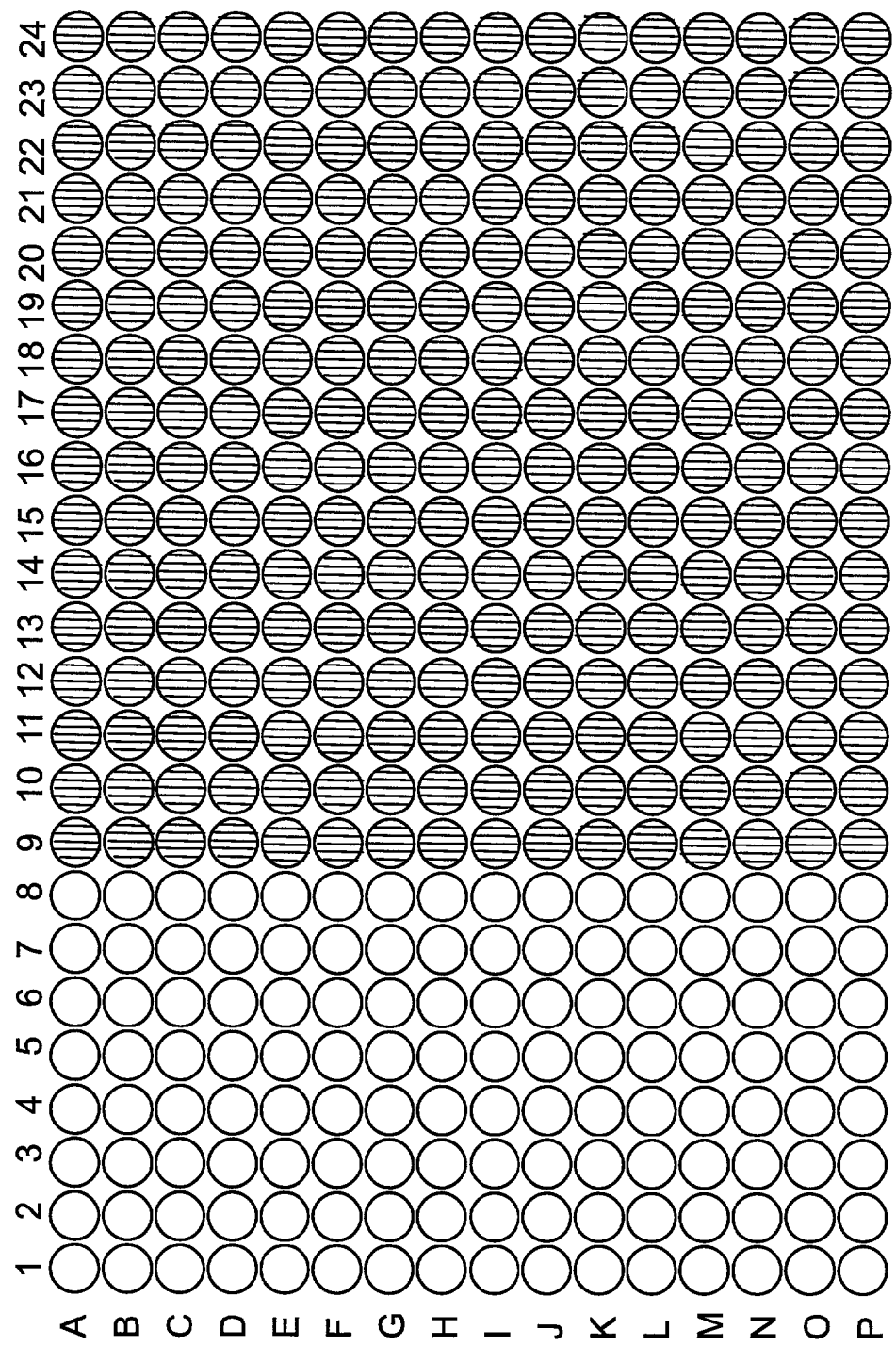
Figure 12F:
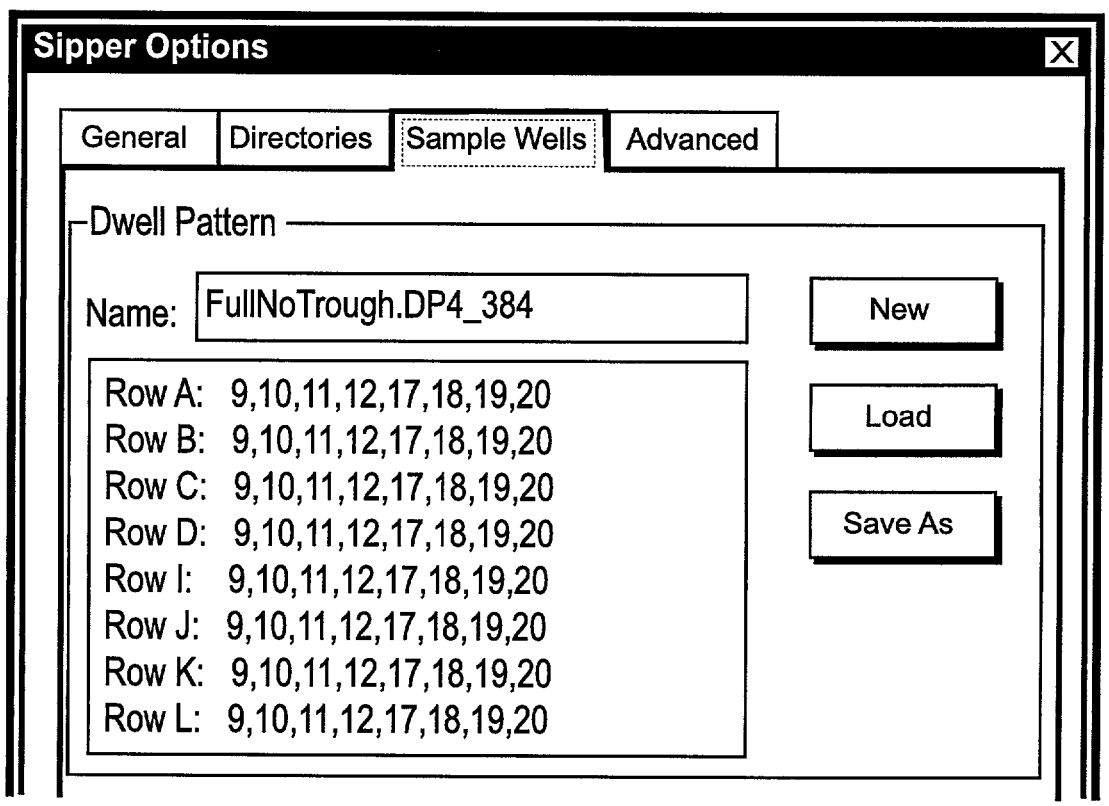
Figure 12G:
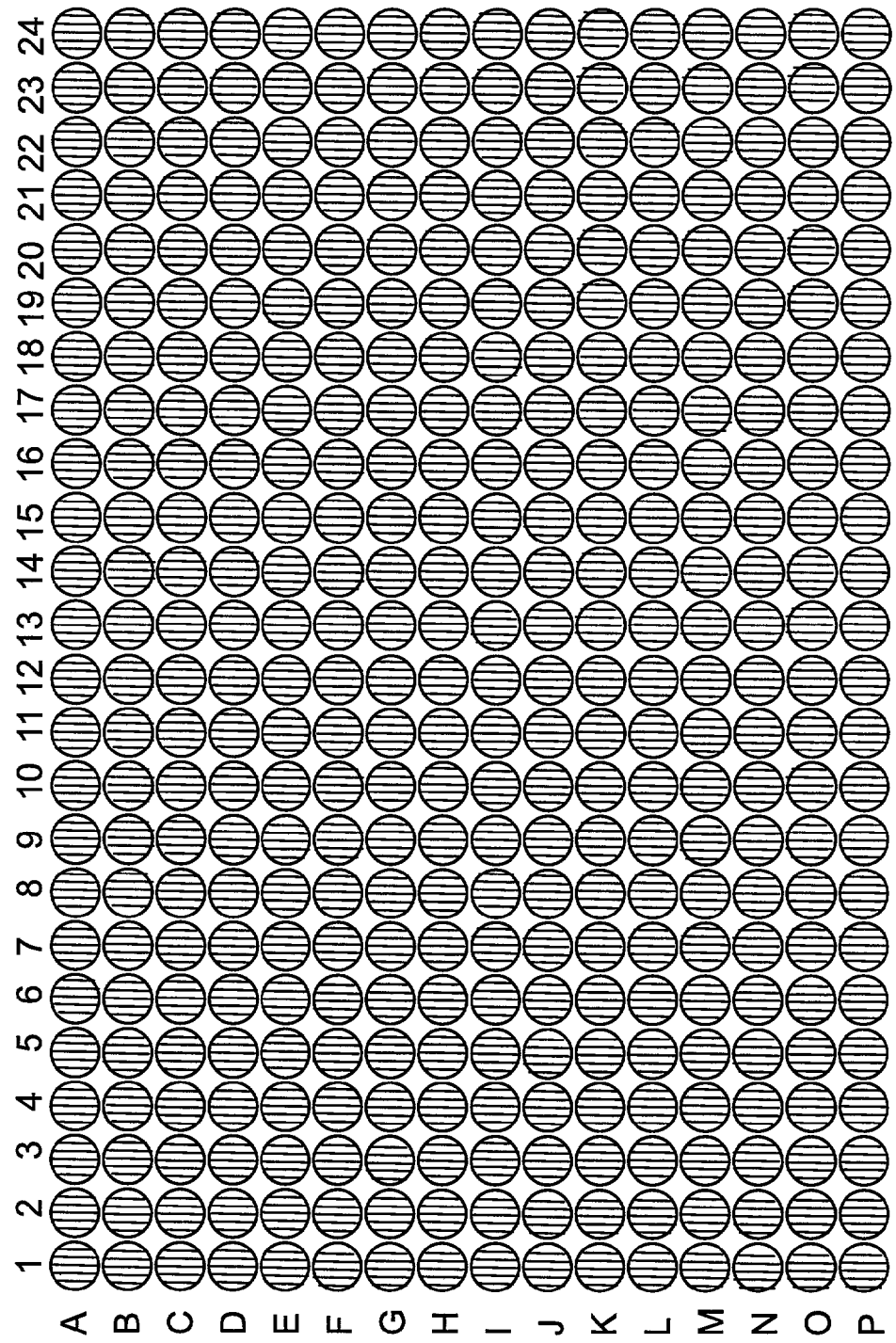
Figure 12H:
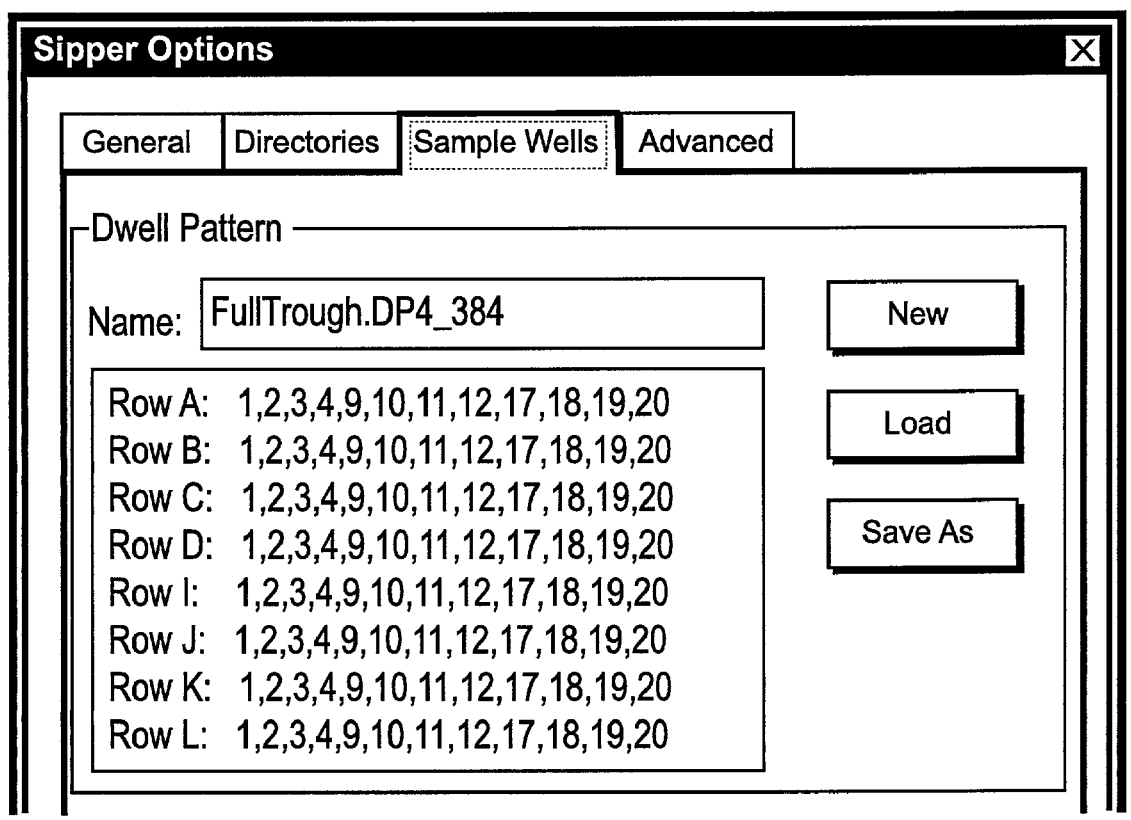

The capillary element configurations of microfluidic devices intended for use with the dwell patterns in these illustrations have four capillary elements fixed such that for a 384-well microwell plate, the capillary elements sample every fifth well and row. Additionally, the wells sampled by the capillary elements for each dwell pattern are indicated as filled-in wells in the accompanying figures. FIGS. 12A–P illustrate display screens or portions thereof depicting various dwell patterns for a 384-well microwell plate and dialog boxes with files associated with the dwell patterns. In particular, FIGS. 12A and B show a dwell pattern and dialog box in which two capillary elements will sample materials in wells 9, 10, 13, 14 in row A, and the other two capillary elements will sample materials in wells 9, 10, 13, 14 in row E without intervening use of a recirculation/replenishing bath or trough. FIGS. 12C and D illustrate a dwell pattern and dialog box in which two capillary elements will sample materials in wells 1, 2, 5, 6 in row A, and the other two capillary elements will sample materials in wells 1, 2, 5, 6 in row E with intervening use of a recirculation/replenishing bath or trough. FIGS. 12E and F show a dwell pattern and dialog box in which two capillary elements will sample materials in wells 9–24 in rows A–D and I–L, and the other two capillary elements will sample materials in wells 9–24 in rows E–H and M–P without intervening use of a recirculation/replenishing bath or trough. FIGS. 12G and H show a dwell pattern and dialog box in which two capillary elements will sample materials in wells 1–24 in rows A–D and I–L, and the other two capillary elements will sample materials in wells 1–24 in rows E–H and M–P with intervening use of a recirculation/replenishing bath or trough.

Figure 12I:
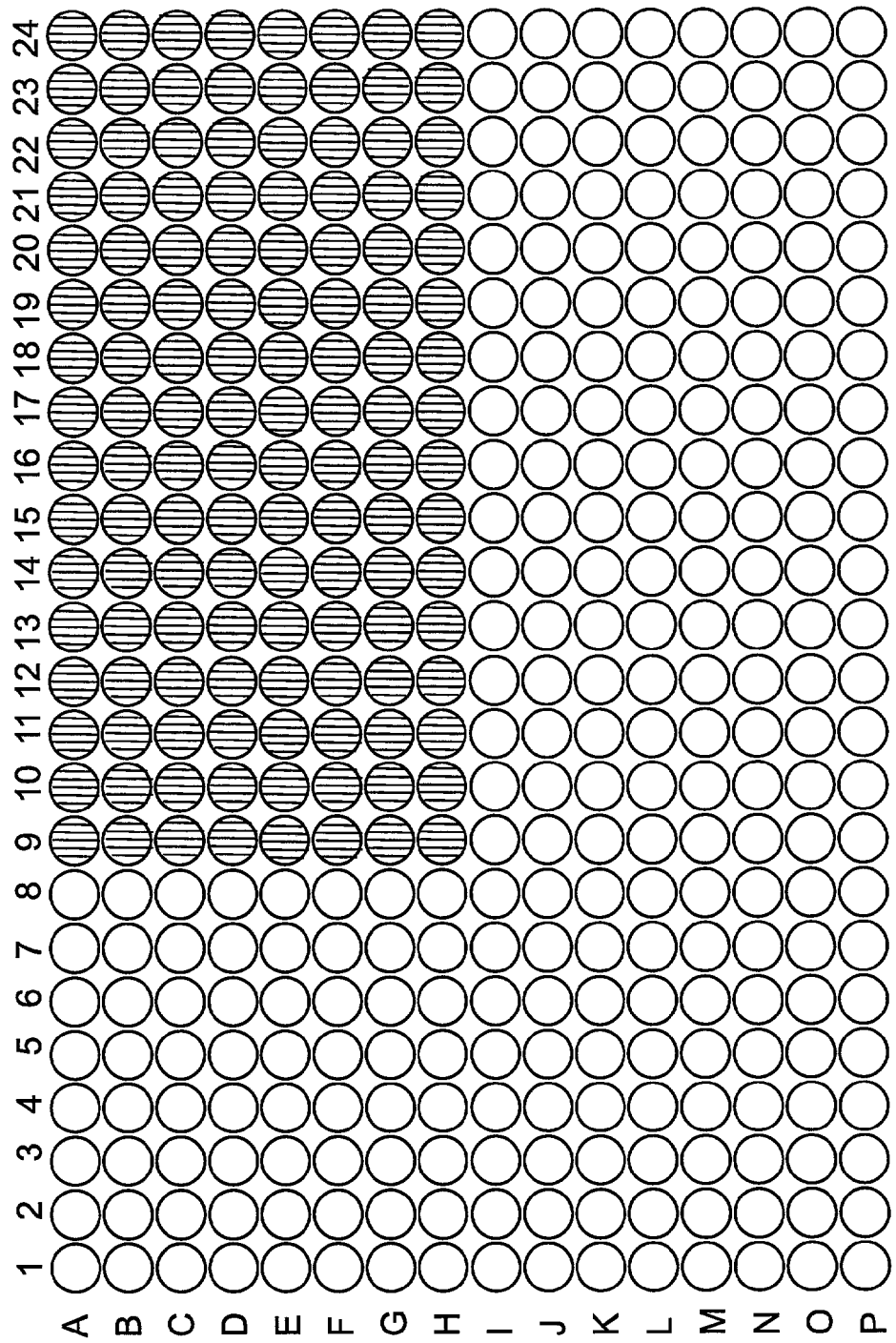
Figure 12J:
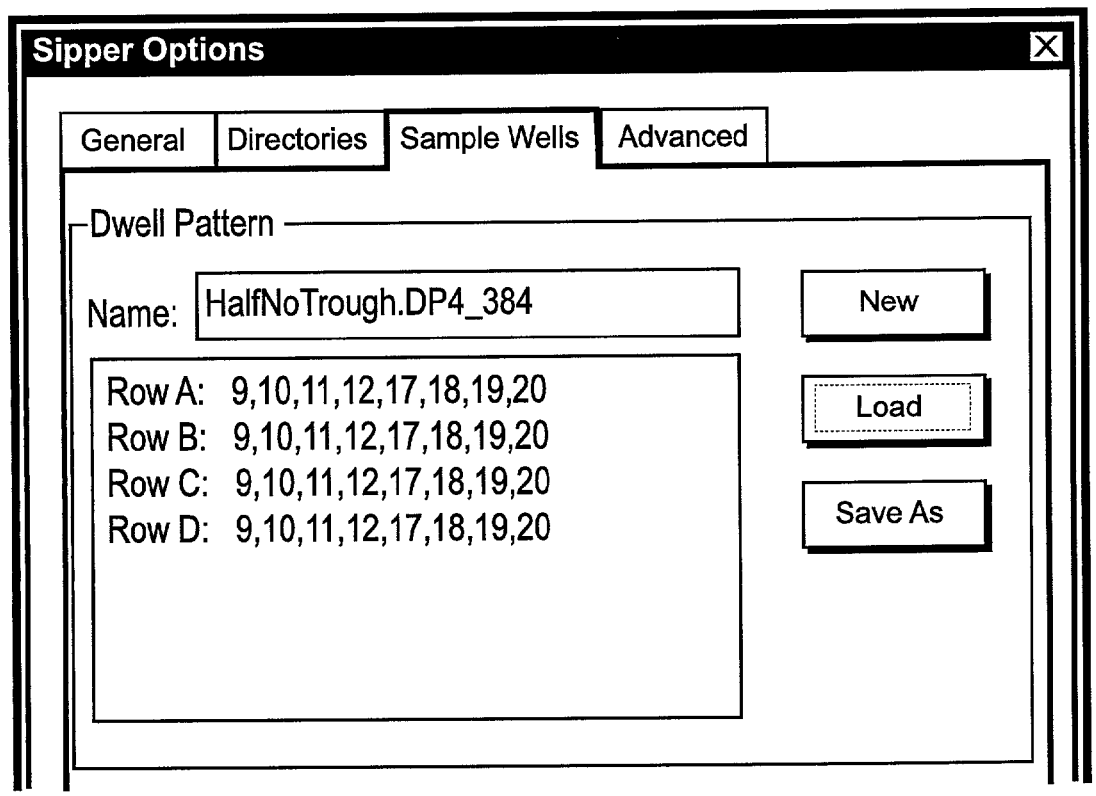
Figure 12K:
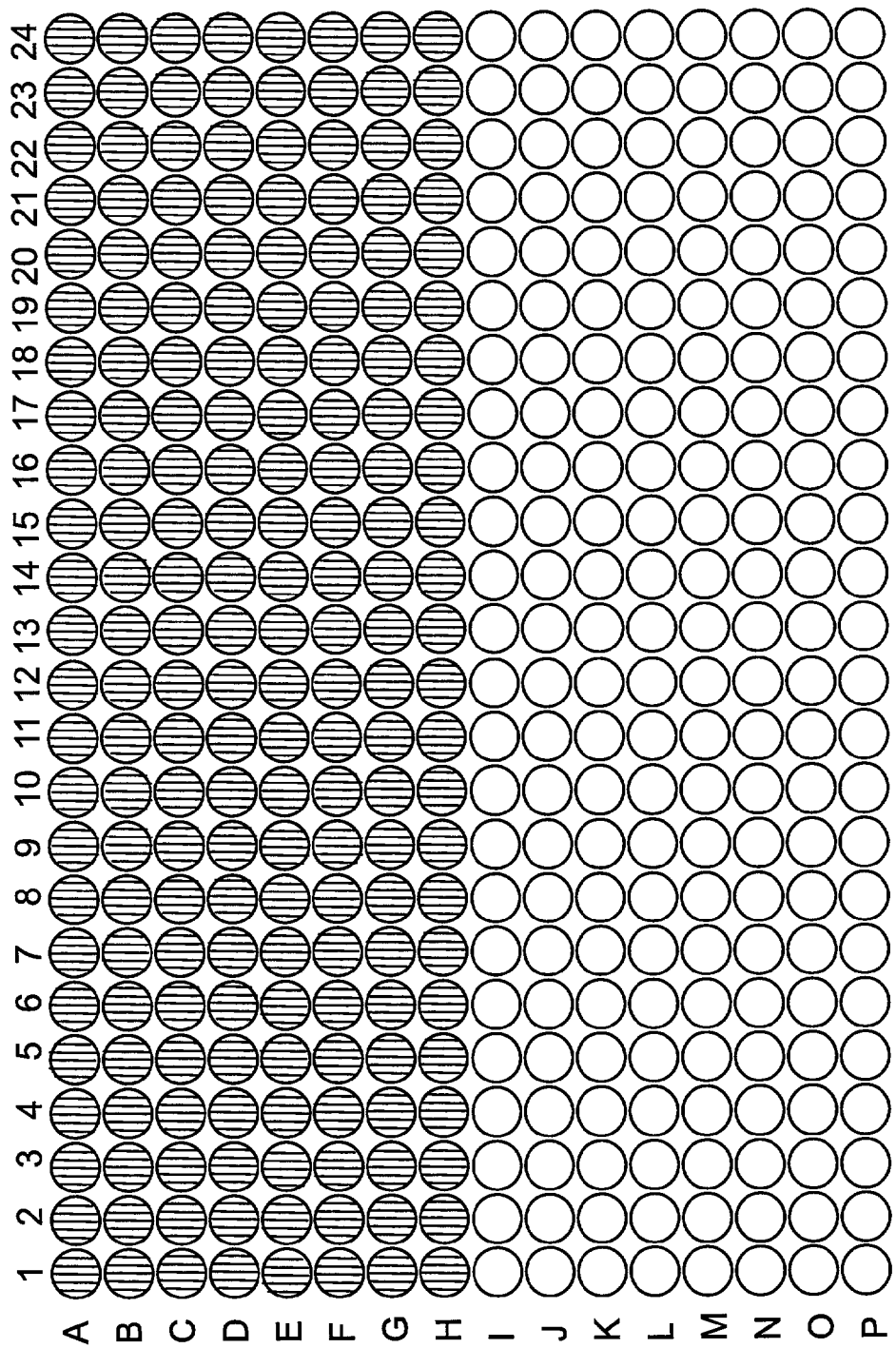
Figure 12L:
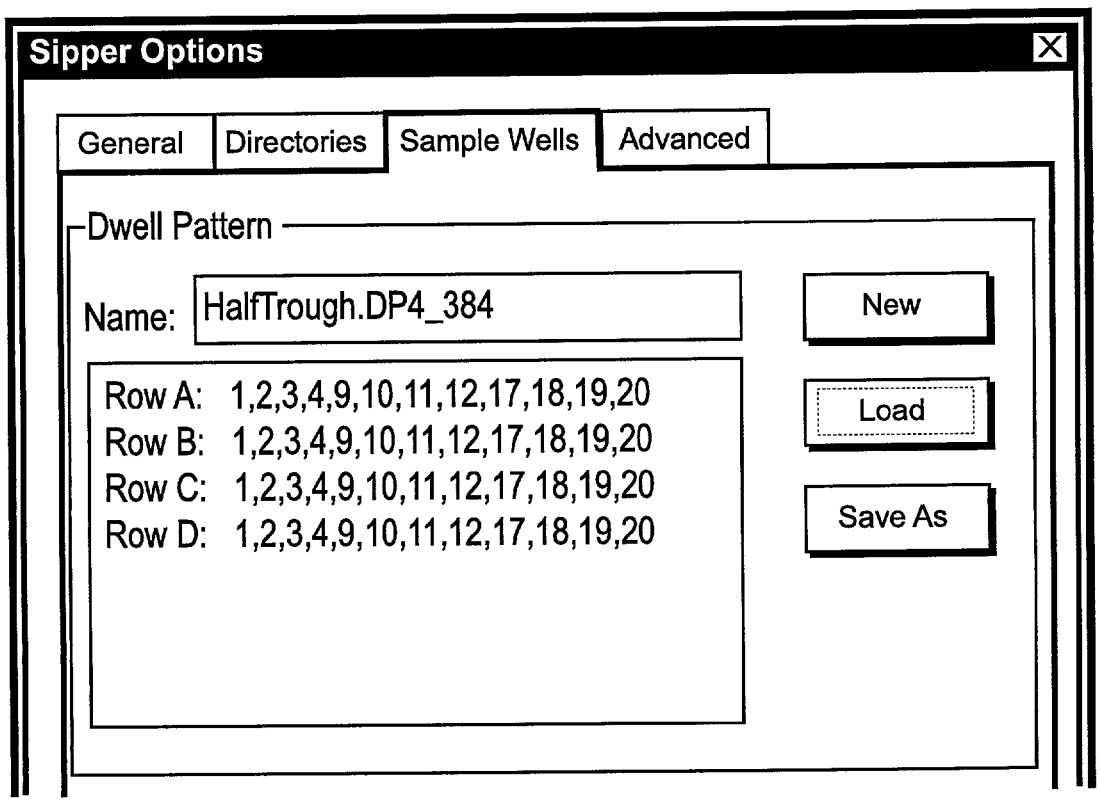
Figure 12M:
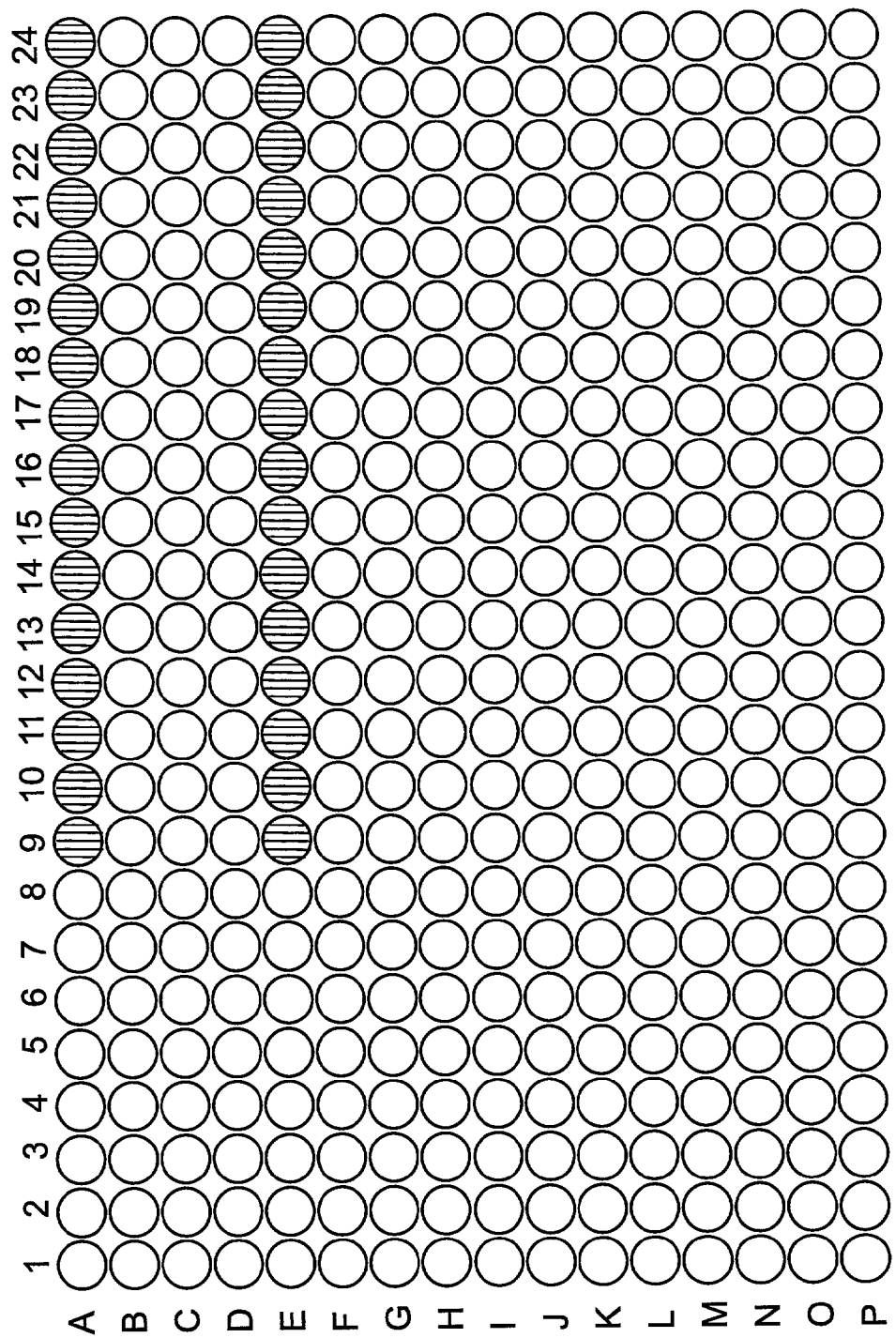
Figure 12N:
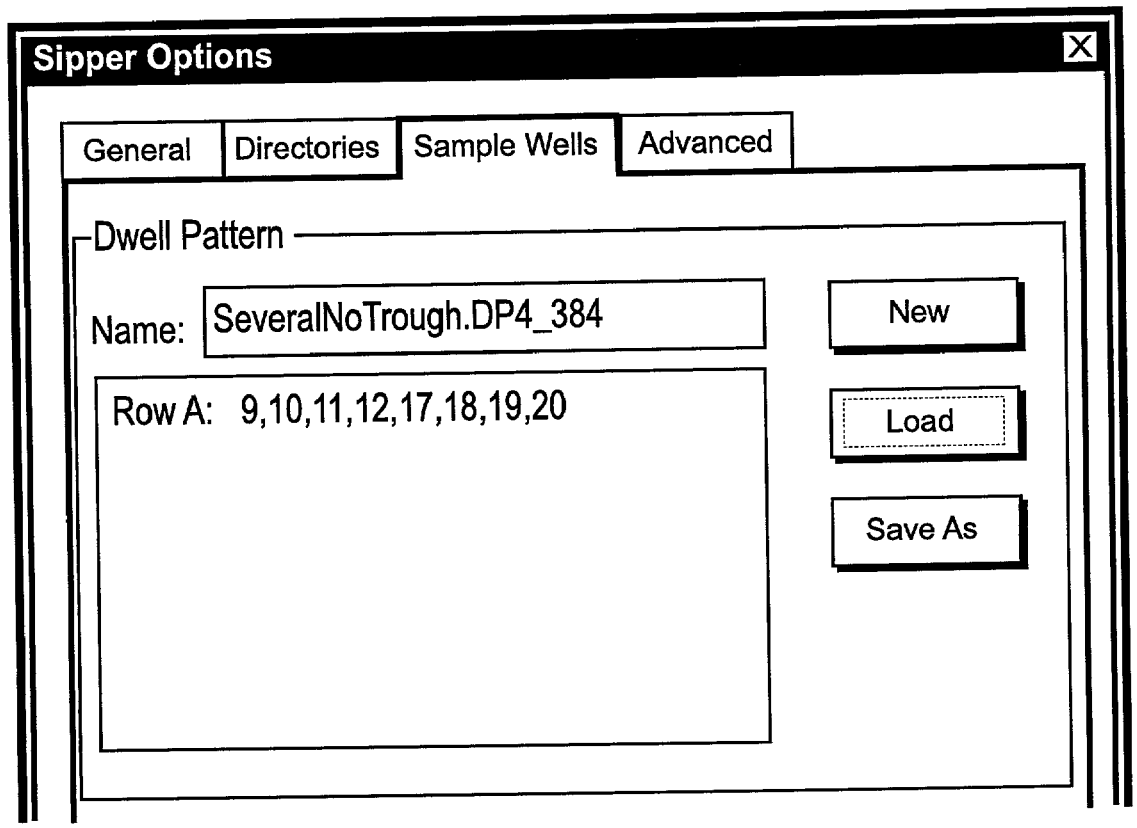
Figure 12O:
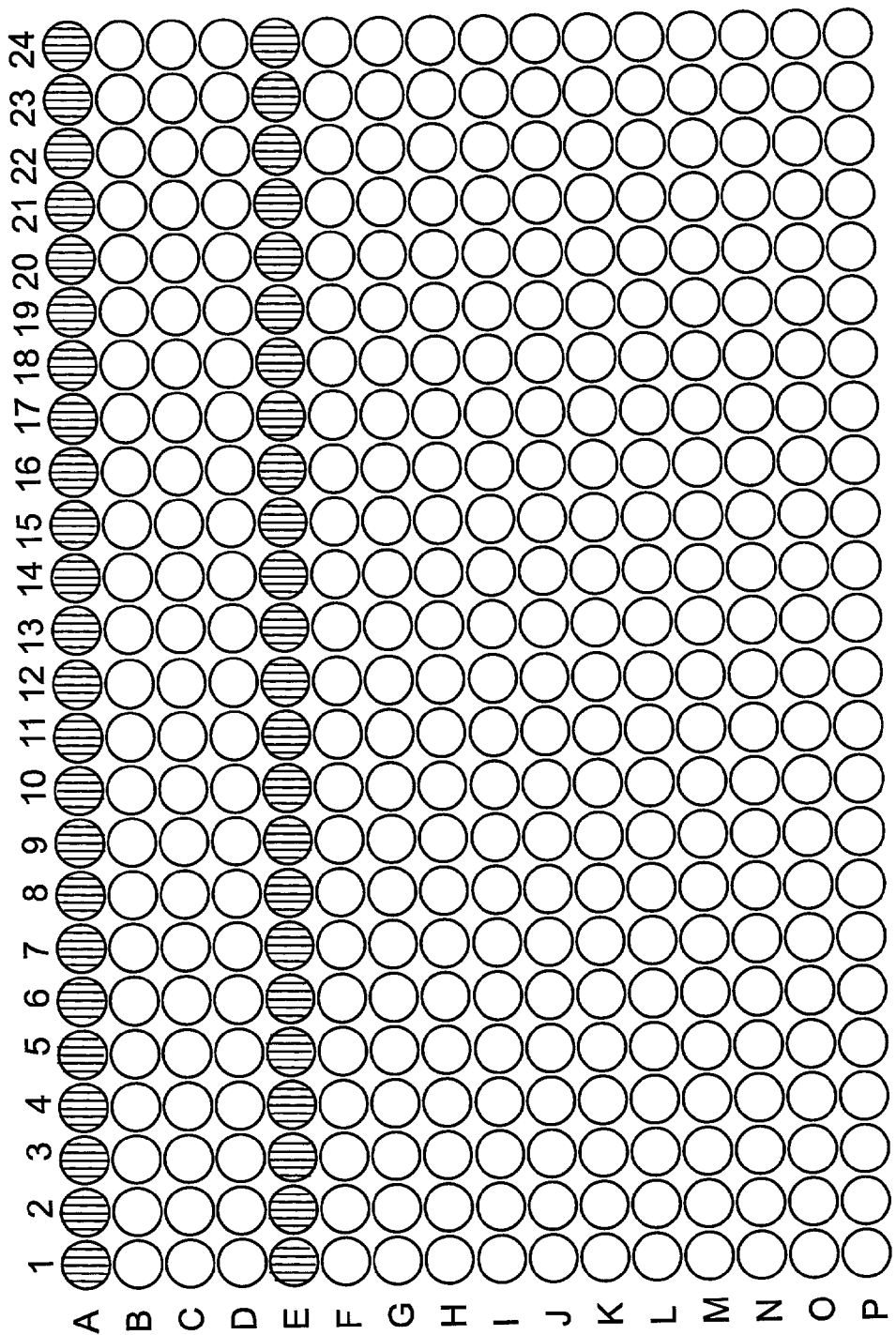
Figure 12P:
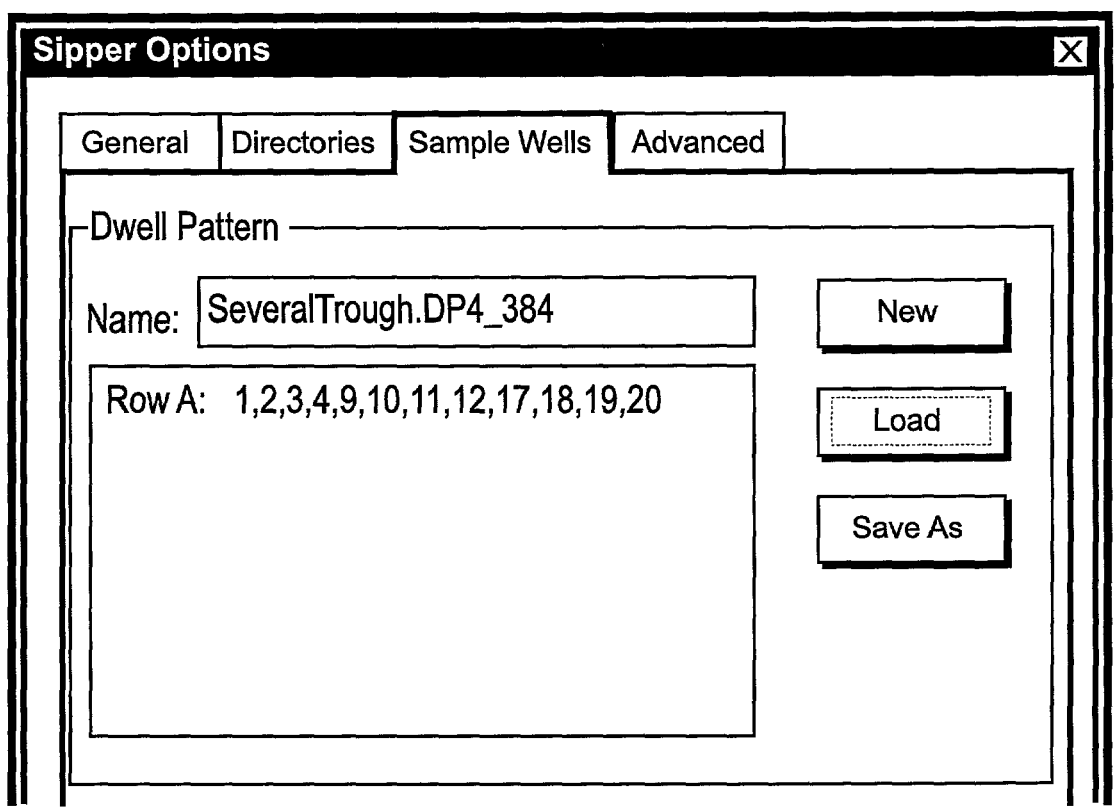

FIGS. 12I and J show a dwell pattern and dialog box in which two capillary elements will sample materials in wells 9–24 in rows A–D, and the other two capillary elements will sample materials in wells 9–24 in rows E–H without intervening use of a recirculation/replenishing bath or trough. FIGS. 12K and L illustrate a dwell pattern and dialog box in which two capillary elements will sample materials in wells 1–24 in rows A–D, and the other two capillary elements will sample materials in wells 1–24 in rows E–H with intervening use of a recirculation/replenishing bath or trough. FIGS. 12M and N show a dwell pattern and dialog box in which two capillary elements will sample materials in wells 9–24 in row A, and the other two capillary elements will sample materials in wells 9–24 in row E without intervening use of a recirculation/replenishing bath or trough. FIGS. 12O and P illustrate a dwell pattern and dialog box in which two capillary elements will sample materials in wells 1–24 in row A, and the other two capillary elements will sample materials in wells 1–24 in row E with intervening use of a recirculation/replenishing bath or trough.

B. Example 2

Selecting a Dwell Pattern in a Version of the Software

An example procedure for selecting a dwell pattern in one embodiment of the software is as follows:

1. Launch the system software application, if it is not open.

Figure 13A:
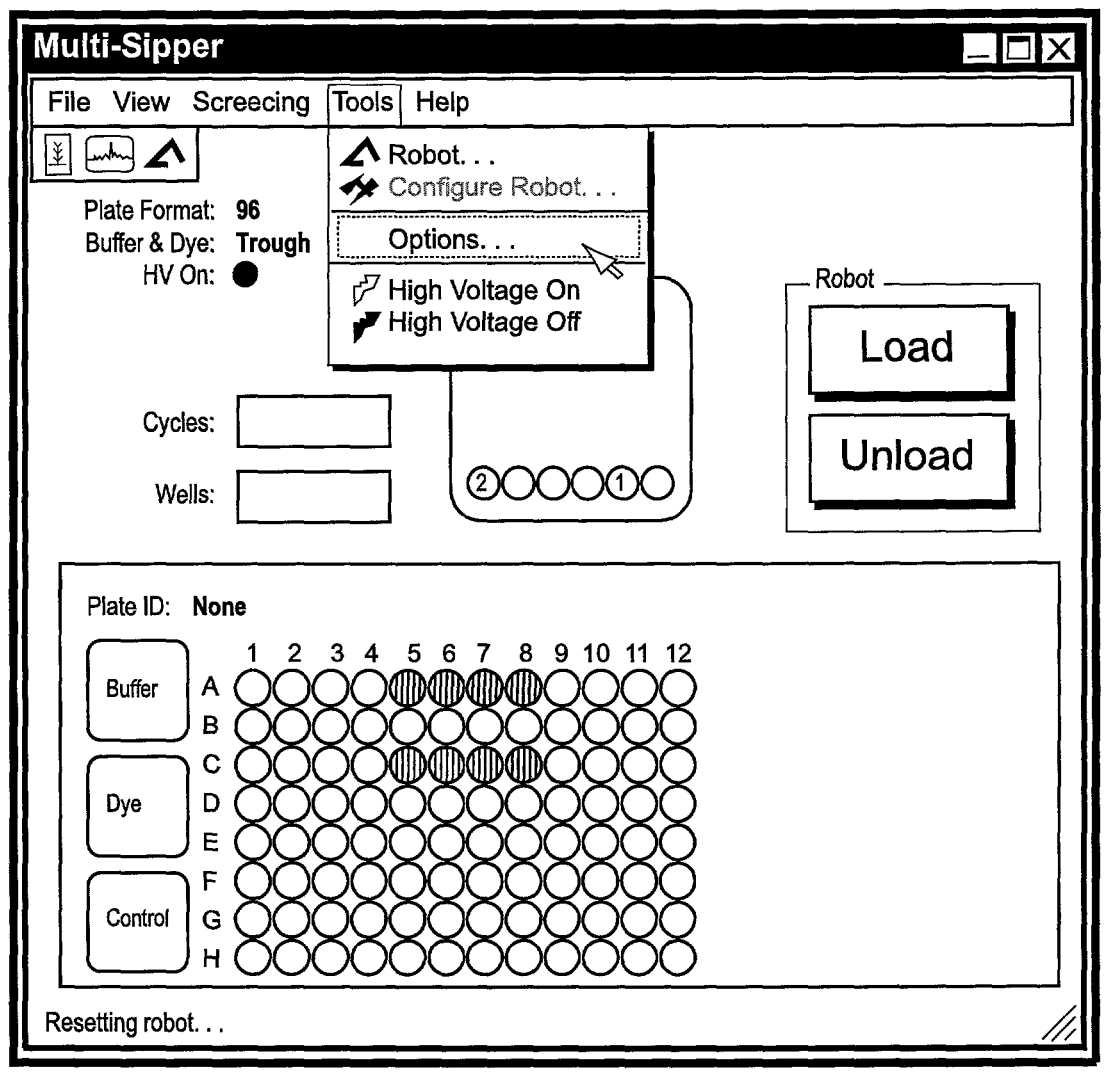
FIGS. 13A–F show display screens associated with a procedure for selecting a dwell pattern in one embodiment of the software.

2. In the Multi-Sipper dialog box, select Options under the Tools menu. As used herein, capillary elements are also referred to as sippers. FIG. 13A shows a display screen for performing this step.

Figure 13B:
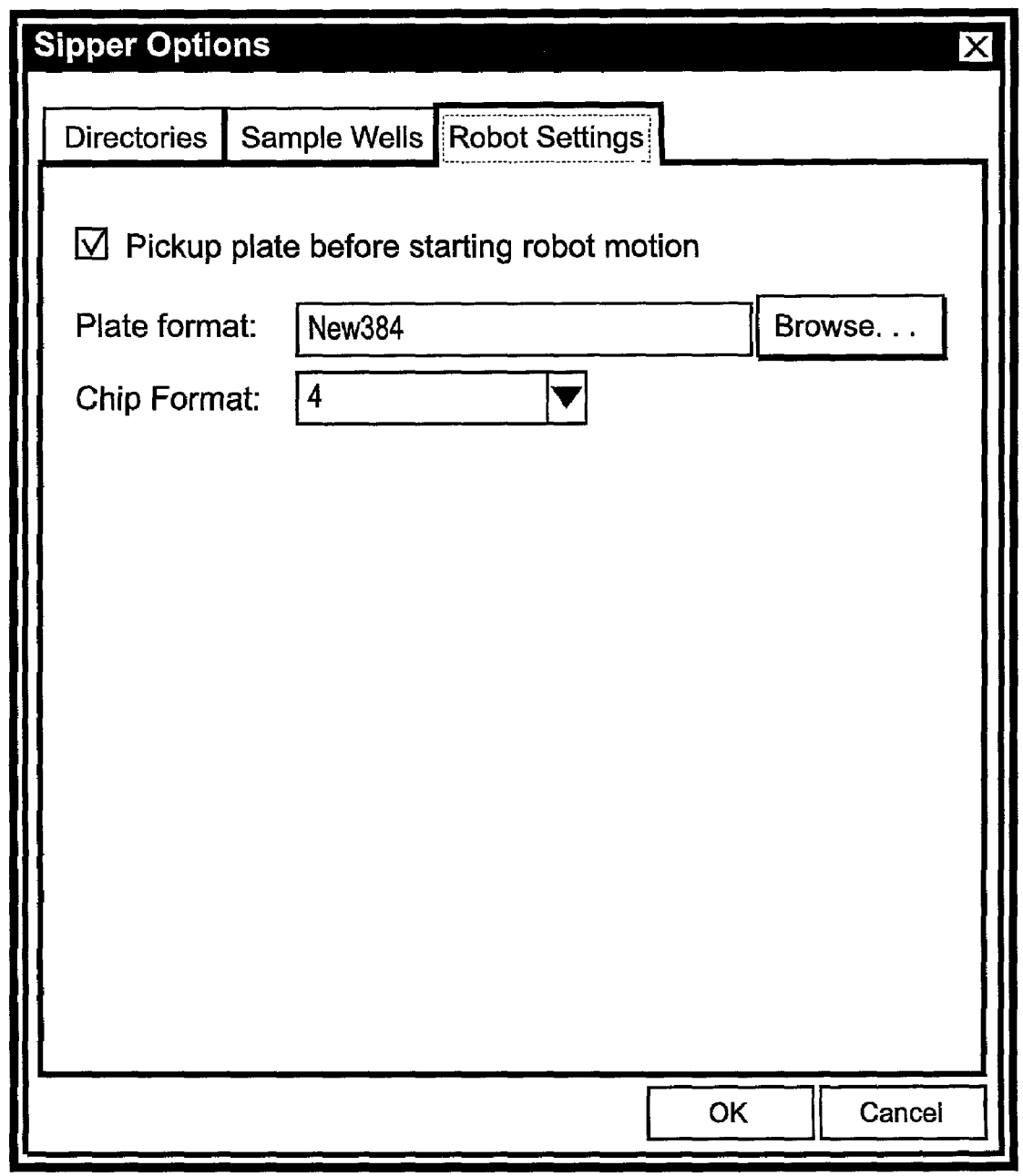

3. Click the Robot Settings tab to select the correct plate format. FIG. 13B shows a display screen for performing this step.

4. Click Browse next to Plate format and select from the available list.

Figure 13C:
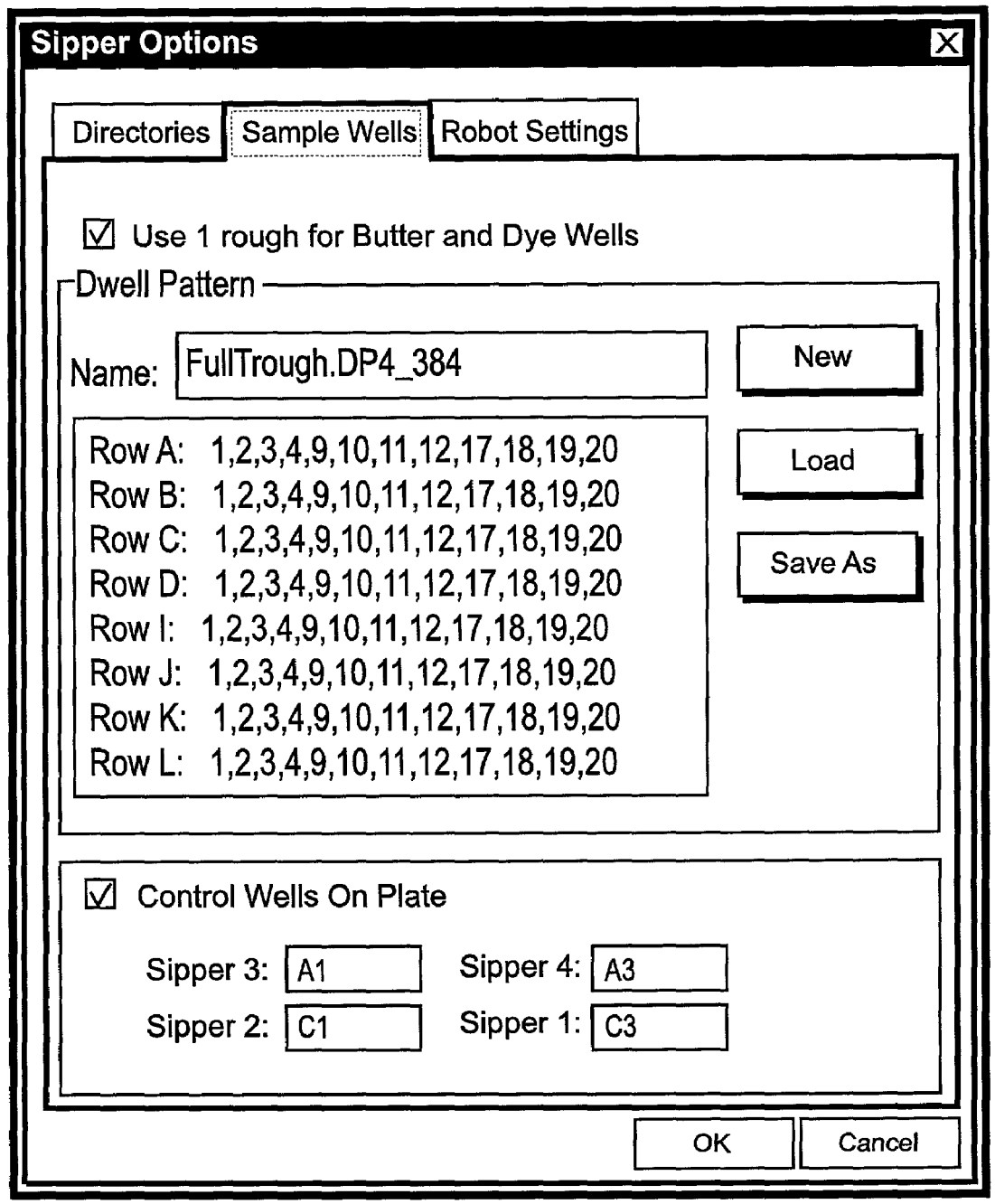

5. Click the Sample Wells tab to select the plate sampling pattern. FIG. 13C shows a display screen for performing this step.

Figure 13D:
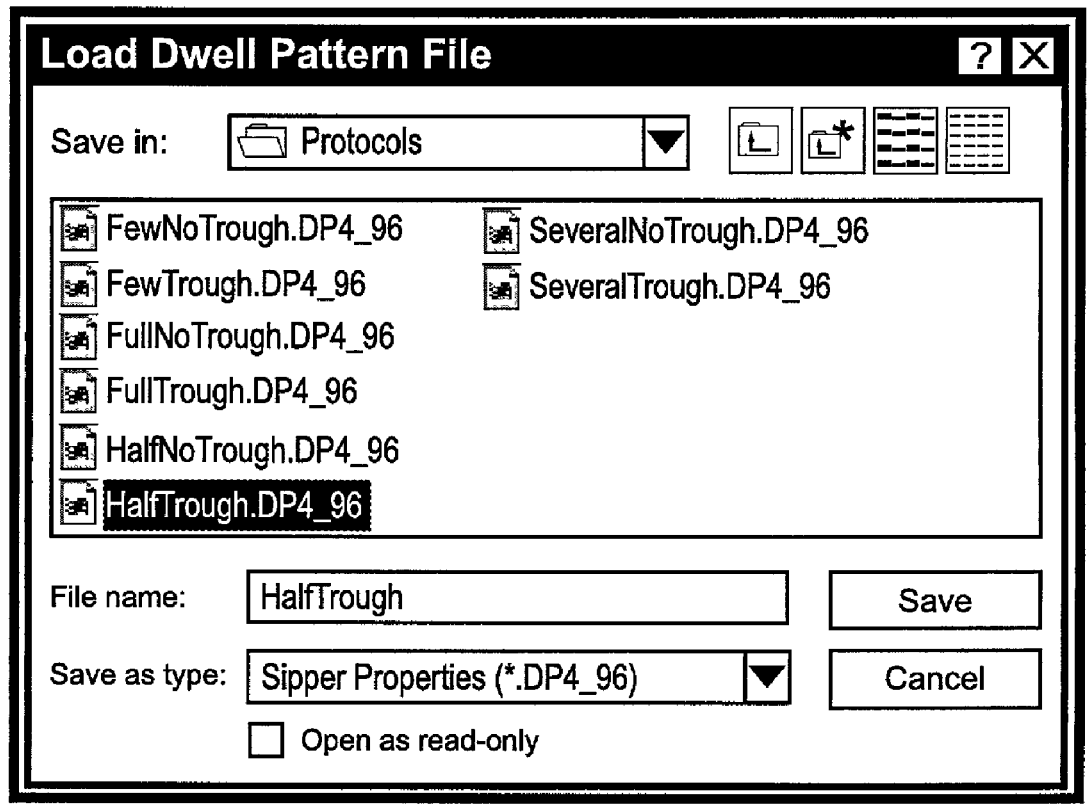

6. To change the current dwell pattern, click Load. The Load Dwell Pattern File dialog box opens. FIG. 13D shows a display screen for performing this step.

Figure 13E:
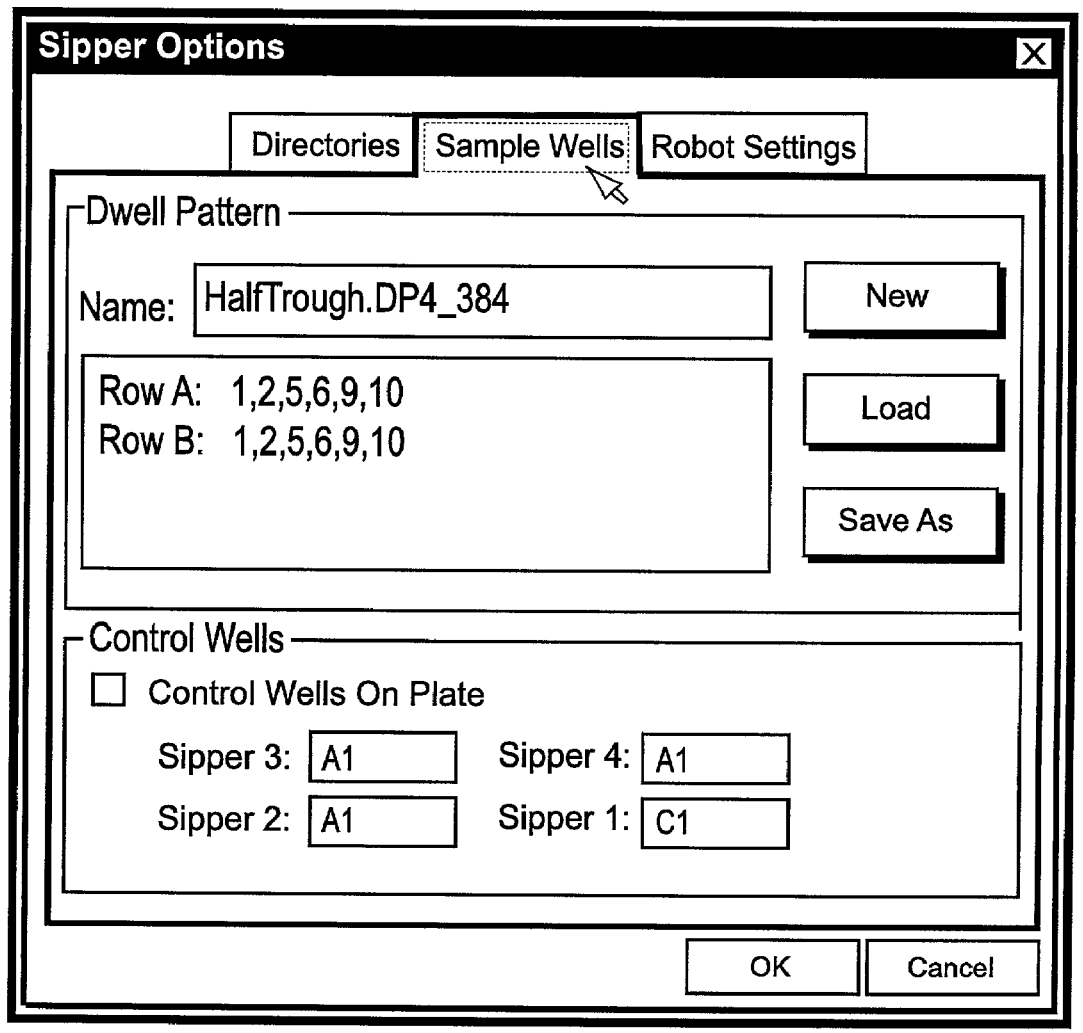

7. Select the desired dwell pattern file and click Open. The new dwell pattern now appears in the Sample Wells dialog box. FIG. 13E shows a display screen for performing this step.

Figure 13F:
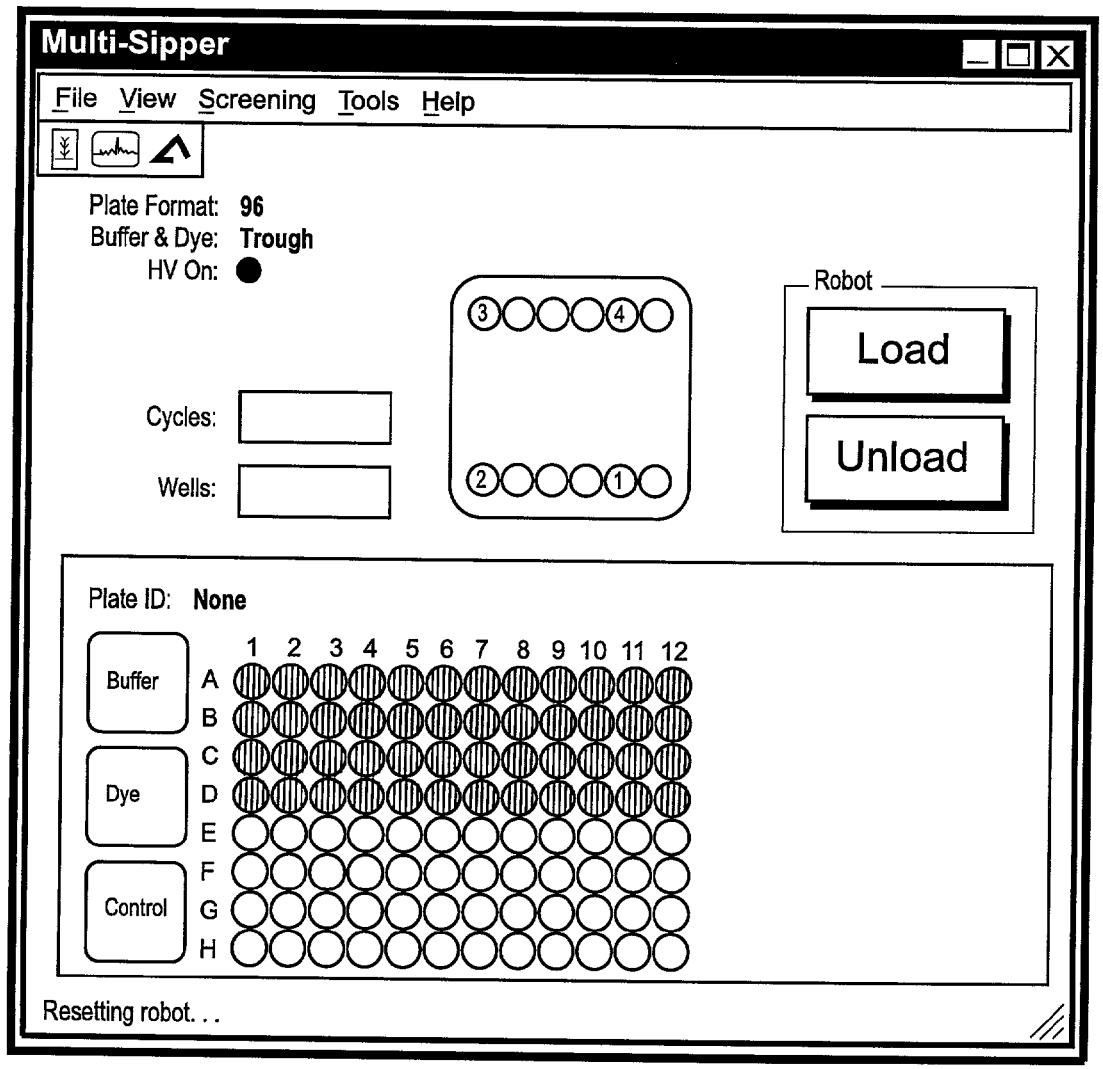

8. To select the dwell pattern of step 7, click OK. The selected dwell pattern will be indicated on the sample plate displayed in the Multi-Sipper dialog box. The appearance of wells that are to be sampled, which are depicted on the display screen, is distinguished from other wells (e.g., by use of different colors or the like). Similarly, once an experiment begins, the appearance of displayed wells is differentiated to represent wells to be sampled, wells that will not be sampled, wells that have been sampled, wells that are currently being sampled, or the like. The appearance of Buffer, Dye, and Control indicators will also be distinguished when capillary elements sample buffers, dyes, or controls, respectively. FIG. 13F shows a display screen for performing this step.

C. Example 3

Setting Multi-Capillary Element Properties

In certain embodiments, the software of the present invention includes a multi-sipper software component that is used to, e.g., home and move the robot into position, set the sipping or sampling properties, determine the file directory for data storage, or the like. The multi-sipper properties typically define the sipping parameters used for an assay and are accordingly typically set prior to the start of the particular assay. Optionally, multi-capillary element properties are set at the same time dwell patterns are set. The multi-capillary element properties are also optionally saved as a unique file and loaded subsequently for use in another assay.

The homing of the robot arm typically occurs automatically when the application is initiated. Optionally, the robot is homed manually by selecting Reset located under the Screening menu. To home the robot, whether upon start up or manually, generally includes a microfluidic device cartridge installed on the system. Manual movement of the robot arm is typically utilized to verify alignment of capillary elements and wells on microwell plates.

Figure 14A:
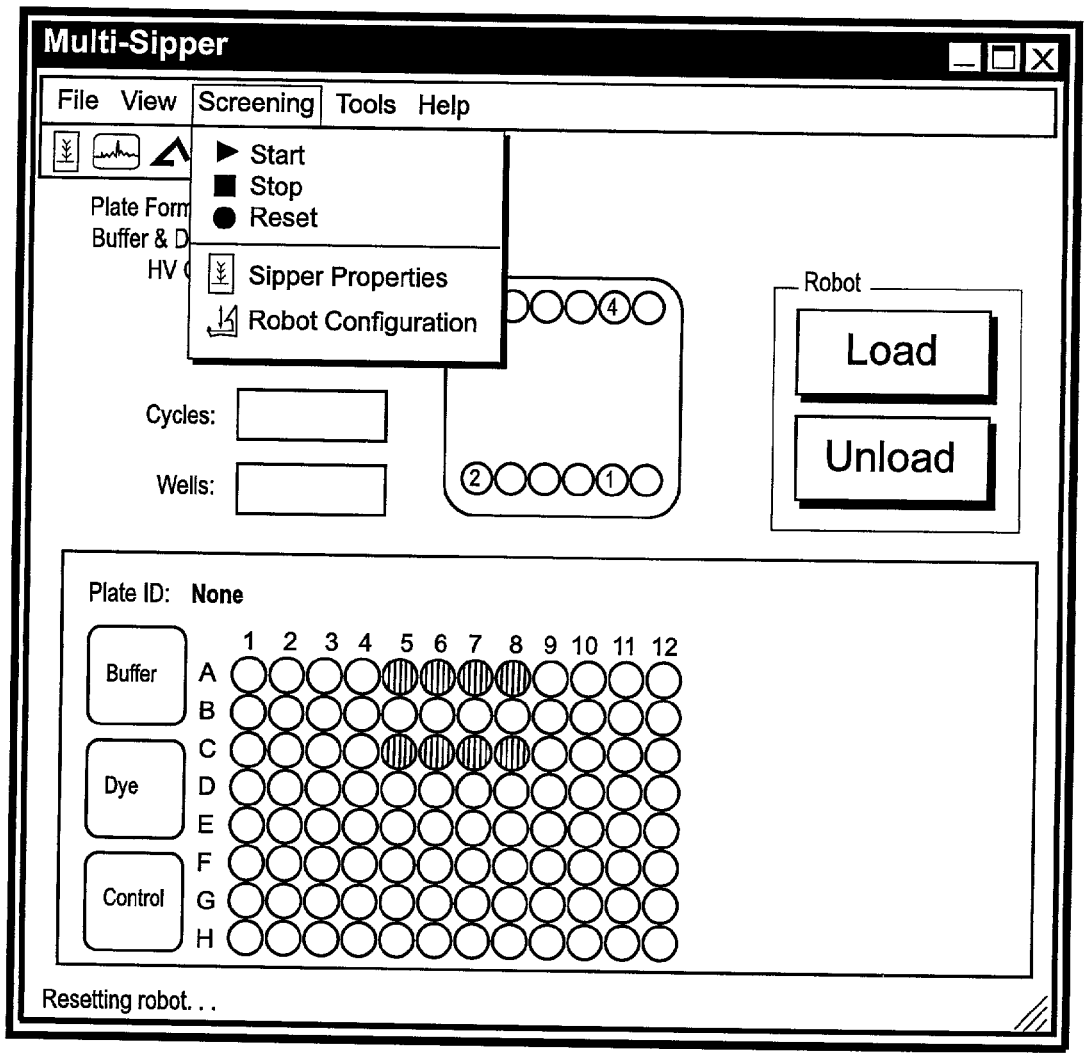
FIGS. 14A–C illustrate display screens associated with a procedure for selecting multi-capillary element properties in one embodiment of the software.

An example procedure for setting multi-sipper properties in one embodiment of the software is as follows:

1. Click on the Multi-Sipper dialog box to activate it and select Sipper Properties under the Screening menu. FIG. 14A shows a display screen for performing this step.

Figure 14B:
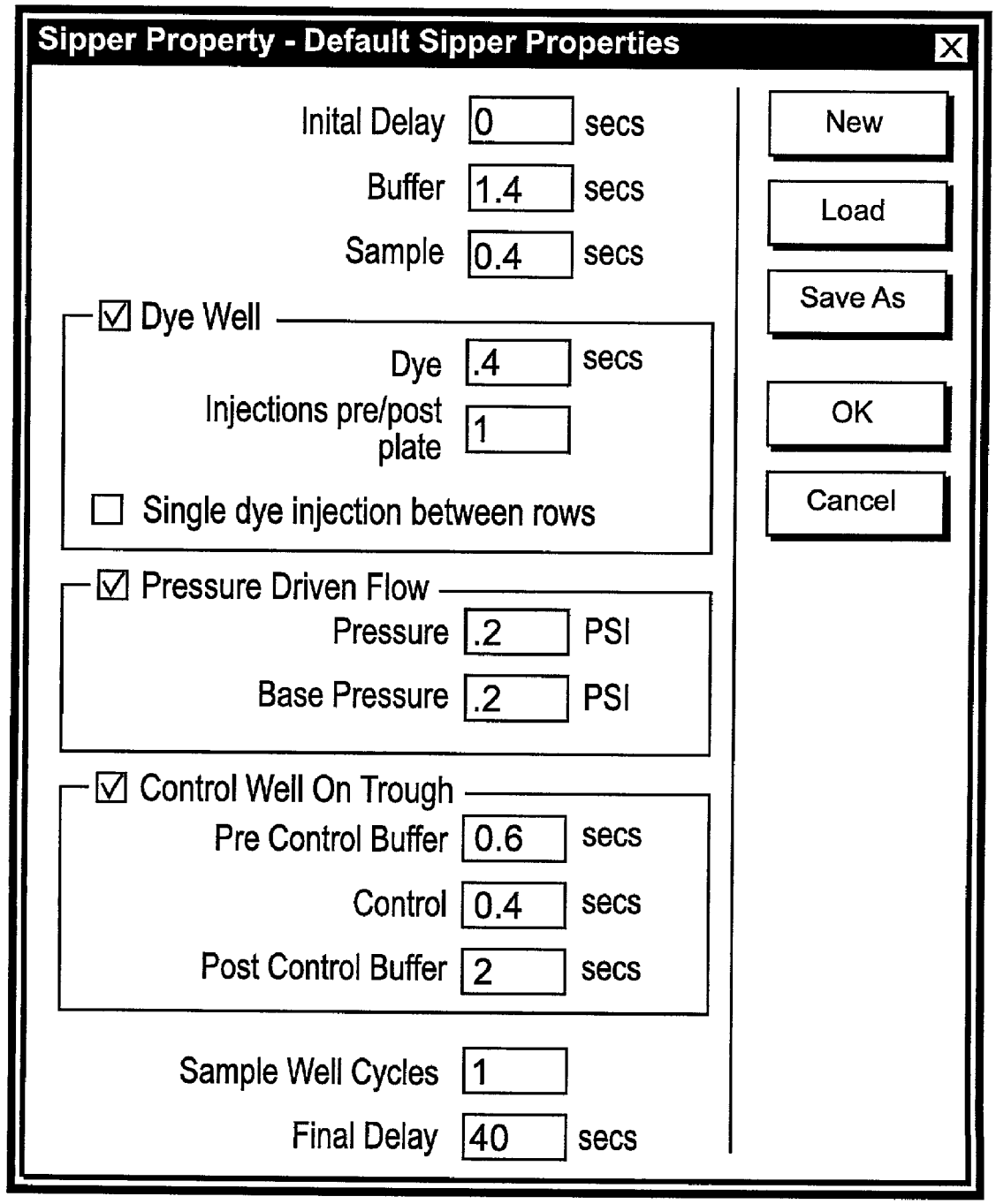

2. In the Sipper Properties dialog box, enter sipping times for Initial Delay, Buffer, and Sample. The initial delay is typically the length of time before the dwell pattern is started. To run the system at maximum throughput, this value is set to zero. The buffer parameter includes the length of buffer sipping time, which is typically long enough to amply flush the channels. Similarly, the sample parameter includes the length of sample sipping time, which is typically set long enough to amply fill the channels. In general, the times for all of these parameters depend on the type and conditions of the particular assay. Additionally, the Dye Well and Control Well are typically set by clicking the General tab in the Multi-Sipper Options dialog box located under the Tools menu in the Multi-Sipper window and selecting Use Trough for Buffer and Dye Wells. FIG. 14B shows a display screen for performing this step.

3. Set the Dye Well parameters by (a) checking the Dye Well group box to activate the other choices, (b) entering the dye sipping time in the Dye field (minimum of 1 second), (c) entering 1 in the Injections pre/post plate field, and (d) clicking the Single dye injection between rows check box to sample dye between each row. In preferred embodiments, the sample and dye times are equal. Additionally, sampling dye pre and post microplates and between each row is typically performed to enable data analysis applications.

4. Set the pressure by clicking the Pressure Driven Flow check box and then enter a value between about −1 and about −3 in the Pressure field. For fluorogenic assays, a pressure of about −2 is generally preferred. This is equivalent to about −1.33 psi in a single capillary element. For mobility shift assays, the optimal pressure will typically depend on the conditions of the particular assay. In addition, set the Base Pressure to the same or a lower value. This is the pressure that is maintained during loading and unloading of the plates and when the run has completed, during which times, e.g., the capillary elements are disposed in a recirculation/replenishing bath or trough.

5. If control wells, e.g., located next to a container sampling region are to be utilized, click the Control Well on Trough checkbox. In the Pre Control Buffer field, enter the time in seconds for sampling buffer prior to sampling the control wells. This value should typically be long enough to bring the signal down to the substrate background and therefore depends upon the assay and the potency of the control. In the Control field, enter the time in seconds during which the capillary elements will sample the control wells. In the Post Control Buffer field, enter a time in seconds during which the capillary elements will sample buffer after sampling the control.

6. If single microwell plates are to be run, enter the number of times each dwell-pattern cycle is to be repeated for each plate in the Sample Well Cycles field. If a microfluidic device handling system is being utilized, enter 1 in this field. Multiple plate reading is optionally set in the Twister dialog box.

7. In the Final Delay field, enter the time for collecting baseline buffer data. The Final Delay sipping time is typically long enough to completely empty the capillary elements and the microchannels of the sample.

Figure 14C:
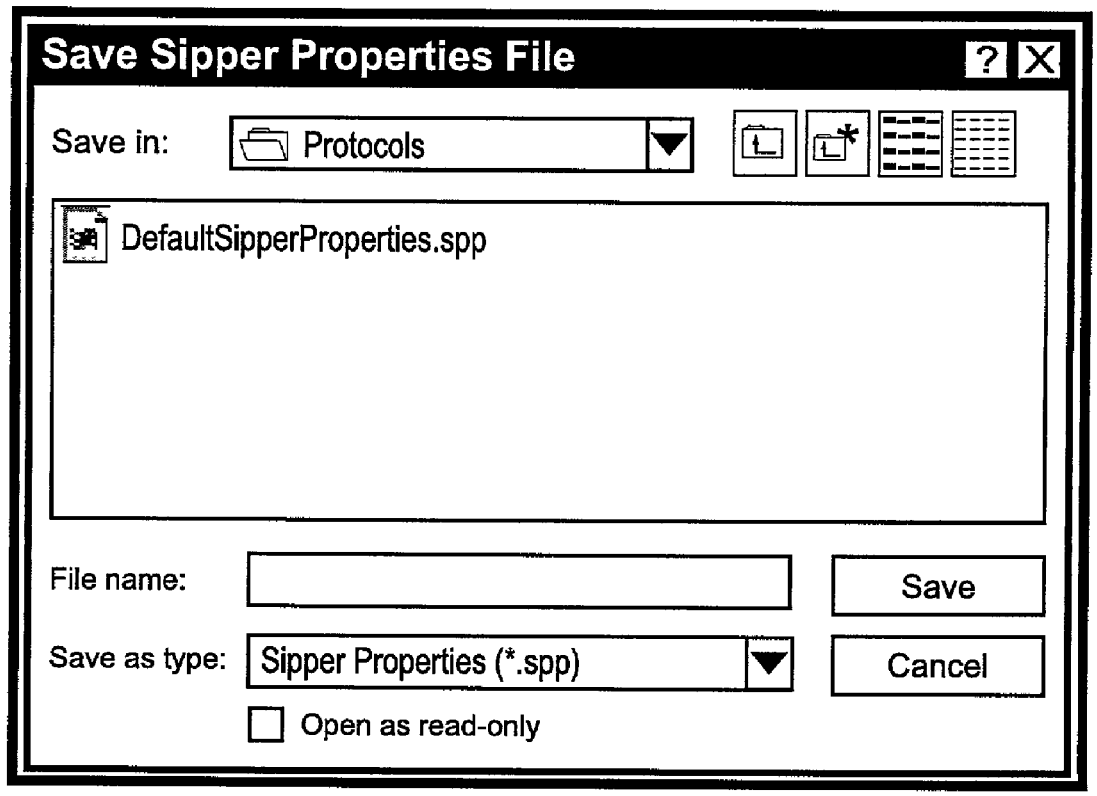

8. To save these settings for a future experiment, click Save As. The Save Sipper Properties File dialog box opens with the Protocols folder as the default save location. FIG. 14C shows a display screen for performing this step.

9. Enter a file name and click Save.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A computer-implemented method for selectively contacting microfluidic devices and arrayed materials, the method comprising:
   (a) providing a microfluidic device handling system operably connected to at least one computer, wherein the microfluidic device handling system is capable of implementing relative movement under instruction of the computer of one or more of at least one microfluidic device having n capillary elements extending therefrom, at least one array of materials having x material sites, and at least one container;
   (b) inputting one or more initial parameters for the at least one microfluidic device and the at least one array into the at least one computer, the at least one computer comprising at least one simple logic control program for selectively contacting at least one capillary element and material at at least one selected material site disposed in or on a surface of the at least one array; and,
   (c) implementing the at least one simple logic control program to effect:
      (i) moving the at least one microfluidic device relative to the at least one array, the at least one array relative to the at least one microfluidic device, or both, according to the one or more initial parameters, and (ii) contacting the at least one capillary element and the material at the at least one selected material site;

wherein the at least one simple logic control program optimizes a course for selectively contacting the at least one capillary element and the material at the at least one selected material site.

2. The method of claim 1, further comprising interchanging the at least one microfluidic device with at least one different microfluidic device, the at least one array with at least one different array, or both, wherein the at least one simple logic control program effects selective contacting of interchanged components.

3. The method of claim 1, wherein the one or more initial parameters comprise one or more of: an n-value, an x-value, a capillary element mask, an array mask, a number of columns of material sites, a number of rows of material sites, a mask for each row of material sites, a selection of materials at material sites to be contacted, a quantity or volume of the material to be drawn from the at least one selected material site, or a deselection of materials at material sites not to be contacted.

4. The method of claim 1, wherein the at least one capillary element comprises a capillary channel disposed therethrough.

5. The method of claim 1, wherein n corresponds to at least about 1, 2, 4, 6, 8, 12, or more capillary elements.

6. The method of claim 1, wherein x corresponds to at least about 1, 10, 50, 96, 250, 384, 500, 1000, 1536, 5000, 10000, 100000, or more material sites.

7. The method of claim 1, wherein (ii) further comprises drawing a selected quantity or volume of the material into the at least one microfluidic device through the at least one capillary element.

8. The method of claim 1, wherein the at least one container comprises at least one recirculation/replenishing bath or trough.

9. The method of claim 1, wherein the at least one simple logic control program comprises:

at least one instruction set for causing the at least one computer to effect movement of the at least one microfluidic device to the at least one selected material site or to the at least one container, to effect movement of the at least one array or the at least one container relative to the at least one microfluidic device, or both;

at least one instruction set for causing the at least one computer to effect contact of the at least one capillary element and the material at the at least one selected material site or fluidic material in the at least one container; and, at least one instruction set for causing the at least one computer to effect deselection of the at least one selected material site following (ii).

10. The method of claim 9, wherein the at least one simple logic control program further comprises at least one instruction set for causing the at least one computer to effect drawing of one or more selected quantities or volumes of the material from the at least one selected material site during (ii), to effect drawing of one or more selected volumes of fluidic material from the at least one container, or both.

11. The method of claim 9 or 10, wherein the at least one simple logic control program further comprises at least one instruction set for causing the at least one computer to vary or select a rate or a mode of moving or contacting the at least one capillary element and the material or fluidic material in the at least one container.

12. The method of claim 1, wherein the material comprises a first fluidic material.

13. The method of claim 12, wherein (b) further comprises inputting one or more initial parameters for the at least one container into the at least one computer, the at least one computer further comprising at least one simple logic control program for selectively contacting the at least one capillary element and a second fluidic material disposed in the at least one container.

14. The method of claim 13, wherein (ii) comprises dipping the at least one capillary element into the first fluidic material at the at least one selected material site.

15. The method of claim 14, wherein (c) further comprises:

(iii) moving the at least one microfluidic device relative to the at least one container, the at least one container relative to the at least one microfluidic device, or both, according to the one or more initial parameters or one or more updated parameters; and, (iv) dipping the at least one capillary element into the second fluidic material, and moving the second fluidic material relative to the at least one capillary element or moving the at least one capillary element relative to the second fluidic material.

16. The method of claim 15, wherein (c) further comprises:

(v) moving the at least one microfluidic device relative to the at least one array, the at least one array relative to the at least one microfluidic device, or both, according to the one or more initial parameters or the one or more updated parameters; and, (vi) dipping the at least one capillary element into a third fluidic material at at least one other selected material site, wherein (iv) dissipates at least one drop of the first fluidic material adhering to at least one portion of the at least one capillary element into the second fluidic material, thereby reducing fluid carryover from (ii) to (vi).

17. The method of claim 15, wherein the second fluidic material is disposed in at least one other selected material site of the at least one array, or in a fluidic container distinct from the at least one array.

18. The method of claim 15, wherein (iv) further comprises moving both the at least one capillary element and the second fluid material simultaneously relative to one another.

19. The method of claim 15, comprising moving the second fluidic material in at least one fluid stream or in a fluid recirculation/replenishing bath or trough.

20. The method of claim 15, wherein the second fluidic material comprises at least one solution selected from the group consisting of: a wash solution, a rinse solution, a buffer solution, a reagent solution, a sample solution, and a spacer solution.

21. The method of claim 15, wherein (ii) further comprises drawing at least a portion of the first fluidic material into the at least one capillary element.

22. The method of claim 15, wherein (iv) further comprises drawing at least a portion of the second fluidic material into the at least one capillary element.

23. The method of claim 22, wherein (iv) dissipates carried-over first fluidic material in the second fluidic material thereby reducing an amount of the carried-over first fluidic material drawn into the at least one capillary element.

24. The method of claim 1, wherein the at least one array comprises at least one microwell plate, substrate, or membrane.

25. The method of claim 24, wherein the x material sites correspond to x wells in the at least one microwell plate, or to x sample sites on the at least one substrate or membrane.

26. The method of claim 1, the method further comprising:
(iii) updating the one or more initial parameters; and, optionally:
(iv) repeating (i), (ii), and (iii) until each selected capillary element of the microfluidic device and materials at each selected material site are contacted.

27. The method of claim 26, wherein the at least one simple logic control program automatically directs each (i), (ii), and (iii).

28. The method of claim 26, wherein the at least one simple logic control program automatically updates the one or more initial parameters by deselecting material at each material site contacted by the at least one capillary element following each repeated cycle of (i) and (ii).

29. An integrated system, comprising:
at least one computer;
a microfluidic device handling system operably connected to the at least one computer, wherein the microfluidic device handling system is capable of implementing relative movement under instruction of the at least one computer of one or more of at least one microfluidic device having n capillary elements extending therefrom, at least one array of materials having x material sites, and at least one container;
a computer readable medium operably connected to the at least one computer that stores at least one simple logic control program for selectively contacting at least one capillary element and a material at at least one selected material site disposed in or on a surface of at least one array or a fluid in the at least one container, the at least one simple logic control program comprising:
at least one instruction set for causing the at least one computer to receive one or more inputted initial parameters;
at least one instruction set for causing the at least one computer to effect movement of the at least one microfluidic device to the at least one selected material site or to the at least one container according to one or more inputted initial parameters or one or more updated parameters, to effect movement of the at least one array or the at least one container relative to the at least one microfluidic device according to one or more inputted initial parameters or one or more updated parameters, or both;
at least one instruction set for causing the at least one computer to effect contact of the at least one capillary element and the material or the fluid according to one or more inputted initial parameters or one or more updated parameters; and,
at least one instruction set for causing the at least one computer to effect deselection of the at least one selected material site following contact between the at least one capillary element and the material;
wherein the at least one simple logic control program optimizes a course for selectively contacting the at least one capillary element and the material at the at least one selected material site.

30. The integrated system of claim 29, wherein the at least one simple logic control program further comprises:
at least one instruction set for causing the at least one computer to vary or select a rate or a mode of moving or contacting the at least one capillary element and the material or the fluid, to vary or select a rate or a mode of moving the at least one array or the at least one container, or both;
at least one instruction set for causing the at least one computer to effect drawing of one or more selected quantities or volumes of the material from the at least one selected material site into the at least one microfluidic device through the at least one capillary element according to one or more inputted initial parameters or one or more updated parameters while the at least one capillary element and the material are in contact, to effect drawing of one or more selected quantities or volumes of the fluid from the at least one container into the at least one microfluidic device through the at least one capillary element according to one or more inputted initial parameters or one or more updated parameters while the at least one capillary element and the fluid are in contact, or both; or, both.

31. The integrated system of claim 29 or 30, wherein the at least one simple logic control program further comprises at least one instruction set for causing the at least one computer to automatically update one or more inputted initial parameters or one or more other parameters.

32. The integrated system of claim 29, wherein the one or more inputted initial parameters or the one or more updated parameters comprise one or more of: an n-value, an x-value, a capillary element mask, an array mask, a number of columns of material sites, a number of rows of material sites, a mask for each row of material sites, a selection of materials at material sites to be contacted, a quantity or volume of the material to be drawn from the at least one selected material site, or a deselection of materials at material sites not to be contacted.

33. The integrated system of claim 29, wherein the computer readable medium comprises one or more of: a CD-ROM, a floppy disk, a tape, a flash memory device or component, a system memory device or component, a hard drive, or a data signal embodied in a carrier wave.

34. The integrated system of claim 29, wherein the at least one container comprises at least one recirculation/replenishing bath or trough.

35. The integrated system of claim 29, the microfluidic device handling system comprising:
a holder configured to receive the at least one microfluidic device;
a container sampling region proximal to the holder configured to receive the at least one array; and,
a controller which, during operation of the handling system, implements movement or interchange of the at least one microfluidic device, the array, or both, contact between the at least one capillary element and the material, and drawing of the material.

36. The integrated system of claim 35, wherein the at least one capillary element comprises a capillary channel disposed therethrough.

37. The integrated system of claim 35, wherein n corresponds to at least about 1, 2, 4, 6, 8, 12, or more capillary elements.

38. The integrated system of claim 35, wherein x corresponds to at least about 1, 10, 50, 96, 250, 384, 500, 1000, 1536, 5000, 10000, 100000, or more material sites.

39. The integrated system of claim 35, wherein the at least one array comprises at least one microwell plate, substrate, or membrane.

40. The integrated system of claim 39, wherein the x material sites correspond to x wells in the at least one microwell plate, or to x sample sites on the at least one substrate or membrane.

41. A computer program product comprising a computer readable medium having at least one simple logic control program stored thereon for causing a computer to selectively contact at least one capillary element of at least one microfluidic device having n capillary elements extending therefrom and one or both of material at at least one selected material site of at least one array of materials having x material sites and fluid in at least one container, the at least one simple logic control program comprising:

- at least one instruction set for causing the at least one computer to receive one or more inputted initial parameters;
- at least one instruction set for causing the at least one computer to effect movement of the at least one microfluidic device to the at least one selected material site or to the at least one container according to one or more inputted initial parameters or one or more updated parameters, to effect movement of the at least one array or the at least one container relative to the at least one microfluidic device according to one or more inputted initial parameters or one or more updated parameters, or both;
- at least one instruction set for causing the at least one computer to effect contact of the at least one capillary element and the material or the fluid according to one or more inputted initial parameters or one or more updated parameters; and,
- at least one instruction set for causing the at least one computer to effect deselection of the at least one selected material site following contact between the at least one capillary element and the material;
- wherein the at least one simple logic control program optimizes a course for selectively contacting the at least one capillary element and the material at the at least one selected material site.

42. The computer program product of claim 41, wherein the at least one simple logic control program further comprises:

- at least one instruction set for causing the at least one computer to vary or select a rate or a mode of moving or contacting the at least one capillary element and the material or the fluid, to vary or select a rate or a mode of moving the at least one array or the at least one container, or both;
- at least one instruction set for causing the at least one computer to effect drawing of one or more selected quantities or volumes of the material from the at least one selected material site into the at least one microfluidic device through the at least one capillary element according to one or more inputted initial parameters or one or more updated parameters while the at least one capillary element and the material are in contact, to effect drawing of one or more selected quantities or volumes of the fluid from the at least one container into the at least one microfluidic device through the at least one capillary element according to one or more inputted initial parameters or one or more updated parameters while the at least one capillary element and the fluid are in contact, or both; or, both.

43. The computer program product of claim 41 or 42, wherein the at least one simple logic control program further comprises at least one instruction set for causing the at least one computer to automatically update one or more inputted initial parameters or one or more other parameters.

44. The computer program product of claim 41, wherein the one or more inputted initial parameters or the one or more updated parameters comprise one or more of: an n-value, an x-value, a capillary element mask, an array mask, a number of columns of material sites, a number of rows of material sites, a mask for each row of material sites, a selection of materials at material sites to be contacted, a quantity or volume of the material to be drawn from the at least one selected material site, or a deselection of materials at material sites not to be contacted.

45. The computer program product of claim 41, wherein the computer readable medium comprises one or more of: a CD-ROM, a floppy disk, a tape, a flash memory device or component, a system memory device or component, a hard drive, or a data signal embodied in a carrier wave.

* * * * *